(12) United States Patent
Rafiee et al.

(10) Patent No.: US 12,402,835 B2
(45) Date of Patent: Sep. 2, 2025

(54) CATHETER AND ACTUATOR SYSTEMS AND METHODS

(71) Applicant: Transmural Systems LLC, Andover, MA (US)

(72) Inventors: Nasser Rafiee, Andover, MA (US); Biwei MacDonald, Andover, MA (US); Morgan House, Andover, MA (US); Koosha Rafiee, Andover, MA (US); Mai Le Diep, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 0 days.

(21) Appl. No.: 18/390,711

(22) Filed: Dec. 20, 2023

(65) Prior Publication Data
US 2024/0206815 A1 Jun. 27, 2024

Related U.S. Application Data

(63) Continuation of application No. PCT/US2023/084621, filed on Dec. 18, 2023.

(60) Provisional application No. 63/605,856, filed on Dec. 4, 2023, provisional application No. 63/533,271, filed on Aug. 17, 2023, provisional application No.
(Continued)

(51) Int. Cl.
| | |
|---|---|
| A61B 18/14 | (2006.01) |
| A61B 5/00 | (2006.01) |
| A61B 5/283 | (2021.01) |
| A61B 18/00 | (2006.01) |
| A61B 17/00 | (2006.01) |
| A61M 25/00 | (2006.01) |

(52) U.S. Cl.
CPC ............ *A61B 5/6859* (2013.01); *A61B 5/283* (2021.01); *A61B 18/1492* (2013.01); *A61B 2017/0003* (2013.01); *A61B 2018/00279* (2013.01); *A61B 2018/00369* (2013.01); *A61B 2018/00601* (2013.01); *A61B 2018/00839* (2013.01); *A61M 25/0074* (2013.01)

(58) Field of Classification Search
CPC .................. A61B 5/283; A61B 5/6859; A61B 2018/00225; A61B 2018/0038; A61B 2017/00225; A61B 2017/0003
See application file for complete search history.

(56) References Cited

U.S. PATENT DOCUMENTS

| | | |
|---|---|---|
| 4,493,320 A | 1/1985 | Treat |
| 5,341,807 A | 8/1994 | Nardella |

(Continued)

FOREIGN PATENT DOCUMENTS

| | | |
|---|---|---|
| DE | 10037660 A1 | 2/2002 |
| DE | 202010016945 U1 | 3/2011 |

(Continued)

OTHER PUBLICATIONS

Written Opinion mailed Jan. 27, 2022 for International Patent Application No. PCT/US2021/049952.
(Continued)

*Primary Examiner* — Eun Hwa Kim
(74) *Attorney, Agent, or Firm* — DeWitt LLP; Brian R. Pollack, Esq.

(57) ABSTRACT

The disclosure provides various embodiments of systems to facilitate the cutting of tissue structures and other tissue structures percutaneously.

18 Claims, 60 Drawing Sheets

Related U.S. Application Data

63/496,566, filed on Apr. 17, 2023, provisional application No. 63/477,317, filed on Dec. 27, 2022.

(56) References Cited

U.S. PATENT DOCUMENTS

| | | | |
|---|---|---|---|
| 5,417,697 | A | 5/1995 | Wilk et al. |
| 5,599,300 | A | 2/1997 | Weaver et al. |
| 5,807,279 | A | 9/1998 | Viera |
| 6,017,340 | A | 1/2000 | Cassidy et al. |
| 6,050,995 | A | 4/2000 | Durgin |
| 6,068,637 | A | 5/2000 | Popov et al. |
| 6,071,281 | A | 6/2000 | Burnside |
| 6,304,776 | B1 | 10/2001 | Muntermann |
| 6,501,992 | B1 | 12/2002 | Belden et al. |
| 6,517,551 | B1 | 2/2003 | Driskill |
| 6,533,782 | B2 | 3/2003 | Howell et al. |
| 6,582,425 | B2 | 6/2003 | Simpson |
| 6,695,836 | B1 | 2/2004 | DeMello et al. |
| 7,160,295 | B1 | 1/2007 | Garito et al. |
| 7,303,798 | B2 | 12/2007 | Bavaro et al. |
| 7,455,646 | B2 | 11/2008 | Richardson et al. |
| 8,100,903 | B2 | 1/2012 | Kennedy, II |
| 8,827,948 | B2 | 9/2014 | Romo et al. |
| 9,282,993 | B1 | 3/2016 | Cohen et al. |
| 9,572,666 | B2 | 2/2017 | Basude et al. |
| 9,833,272 | B2 | 12/2017 | Sweeney |
| 9,980,716 | B2 | 5/2018 | Harris et al. |
| 10,792,094 | B2 | 10/2020 | Hrnicek |
| 10,806,509 | B2 | 10/2020 | Gittard |
| 11,337,753 | B2 | 5/2022 | Rafiee et al. |
| 2002/0042611 | A1 | 4/2002 | Sliwa |
| 2003/0088195 | A1 | 5/2003 | Vardi et al. |
| 2004/0267161 | A1 | 12/2004 | Osborne et al. |
| 2005/0171532 | A1 | 8/2005 | Ciarocca |
| 2005/0203500 | A1 | 9/2005 | Saadat |
| 2007/0005084 | A1 | 1/2007 | Clague et al. |
| 2007/0083168 | A1* | 4/2007 | Whiting ............... A61M 25/007 604/264 |
| 2007/0197939 | A1* | 8/2007 | Wallace ............... A61M 25/01 600/587 |
| 2007/0293857 | A1 | 12/2007 | Blind et al. |
| 2008/0015409 | A1 | 1/2008 | Barlow et al. |
| 2008/0228209 | A1 | 9/2008 | DeMello et al. |
| 2009/0005637 | A1 | 1/2009 | Chin |
| 2010/0057077 | A1 | 3/2010 | Ducharme |
| 2010/0159396 | A1 | 6/2010 | Specht et al. |
| 2010/0204560 | A1 | 8/2010 | Salahieh |
| 2012/0083781 | A1* | 4/2012 | Schall ............... A61B 18/1206 606/33 |
| 2012/0123328 | A1 | 5/2012 | Williams |
| 2012/0259263 | A1 | 10/2012 | Celermajer et al. |
| 2014/0276605 | A1 | 9/2014 | Tejani et al. |
| 2014/0277333 | A1* | 9/2014 | Lewis ............... A61B 34/30 623/1.11 |
| 2016/0184557 | A1 | 6/2016 | Call et al. |
| 2016/0317174 | A1 | 11/2016 | Dake |
| 2017/0007277 | A1 | 1/2017 | Drapeau et al. |
| 2018/0008268 | A1 | 1/2018 | Khairkhakan |
| 2019/0175199 | A1 | 6/2019 | Girdhar et al. |
| 2019/0269392 | A1 | 9/2019 | Celermajer et al. |
| 2019/0298521 | A1 | 10/2019 | Rafiee et al. |
| 2019/0343634 | A1 | 11/2019 | Garvin |
| 2020/0146690 | A1 | 5/2020 | Rothstein et al. |
| 2020/0383717 | A1 | 12/2020 | Lederman et al. |
| 2021/0068892 | A1 | 3/2021 | Urbanski et al. |
| 2021/0137579 | A1 | 5/2021 | Rafiee et al. |
| 2021/0212756 | A1 | 7/2021 | Rafiee et al. |
| 2021/0228227 | A1 | 7/2021 | Vardi et al. |
| 2021/0307823 | A1* | 10/2021 | Urbanski ............... A61B 18/16 |
| 2022/0023046 | A1 | 1/2022 | Basude |
| 2022/0096103 | A1 | 3/2022 | Chou et al. |
| 2022/0110577 | A1 | 4/2022 | Highsmith et al. |
| 2022/0117736 | A1 | 4/2022 | Rafiee et al. |
| 2022/0296291 | A1 | 9/2022 | Anderson et al. |
| 2022/0361908 | A1 | 11/2022 | Karrowini et al. |
| 2023/0270424 | A1* | 8/2023 | Sarabia ............... A61B 18/1492 606/144 |
| 2023/0301784 | A1 | 9/2023 | Walters et al. |
| 2024/0099770 | A1* | 3/2024 | Kim ............... A61B 18/1492 |
| 2025/0000575 | A1* | 1/2025 | Lederman ............... A61B 90/39 |

FOREIGN PATENT DOCUMENTS

| | | |
|---|---|---|
| EP | 3175813 B1 | 1/2020 |
| RU | 2152757 C1 | 7/2000 |
| WO | 2018009718 A1 | 1/2018 |
| WO | 2019/040943 A1 | 2/2019 |
| WO | 2019164806 A1 | 8/2019 |
| WO | 2021072331 A1 | 4/2021 |
| WO | 2022066621 A1 | 3/2022 |
| WO | 2023069983 A1 | 4/2023 |
| WO | 2023/133499 A1 | 7/2023 |

OTHER PUBLICATIONS

International Search Report mailed Jan. 27, 2022 for International Patent Application No. PCT/US2021/049952.

Unpublished International Patent Application No. PCT/US2021/049952 downloaded from ePCT on Jan. 28, 2022.

Written Opinion of the International Searching Authority for International Application No. PCT/US2018/048177 mailed Nov. 19, 2018.

International Search Report for International Application No. PCT/US2018/048177 mailed Dec. 20, 2018.

Khan et al., "Intentional Laceration of the Anterior Mitral Valve Leaflet to Prevent Left Ventricular Outflow Tract Obstruction During Transcatheter Mitral Valve Replacement", JACC: Cardiovascular Interventions vol. 9, No. 17, 2016.

Babaliaros et al., "Intentional Percutaneous Laceration of the Anterior Mitral Leaflet to Prevent Outflow Obstruction During Transcatheter Mitral Valve Replacement First-in-Human Experience", JACC: Cardiovascular Interventions vol. 10, No. 8, 2017.

Lederman et al., "Preventing Coronary Obstruction During Transcatheter Aortic Valve Replacement From Computed Tomography to Basilica", JACC: Cardiovascular Interventions vol. 12, No. 13. 2019, pp. 1197-1216.

Khan et al., "Predicting Left Ventricular Outflow Tract Obstruction Despite Anterior Mitral Leaflet Resection the "Skirt NeoLVOT"", JACC: Cardiovascular Interventions Sep. 2019, vol. 11, No. 9, pp. 1356-1359.

Case, "Tip to Base Lampoon to PRevent Left Ventricular Outflow Tract Obstruction in Valve in Valve Transcatheter Mitral Valve Replacement", JACC: Cardiovascular Interventions, May 2020, vol. 13, No. 9, pp. 1126-1128.

Greenbaum et al., "First-in-human transcatheter pledglet-assisted suture tricuspid annuloplasty for severe tricuspid insufficiency," Catheterization and Cardiovascular Interventions, May 2020, 5 pages.

Kamioka et al., "Bi-Silica During Transcatheter Aortic Valve Replacement for Noncalcific Aortic Insufficiency: Initial Human Experience", JACC: Cardiovascular Interventions, Nov., 2018, vol. 11, No. 21, pp. 2237-2239.

Kasel et al, "International Lampoon: First European experience with laceration of the anterior mitral valve leaflet prior to transseptal transcatheter mitral valve implantation", Eurointervention, Sep. 2018, col. 14, No. 7, pp. 746-749.

Khan et al, "The Basilica Trial: Prospective Multicenter Investigation of Intentional Leaflet Laceration to Prevent TAVR Coronary Obstruction", JACC: Cardiovascular Interventions, 2019, vol. 12, No. 13, pp. 1240-1252.

Khan et al, "Transcatheter Mitral Valve Replacement after Transcatheter Electrosurgical Laceration of Alfieri stitch (Elastic): First in human report," JACC: Cardiovascular Interventions, Apr. 2018, vol. 11, No. 8, pp. 1808-1811.

Khan et al, "Transcatheter Electrosurgery: JACC State of the art review," Journal of the American College of Cardiology, Mar. 2020, vol. 75, No. 12, pp. 1455-1470.

(56) References Cited

OTHER PUBLICATIONS

Khan et al., "Antetrior Leaflet Laceration to Prevent Ventricular Outflow Tract Obstruction During Transcatheter Mitral Valve Replacement," Journal of the American College of Cardiology, May 2019, vol. 73, No. 20, pp. 2521-2534.
Khan et al, "Rescue Lampoon to Treat Transcatheter Mitral Valve Replacement—Associated Left Ventricular Outflow Tract Obstruction", JACC: Cardiovascular Interventions, Jul. 2019, vol. 12, No. 13, pp. 1283-1284.
Lisko et al., "Pachyderm Shape guiding catheters to simplify Basilica leaflet traversal," Cardiovsacular Revascularization Medicine, Sep. 2019, vol. 20, No. 9, pp. 782-785.
Lisko et al., "Electrosurgical detachment of Mitraclips from the anterior mitral leaflet prior to transcatheter mitral valve implantation," JACC: Cardiovascular Interventions, Oct. 2020, vol. 13, No. 20, pp. 2361-2370.
Khan et al., "Lampoon to facilitate tendyn Antetrior Leaflet Laceration to Prevent Ventricular Outflow Tract Obstruction During Transcatehter Mitral Valve Replacement," Journal of the American College of Cardiology, May 2019, vol. 73, No. 20, pp. 2521-2534.
International Search Report mailed Jun. 22, 2023 for International Application No. PCT/US23/60223.
Written Opinion and International Search Report mailed Mar. 1, 2021 for International Patent Application No. PCT/US2020/055160.
Written Opinion and International Search Report mailed Oct. 22, 2021 for International Patent Application No. PCT/US2021/040511.
Extended European Search Report for Application No. 18848165.9 dated Apr. 30, 2021.
Supplementary European Search Report and European Search Opinion for Application No. 19756527.8 dated Oct. 18, 2021.
International Search Report for co-pending international application No. PCT./US2023/084619, mailed Apr. 17, 2024.
International Search Report for co-pending international application No. PCT/US2023/084620, mailed Apr. 18, 2024.
International Search Report for co-pending international application No. PCT/US2023/084621, mailed May 30, 2024.
Written Opinion of the International Searching Authority for co-pending international application No. PCT/US2023/084619, mailed Apr. 17, 2024.
Written Opinion of the International Searching Authority for co-pending international application No. PCT/US2023/084620, mailed Apr. 18, 2024.
Written Opinion of the International Searching Authority for co-pending international application No. PCT/US2023/084621, mailed May 30, 2024.
Non-final office action mailed Mar. 14, 2024 in co-pending U.S. Appl. No. 18/390,687.
Non-final office action mailed Apr. 8, 2024 in co-pending U.S. Appl. No. 18/390,711.

* cited by examiner

Access Apical Side of Hump

Deploy Anchor Into Septum

Proximal

Distal

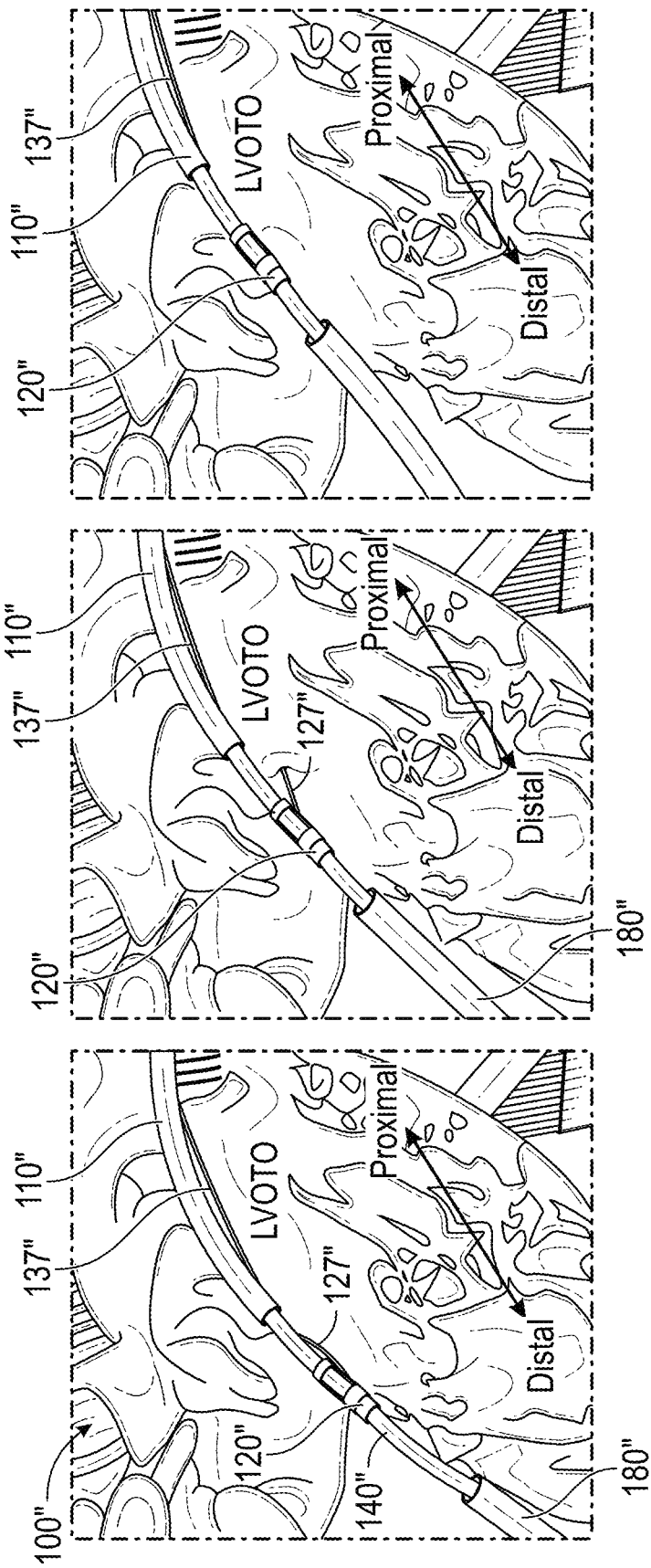

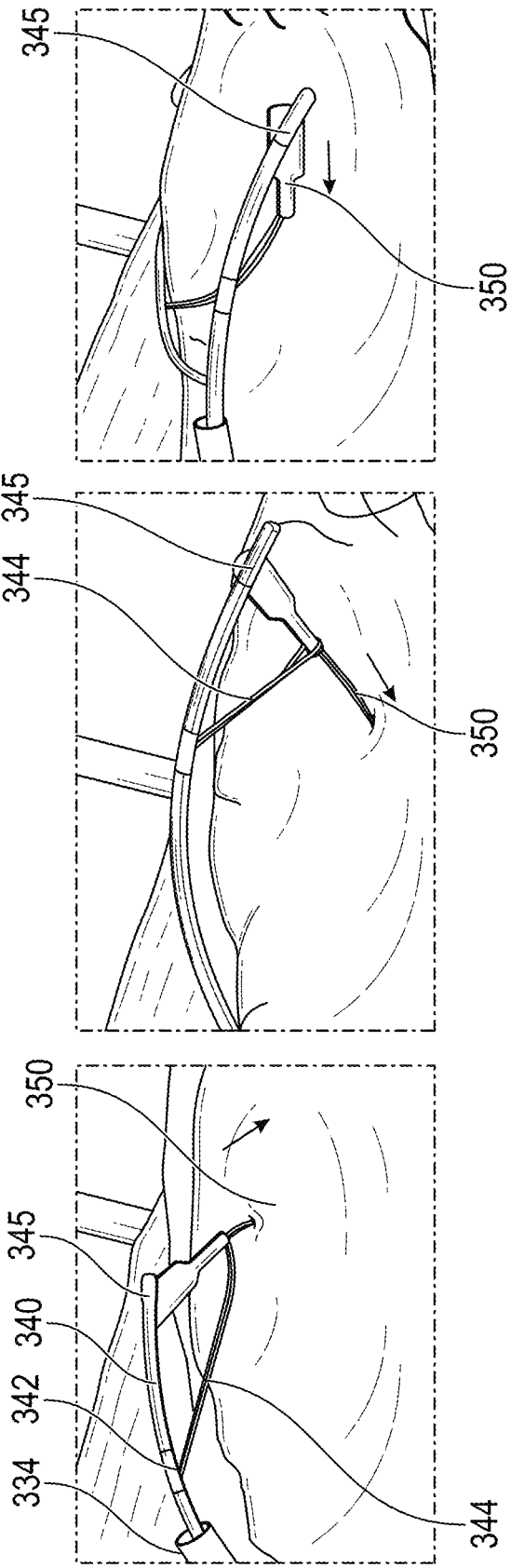

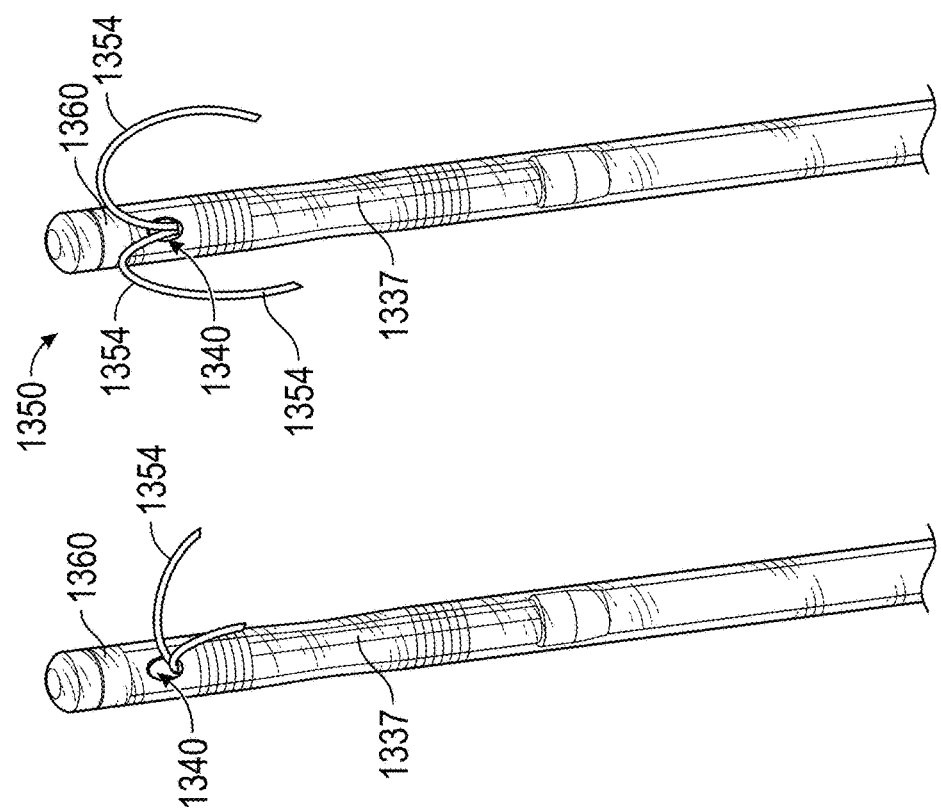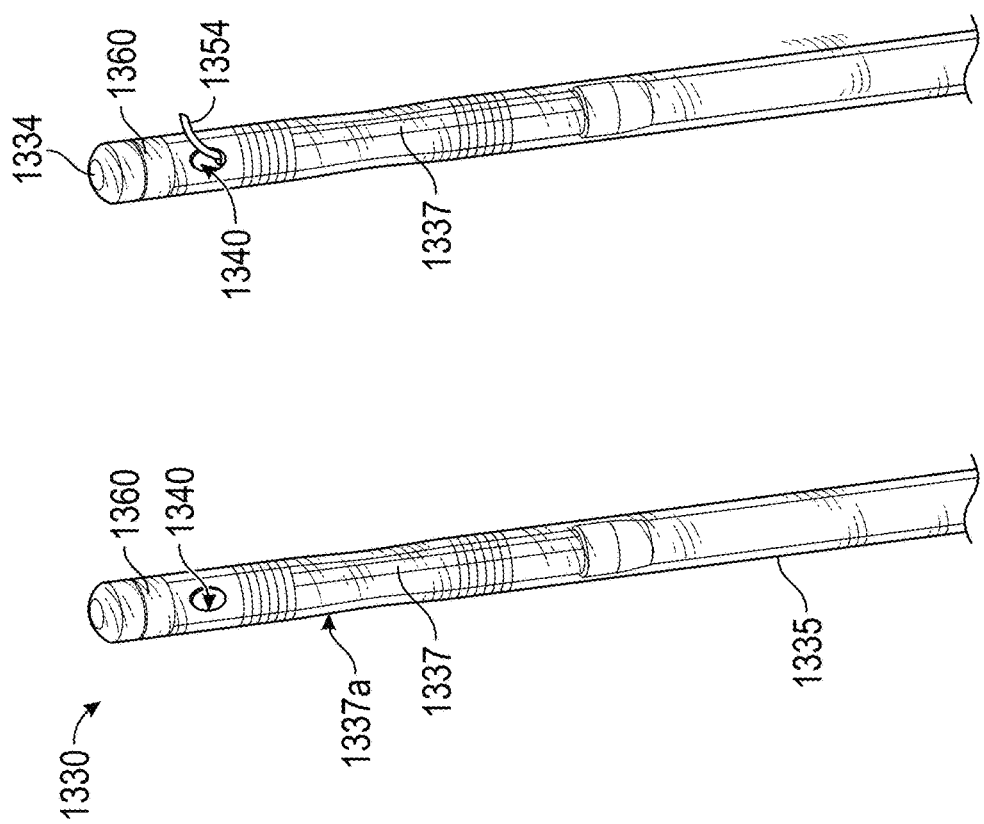

CATHETER AND ACTUATOR SYSTEMS AND METHODS

CROSS-REFERENCE TO RELATED APPLICATIONS

The present patent application claims the benefit of priority to and is a continuation of International Patent Application No. PCT/US2023/84621, filed Dec. 18, 2023, which in turn claims the benefit of priority to U.S. Provisional Patent Application No. 63/477,317, filed Dec. 27, 2022, U.S. Provisional Patent Application No. 63/496,566, filed Apr. 17, 2023, U.S. Provisional Patent Application No. 63/533,271, filed Aug. 17, 2023, and U.S. Provisional Patent Application No. 63/605,856, filed Dec. 4, 2023. Each of the aforementioned patent applications is incorporated by reference herein in its entirety for all purposes.

BACKGROUND

The disclosure relates generally to medical treatment devices and techniques, and, in some aspects, to methods and devices for diagnosis and treatment of myocardial tissue. The present disclosure provides improvements over the state of the art.

SUMMARY OF THE DISCLOSURE

BASILICA and LAMPOON are aortic and mitral leaflet laceration procedures that use transcatheter electrosurgery. A guidewire traverses potentially obstructive heart valve leaflet tissue and then the inner-curvature of the kinked guidewire traversing the leaflet is electrified during traction to accomplish a longitudinal split of the leaflet.

Left ventricular outflow tract (LVOT) obstruction complicates hypertrophic cardiomyopathy and transcatheter mitral valve replacement. Septal reduction therapies including surgical myectomy and alcohol septal ablation are limited by surgical morbidity or coronary anatomy and high pacemaker rates respectively. Applicants have developed a novel transcatheter procedure, mimicking surgical myotomy, called SESAME (SEptal Scoring Along the Midline Endocardium). The SESAME procedure uses an insulation-modified guidewire to lacerate myocardium (heart muscle) instead of heart leaflet tissue, using a different system design from the BASILICA and LAMPOON procedures. In some aspects, the SESAME electrosurgical procedure can include an asymmetric insulation gap astride the guidewire kink, or bend. The kink or bend concentrates electrical charge and helps to position the charge-delivery-device at the therapy target to avoid bystander injury. The insulation gap, discussed below; is intended to overcome the tendency of charge to concentrate on the outer aspect of a kink.

In accordance with the present disclosure, implementations of a device to cut tissue are provided. Some such implementations include an elongate body having a proximal end and a distal end, an elongate tether operably coupled to the elongate body, wherein the elongate tether and elongate body are configured to be longitudinally displaceable with respect to one another. The device can further include a cutting element disposed on at least one of the elongate body and elongate tether, wherein relative longitudinal movement of the elongate tether and the elongate body causes the cutting element to cut through anatomical tissue that the device is placed adjacent to.

In some implementations, the elongate tether can be configured to be received at least partially within a lumen defined in the elongate body. The cutting element can include at least one blade that is configured to cut through tissue. The cutting element can include an electrically conductive element configured to be coupled to an electrical power source in order to electrify the electrically conductive element.

The cutting element can be disposed on an outer surface of the elongate body. Adjacent anatomical tissue can be cut by the cutting element as the elongate body is advanced or retracted along the elongate tether. In some implementations, the cutting element can include at least one blade that is configured to cut through tissue. The cutting element can include an electrically conductive element configured to be coupled to an electrical power source in order to electrify the electrically conductive element. The electrically conductive element can include at least one supply electrode configured to physically contact tissue to be cut. The supply electrode can be configured to be operably coupled to an electrical power supply to supply current to the supply electrode.

In some implementations, the device can further include a return electrode configured to direct current from a region proximate the supply electrode back to the electrical power supply. The return electrode is operably coupled to the tether. In some implementations, the device can further include a tissue anchor disposed at a distal end of the elongate tether. If desired, the return electrode is operably coupled to the anchor. The tether can include a return conductor along its length operably coupled to the return electrode. The return electrode can include the anchor. The at least one supply electrode can be disposed on an outer circumferential surface of the elongate body. The at least one supply electrode can be disposed on a distal tip of the elongate body. The at least one supply electrode can at least partially surround the tether.

In some implementations, the tether can exit through a distal end of the elongate body. In some implementations, the tether can exit through a lateral side port defined through a side wall of the elongate body proximate a distal end region of the elongate body. The device can further include a plurality of markers disposed along the tether separated by a predetermined spacing. In some implementations, the device can further include a guidewire passage disposed along at least a portion of a length of the elongate body. The guidewire passage can extend to a distal tip of the elongate body. The tether can exit the elongate body through a lateral side port defined in the elongate body. The tissue anchor and elongate tether can be coupled to a proximal anchor. The elongate tether can be movably disposed within a lumen of the elongate body along a majority of the length of the elongate body. The elongate body can be slidably disposed within a lumen of at least one outer deflectable catheter.

In some implementations, the device can further include an actuator assembly operably coupled to a proximal portion of the elongate body and to a proximal region of the elongate tether. The actuator assembly can be configured to permit a user to selectively move the elongate body with respect to the elongate tether. In some implementations, the actuator assembly can include (i) a first actuator operably coupled to a proximal end of the elongate body and (ii) a proximal anchor to secure a proximal region of the elongate tether. The first actuator can be configured to longitudinally displace the elongate member with respect to the proximal anchor to permit the elongate body to be selectively moved proximally and distally with respect to the proximal anchor. The elongate body can be configured to ride along the elongate tether.

In some implementations, the actuator assembly can further include a second actuator operably coupled to a proximal end of a first outer catheter. The first outer catheter can define a lumen along its length that surrounds the elongate member and the tether. The second actuator can be actuated to longitudinally displace the first outer catheter with respect to the elongate tether and the elongate body. The actuator assembly can further include a third actuator operably coupled to a proximal end of a second outer catheter. The second outer catheter can define a lumen along its length that surrounds the first outer catheter, the elongate member and the tether. The third actuator can be actuated to longitudinally displace the second outer catheter with respect to the elongate tether, the elongate body and the first outer catheter.

In some implementations, the first outer catheter and the second outer catheter can include active or passive steering mechanisms that permit the distal end region of each said catheter to be actively steered by a user. The elongate member can include an inner catheter that includes a steering mechanism to permit the distal end region of the inner catheter to be actively steered by a user. In some implementations, the elongate tether can be configured to be coupled to a distal anchor configured to be deployed into tissue proximate a distal end of the device. The proximal anchor can include a tensioner to selectively apply tension to the tether when the distal anchor is deployed into the tissue. The inner catheter can be configured to slide proximally and distally over the tether after the tether is tensioned. The first outer catheter can be configured to slide proximally and distally over the inner catheter. The second outer catheter can be configured to slide proximally and distally over the first outer catheter. Each of the proximal anchor, first actuator, second actuator and third actuator can be operably coupled to a respective carrier. Each respective carrier can be configured to slide on a common guide rail.

In some implementations, a proximal end of the inner catheter can be configured to be lifted out of the first actuator. A proximal end of the first outer catheter can be configured to be lifted out of the second actuator. A proximal end of the second outer catheter can be configured to be lifted out of the third actuator. The tensioner can include a first body coupled to the common guide rail and a second body that is movable with respect to the first body, wherein the second body is fixedly coupled to the tether. The second body can be coupled to the first body by an elastic member, such as a tension spring or a coiled spring, such as a flat spring. The second body can be movable from a first position wherein the tether is not tensioned to a second position wherein the tether is tensioned. The second body can be moved from the first position to the second position along a linear path. The second body can be moved from the first position to the second position along a curved path.

In some implementations, the first outer catheter can include a distally deployable anchor wire to facilitate anchoring a distal end of the first outer catheter in a desired location. The tether can include a tubular member that defines a passageway therethrough. The tissue anchor can be operably coupled to the distal end of the tether by way of a flexible coupling. The flexible coupling permits the tissue anchor to swivel with respect to the distal end of the tether. The at least one supply electrode can include at least one electrode configured to supply current, at least one electrode to return current to a power source to complete a circuit, and at least one sensing electrode; which can comprise the same physical electrodes, or different physical electrodes.

In some implementations, a radiopaque marker can be provided proximate the lateral side port to permit a user to determine the longitudinal and rotational orientation of the lateral side port. The elongate tether can include an elongate tubular member, and the tissue anchor can be configured to be deployed out of a distal port of the elongate tubular member. The tissue anchor can be pivotally coupled about a pivot point to a distal end of an elongate inner member disposed within the elongate tubular member. The device can further include a tension member coupled proximate a distal end of the tissue anchor. The tension member can be directed proximally through the elongate tubular member to be externalized from a patient. Applying tension to the tension member causes the anchor to articulate about the pivot point until at least one tine of the tissue anchor points along a proximal direction. The device can further include at least one visualization marker proximate a distal end or an exit port of at least one of the elongate body, the first outer catheter, the second outer catheter, the elongate tether, and the anchor. One or more of the visualization markers can include radiopaque material. One or more of the visualization markers can be configured to be visible under a magnetic resonance imaging modality. In some implementations, one or more of the first actuator, second actuator and third actuator can be operably coupled to an automated surgical device.

In some implementations, the disclosure provides implementations of a medical device including an elongate body having a proximal end and a distal end, and an elongate tether operably coupled to the elongate body. The elongate tether and elongate body can be configured to be longitudinally displaceable with respect to one another. The device can further include an electrode disposed on at least one of the elongate body and elongate tether, and electrical circuitry operably coupled to the electrode. The electrical circuitry can be configured to determine a state of at least one of the medical device and the anatomical tissue. The electrical circuitry can be configured to detect an incoming signal from the anatomical tissue to confirm that the electrode is in physical contact with the anatomical tissue. The incoming signal from the anatomical tissue can include an electrocardiogram signal from cardiac tissue. If desired, the electrical circuitry can be configured to detect a voltage or current drop across the electrode after electrical power has been applied to the electrode. In some implementations, relative longitudinal movement of the elongate tether and the elongate body can cause the electrode to cut through anatomical tissue that the device is placed adjacent to when the electrode is energized. The electrical circuitry can be configured to correlate the voltage or current drop with a state selected from the group consisting of (i) a state of tissue being cut by the electrode, (ii) a state of fouling of the electrode. The device can further include a pressure sensor located proximate the electrode. The pressure sensor can be operably coupled to the processor. The processor can be programmed to determine at least one biological parameter based on receiving a signal from the pressure sensor, the at least one biological parameter.

The elongate body can be configured to be held stationary adjacent anatomical tissue. The at least one cutting element can be disposed on the elongate tether. The elongate tether and cutting element can be configured to be slid alongside or within the elongate body in a reciprocating manner while the elongate body is held in a stationary position adjacent the anatomical tissue. The elongate tether can be configured to be received at least partially within a lumen defined in the elongate body. The elongate tether can be configured to exit from a proximal exit port formed in the elongate body and further wherein the elongate tether can be configured to re-enter the elongate body in a distal entrance port. The elongate body can be configured to be bent into a deployed configuration along a region that includes the proximal exit port and the distal entrance port. The elongate body can be bent into the deployed configuration, and the elongate tether can be directed away from the elongate body when the elongate tether is under tension.

In some implementations, a distal end of the elongate tether is coupled to a distal portion of the elongate body by an elastic element that can stretch longitudinally, and further wherein the elastic element is configured to retract the elongate tether in a distal direction when tension is reduced on the proximal end of the tether. The elastic element can include a tension spring. The elongate body can be configured to be deformed at least partially around an anatomic structure to be cut by the device. The elongate tether can include a cutting electrode mounted thereon configured to be coupled to an electrosurgical power source. In some implementations, the device can further include a depth sensing electrode to sense the depth of the tissue that the elongate tether is passing through. In some implementations, the elongate body can include a flexible distal section disposed distally of the distal entrance port to conform to the anatomy of a patient's ventricle. If desired, the elongate tether can pass around a bearing surface located on or within the elongate body located distally of the distal entrance port, and the elongate tether can pass through the elongate body to permit both ends of the elongate tether to be externalized from a patient while performing a cutting operation in the patient's heart. The elongate body can define a first elongate body and a proximal end of the elongate tether can be coupled to a second elongate body configured to move alongside or at least partially within the first elongate body. The elongate tether can include at least one of a radiopaque wire, a radiopaque suture material, a textured body, a radiofrequency (RF) electrode and a razor wire. In some implementations, the elongate tether can be operably coupled to an outer tubular member that is configured to be advanced proximally and distally over the elongate body. The elongate tether can be configured to cause the outer tubular member to form a bowed shape when tension is applied to the elongate tether. The elongate tether can be configured to be biased laterally away from the outer tubular member when the outer tubular member is formed into the bowed shape to permit the at least one cutting element disposed on the elongate tether to cut through tissue as the outer tubular member is advanced proximally and distally over the elongate body. In some implementations, the elongate body can define a tissue anchor that deploys along a proximal direction from a first location wherein the tissue anchor is disposed at least partially within the elongate body to a second location wherein the tissue anchor is advanced outwardly from the elongate body along a proximal direction into a tissue mass.

In further accordance with the disclosure, implementations of a medical device are provided. The medical device can include an elongate tether having a proximal end and a distal end. The medical device can include a first tubular catheter surrounding the elongate tether and be slidably displaceable along and with respect to the elongate tether. The first tubular catheter can have a proximal end and a distal end. The medical device can include a second tubular catheter surrounding the first tubular catheter and be slidably displaceable along and with respect to the first tubular catheter. The second tubular catheter can have a proximal end and a distal end. The medical device can include a third tubular catheter surrounding the second tubular catheter and be slidably displaceable along and with respect to the second tubular catheter. The third tubular catheter having a proximal end and a distal end.

In further accordance with the disclosure, the medical device can further include an actuator assembly coupled to a respective proximal end of one or more of the elongate tether, the first tubular catheter, the second tubular catheter, and the third tubular catheter, where provided. In some implementations, the medical device can further include a tissue anchor operably coupled to the distal end of the elongate tether. The actuator assembly can include a proximal anchor operably coupled to the proximal end of the elongate tether. The proximal anchor can be configured to permit tension to be applied to the elongate tether when the tissue anchor is anchored in tissue.

In further accordance with the disclosure, the actuator assembly can further include a first actuator operably coupled to a proximal end of the first tubular catheter, wherein the first actuator is configured to advance and retract the first tubular catheter proximally and distally over the elongate tether. The actuator assembly can further include a second actuator operably coupled to a proximal end of the second tubular catheter. The second actuator can be configured to advance and retract the second tubular catheter proximally and distally over the first tubular catheter. The distal end of the second tubular catheter can be capable of being retracted proximally past the distal end of the first tubular catheter. The actuator assembly can further include a third actuator operably coupled to a proximal end of the third tubular catheter. The third actuator can be configured to advance and retract the third tubular catheter proximally and distally over the second tubular catheter. The distal end of the third tubular catheter can be capable of being retracted proximally past the distal end of the first tubular catheter and the distal end of the second tubular catheter.

In some implementations, at least one of the first tubular catheter, the second tubular catheter, and the third tubular catheter can include active or passive steering mechanisms that permit the distal end region of each said catheter to be actively steered by a user. Each of the proximal anchor, first actuator, second actuator and third actuator can be operably coupled to a respective carrier in the actuator assembly, and each respective carrier can be configured to slide on a common guide rail. The relative longitudinal position of each of the proximal anchor, first actuator, second actuator and third actuator can be longitudinally adjusted along the common guide rail with respect to other components mounted on the common guide rail. The device can further include at least one cutting element disposed on at least one of the elongate tether, first tubular catheter, second tubular catheter, and third tubular catheter. Relative longitudinal movement of the at least cutting element with respect to another component of the device can cause the cutting element to cut through anatomical tissue that the cutting element is placed adjacent to.

In some implementations, the device can further include at least one electrode disposed on at least one of the elongate tether, first tubular catheter, second tubular catheter, and third tubular catheter, wherein relative longitudinal movement of the at least one electrode with respect to another component of the device causes the at least one electrode to cut through anatomical tissue that the at least one electrode is placed adjacent to. The device can further include at least one visualization marker disposed on at least one of the elongate tether, first tubular catheter, second tubular catheter, and third tubular catheter. The at least one visualization marker can be used to visualize a distal region of the device while inside a patient to permit a user of the device to determine the relative axial and rotational location of different component systems relative to each other and surrounding anatomy.

The disclosure further provides implementations of method of performing a medical procedure. The method can include providing a device as described herein, directing the device according to a target location inside a patient, placing the distal end of the third tubular catheter in a first location, placing the distal end of the second tubular catheter in a second location located distally with respect to the first location, placing the distal end of the first tubular catheter in a third location located distally with respect to the second location, and performing a therapeutic or diagnostic procedure using at least one of the first tubular catheter, the second tubular catheter and the third tubular catheter.

In some implementations, a distal region of the third tubular catheter can be disposed in an aortic arch of a patient, a distal region of the second tubular catheter can be disposed through a cardiac valve of a patient, and the first tubular catheter can be manipulated to perform a therapeutic or diagnostic procedure. The therapeutic procedure can include cutting into a left ventricular outflow tract obstruction to increase the effective cross-sectional area of the left ventricular outflow tract. In some implementations, the first tubular catheter can include a microcatheter, and the method can include directing the first tubular catheter into the right ventricle of the patient, through the septum of the patient into the left ventricle of the patient, and cutting into a left ventricular outflow tract obstruction to increase the effective cross-sectional area of the left ventricular outflow tract. In some implementations, the first tubular catheter can include a delivery catheter to deliver a beneficial agent or a medical device to an anatomical location. The first tubular catheter can include a cutting element to cut through anatomical tissue. The diagnostic or therapeutic procedure can be selected from the group including a MIRTH procedure, a LAMPOON procedure, an ANTEPASTA procedure, an ELASTIC procedure, a robotic surgical procedure, a cerclage procedure, or delivery of a medical device. The medical device can be selected from the group consisting of a stent and an artificial valve, such as an artificial cardiac valve including but not limited to an artificial mitral, aortic, tricuspid, or pulmonary valve, for example. The device is introduced into the patient by way of a femoral access point, a jugular access point, a carotid access point, or an apical access point through a wall of the heart, for example.

In some implementations, the at least one supply electrode can include a fin shaped electrode located on a dorsal surface proximate a distal end of the elongate body. If desired, the device can further include a flush port configured to flow a flushing fluid over the electrode when the at least one supply electrode is electrified. The device can further include a steering wire configured to cause a distal region of the device to laterally deflect.

The foregoing and other features and advantages of the disclosed technology will become more apparent from the following detailed description of several embodiments which proceeds with reference to the accompanying figures.

BRIEF DESCRIPTION OF THE FIGURES

FIGS. 22A-22C illustrate aspects of a further technique to treat a LVOTO in accordance with the present disclosure that includes deploying an anchor proximate a distal location of the LVOTO structure.

FIGS. 24A-25C illustrate aspects of still a further technique to treat a LVOTO in accordance with the present disclosure that includes deploying a further implementation of an anchor.

FIGS. 42A-42D are images of the catheter of FIG. 41 illustrating successive stages of deploying the tissue anchor out through the lateral side port of the catheter.

DETAILED DESCRIPTION

The present application presents advantages and improvements over systems described in International Patent Application No. PCT/US2023/060223, filed Jan. 6, 2023. The aforementioned patent application is incorporated by reference herein in its entirety for all purposes.

Implementations in accordance with the present disclosure provide improved systems and methods for cutting tissue, including but not limited to myocardial tissue. Implementations in accordance with the present disclosure can form a lengthwise cut through tissue utilizing a reciprocating cutter that cuts from an outer surface of an obstruction, such as a LVOTO, downwardly into the tissue. This can be contrasted with the techniques described in PCT/US2023/060223, which teaches forming a passageway through tissue near a bottom region of tissue to be cut, and then cutting the tissue above the passageway to complete the cut. It will be appreciated by those of skill in the art that the disclosed implementations are fundamentally different from those described in PCT/US2023/060223 in a variety of ways.

FIGS. 1-4 depict aspects of a left ventricular outflow tract obstruction ("LVOTO" herein). While the cutting of a LVOTO is specifically illustrated, it will be appreciated that the disclosed embodiments can be used for other purposes, including the cutting of myocardial tissue to debulk other cardiac structures, or to perform different percutaneous procedures in the cardiovascular system, a patient's sinus passages, within a patient's neurovascular structures, urinary structures, abdominal structures or digestive structures. Moreover, implementations in accordance with the present disclosure can be utilized in laparoscopic, thoracic, and other procedures.

Figure 1:
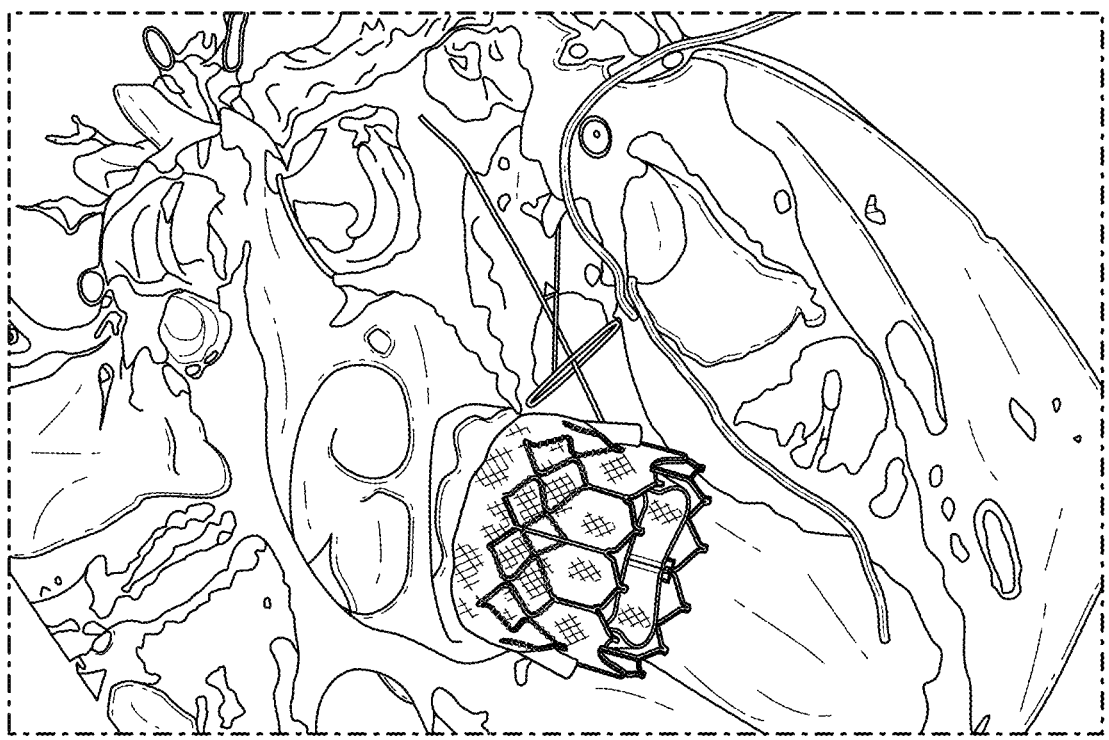
FIG. 1 is a representative illustration of a three-dimensional cardiac computed tomography image with a virtually embedded artificial SAPIEN™ valve in the mitral position to guide in predicting LVOT obstruction.

FIG. 1 is a representative illustration of a three-dimensional cardiac computed tomography image with a virtually embedded artificial SAPIEN™ valve in the mitral position to guide in predicting LVOT obstruction. In some implementations of procedures according to the present disclosure, pre-procedure planning can include generating a dedicated cardiac computed tomography ("CT") image to measure one or more of a variety of variables to assist in performing a tissue cutting procedure. For example, the CT image can be used to determine, or closely estimate valve size. This can also be facilitated with a transesophageal echocardiogram ("TEE"). It is also possible to measure the actual internal dimension of the valve under visualization which can then be correlated with the true internal dimension of the failed bioprosthetic valve. Comparing the measured value with the known value of the device can provide a proper basis for scaling the image to more closely measure the actual dimensions of internal cardiac structures. With continuing reference to FIG. 1, it is further possible to measure the aorto-mitral angle, wherein a favorable angle is in excess of 105 degrees. Moreover, it is possible to measure, or to at least estimate, the dimensions of a neo-left ventricular outflow tract (LVOT) area after a "virtual" implantation of a SAPIEN valve, as depicted in FIG. 1. Preferably, the LVOT area will exceed 200 mm$^2$ to prevent LVOT obstruction. If the patient's septum is thick, alcohol septal ablation can be performed ahead of time to debulk the septum somewhat and decrease the risk of LVOT obstruction in cases where the predicted neo-LVOT area is less than 200 mm$^2$. It is also possible to perform balloon assisted translocation of the mitral anterior leaflet to prevent LVOT obstruction, which is a significant concern of transcatheter mitral valve replacement ("TMVR"). Success rates for TMVR procedures is about 94-97%, with 91-95% 30-day survival and 86% 1-year survival rates.

Figures 2A, 2B:
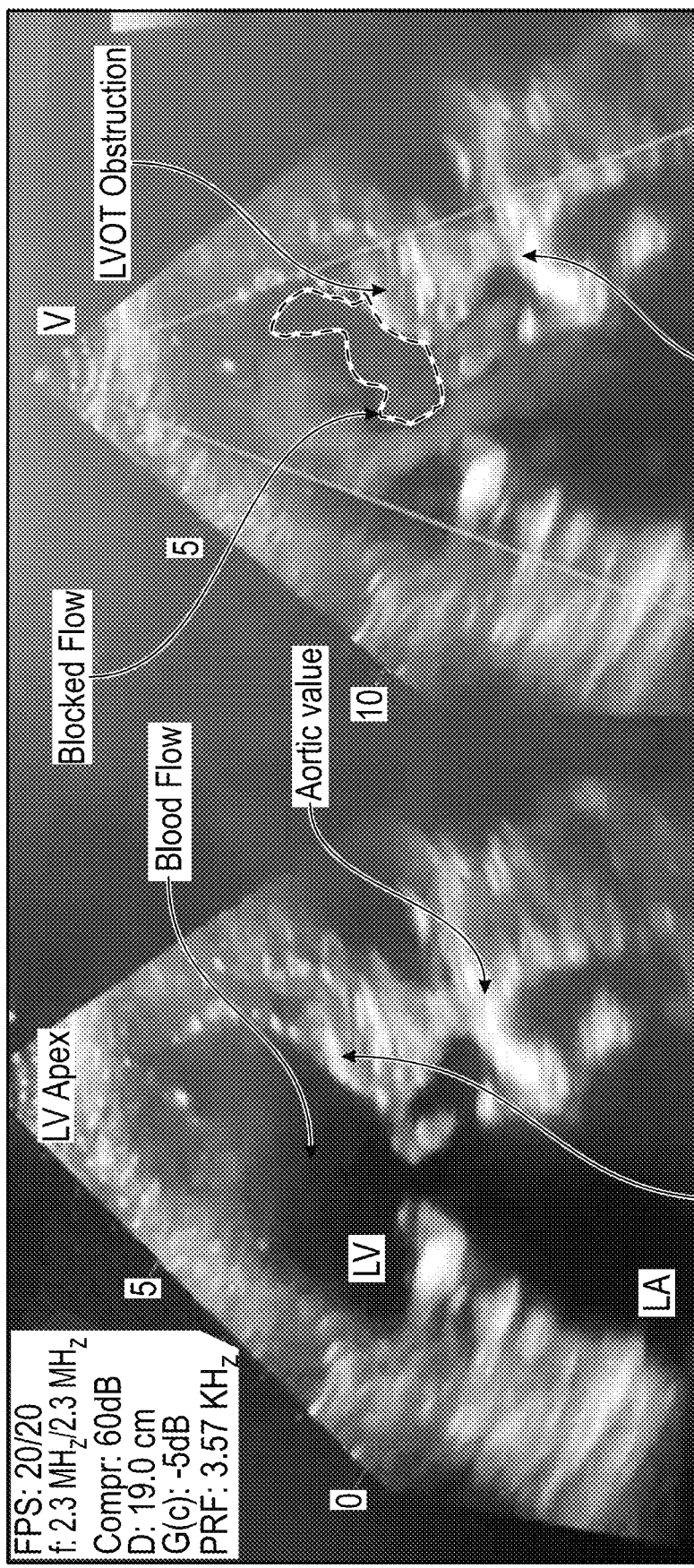
FIGS. 2A-2B are representative echocardiograms illustrating the presence of a flow obstruction within the left ventricular outflow tract that contributes to blocking blood flow to the aorta of a patient.

FIGS. 2A-2B are representative echocardiograms illustrating the presence of a flow obstruction within the left ventricular outflow tract that contributes to blocking blood flow to the aorta of a patient. In FIG. 2A, an LVOT obstruction is blocking blood flow (area inside dashed lines in FIG. 2B) to the aorta by way of the LVOT.

Figure 3:
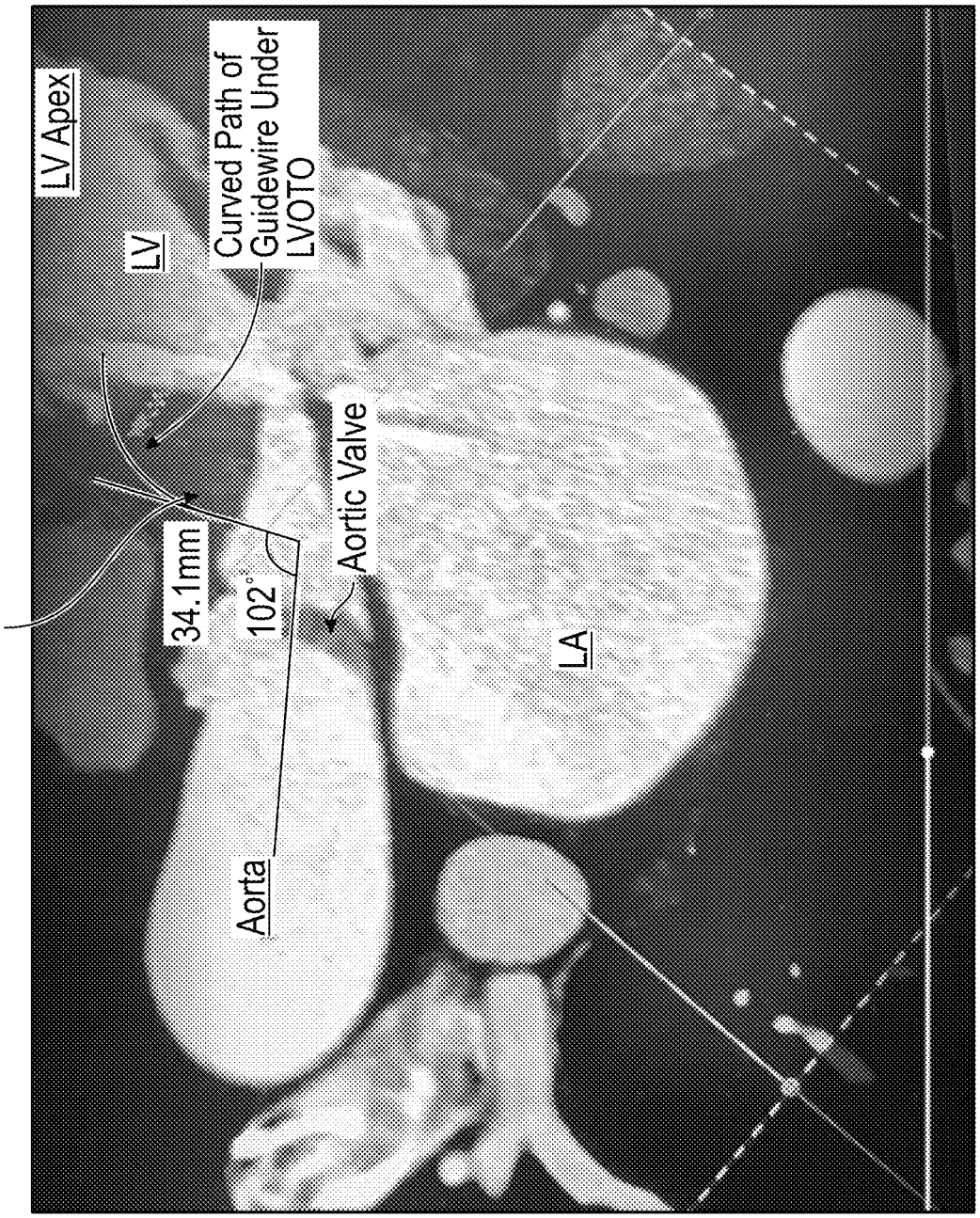
FIG. 3 is a representative computerized tomography (CT) scan illustrating a cross section of a patient's heart indicating the location of left ventricular outflow tract obstruction (LVOTO).

FIG. 3 is a representative computerized tomography (CT) scan illustrating a cross section of a patient's heart indicating the location of left ventricular outflow tract obstruction ("LVOTO"). The procedure described in PCT/US2023/060223 can be performed, wherein an electrified guidewire is navigated through the obstruction by tunneling through the mass starting at a proximal end of the mass (facing away from the ventricular apex) along a direction toward the ventricular apex where the guidewire exits the mass and re-enters the volume of the ventricle, effectively forming a tunnel through a bottom portion of the tissue mass. The distal end of the guidewire can be snared once exiting the tissue mass. The initial trajectory for the guidewire is perpendicular to the surface of the septum to penetrate the sometimes tough, basal septum. As seen in FIG. 3, the pathway of the guidewire is not straight, but curves off the initial vector to avoid crossing into the right ventricle and creating a ventricular septal defect ("VSD"). In FIG. 3, for purposes of clarity, "LA" refers to the left atrium and "LV" refers to the left ventricle.

Figure 4:
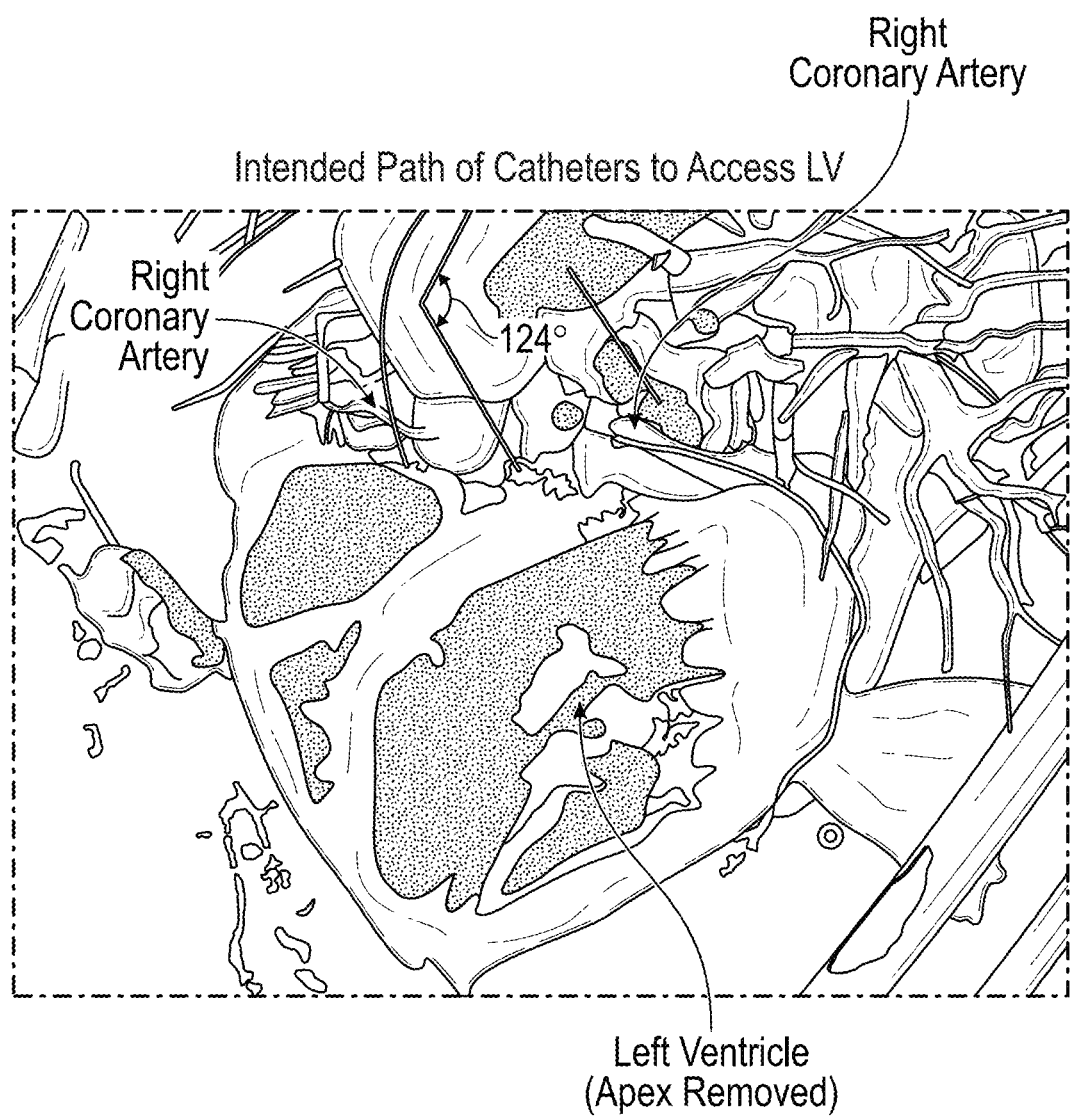
FIG. 4 is a further a representative computerized tomography (CT) scan illustrating a cross section of a patient's heart indicating a representative path of catheters to access the left ventricle of a patient.

FIG. 4 is a further representative "three-dimensional" computerized tomography (CT) scan illustrating a cross section of a patient's heart indicating a representative path of catheters to access the left ventricle of a patient. In FIG. 4, the path to the basal end of the intended cut typically starts just to the right side of the left-right commissure of the aortic valve. In view of the foregoing, and the teachings of PCT/US2023/060223, it will be appreciated that further approaches for performing similar procedures allowing additional device control during the procedure can be desirable.

Figure 5:
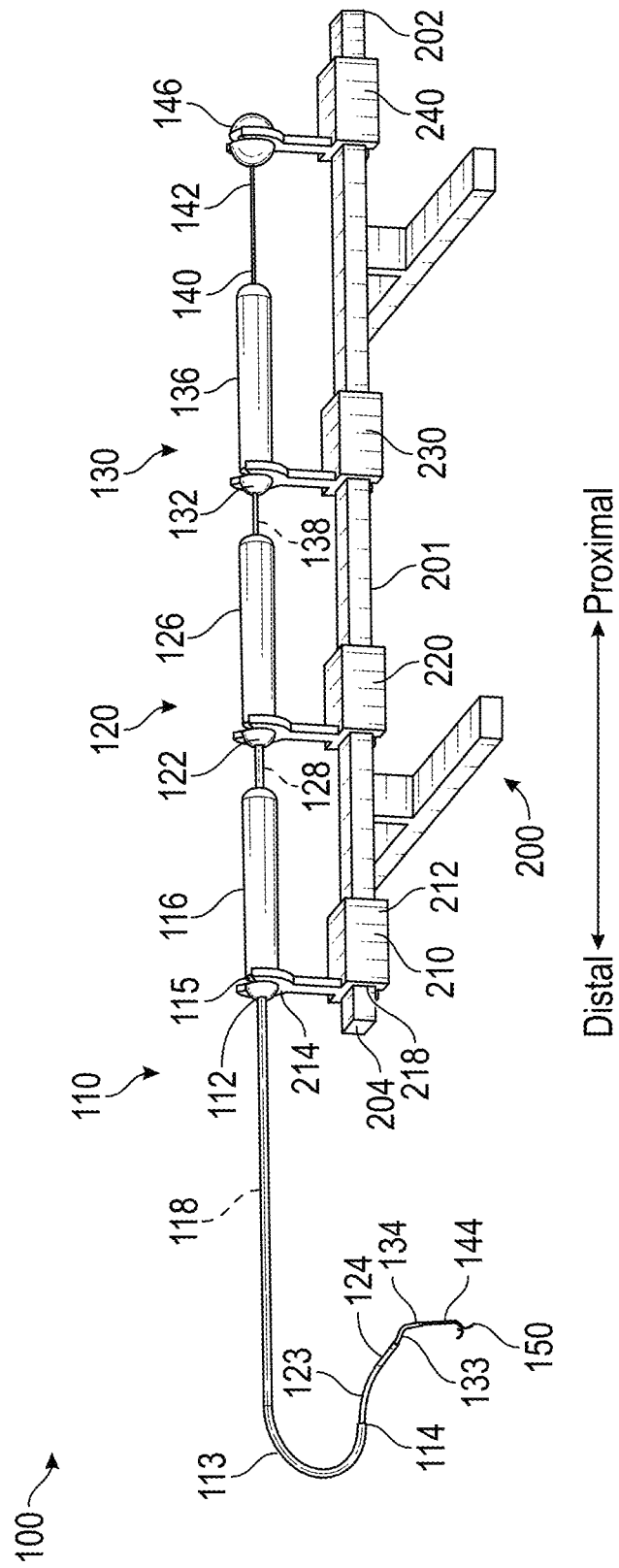
FIG. 5 is a representative implementation of a catheter-based system to perform a percutaneous procedure to cut tissue in accordance with the present disclosure using a reciprocating cutter.

Thus, in further accordance with the present disclosure, a first representative implementation for a system 100 for cutting tissue is depicted in FIG. 5. Further aspects of system 100 are depicted in FIGS. 6-12C.

FIG. 5 is a representative implementation of a catheter-based system 100 to perform a percutaneous procedure to cut tissue in accordance with the present disclosure. While the system 100 utilizes a reciprocating cutter (described below), the system 100 can be configured with different end effectors to perform different procedures. The system 100, as depicted includes three concentrically disposed deflectable catheters including a radially outermost catheter 110, within which a second deflectable intermediate catheter 120 is slidably received. A third, innermost deflectable catheter 130 is slidably disposed within deflectable catheter 120. A tether 140, or other instrumentality, such as a guidewire, a snare or the like is slidably received within catheter 130. Each deflectable catheter 110, 120, 130 can include one or more steering wires (not shown) to which tension can be applied to selectively cause the distal end (114, 124, 134) of each respective catheter (110, 120, 130) to bend in a preferential direction. Each catheter 110, 120, 130 is comprised of a tubular body having a proximal end coupled to an actuator and a free distal end. Each catheter 110, 120, 130 can be moved axially and rotationally with respect to the other components of system 100. Each catheter 110, 120, 130 is held in relative position by a respective carriage 210, 220, 230 that is slidably received on a rail 201 of a stand 200 of system 100. Each carriage 210, 220, 230 can be axially translated between the proximal end 202 and the distal end 204 of the rail 201. In some implementations, one or more of the carriages 210, 220, 230 can be locked in place with respect to the rail 201. As depicted, each catheter 110, 120, 130 is slidably received along a vertical direction into an upwardly extending portion of a respective carriage in a fork shaped coupling (e.g., 214). For example, a channel 115 is formed into catheter 100 that is slidably received within fork 214 to prevent axial movement of catheter 210 with respect to carriage 210. Each carriage (e.g., 210) is defined by a main body portion (e.g., 212) that defines a channel (e.g., 218) therethrough to at least partially surround rail 201 of stand 200.

Each of catheters 110, 120, 130 can be displaced rotationally about a central axis of system 100 (e.g., about tether 140) with respect to tether 140, and each other. It will be appreciated that any of catheters 110, 120, 130 can be utilized with stand 200 alone, or in combination with other system components. Thus, a triple catheter assembly may be used as depicted in FIG. 5, or a single or double catheter assembly may be used if all three catheters are not required. Catheters 110, 120, 130 can be of any desired length. In accordance with some implementations, catheter 110 can be between about 80 cm and about 120 cm in length, or any increment therebetween of about one centimeter. In accordance with further aspects, catheter 120 can be between about 90 cm and about 140 cm in length, or any increment therebetween of about one centimeter. In accordance with still further aspects, catheter 130 can be between about 100 cm and about 160 cm in length, or any increment therebetween of about one centimeter. Tether 140 can be any desired length, such as between about 120 and 300 cm in length, or any increment therebetween of about one centimeter.

With continuing reference to FIG. 5, outermost catheter 110 is comprised of an elongate tubular body 113 having a proximal end 112 operably coupled to an actuator 116 and a free distal end 114 that may be steered by tensioning a steering wire, for example, that is actuated by one or more buttons or levers within the actuator 116. Outermost catheter 110 further defines a lumen 118 (not shown) along at least a part of its length to slidably receive tubular shaft 123 of catheter 120. Catheter 110 can be slid along rail 201 and locked in place on rail 201, if desired. In use, the outer surface of tubular portion 113 of catheter 110 is fluidly sealingly received through an entrance port (not shown) that is fluidly coupled to a patient's anatomy. Consequently, in use, sliding movement of carriage 210 with respect to track or rail 201 results in proximal-distal movement of catheter 110 within a patient's vasculature independently of movement of catheters 120, 130, or tether 140.

Intermediate catheter 120, in turn, is comprised of an elongate tubular body 123 having a proximal end 122 operably coupled to an actuator 126 and a free distal end 124 that may be steered by tensioning a steering wire, for example, that is actuated by one or more buttons or levers within the actuator 126. Intermediate catheter 120 further defines a lumen 128 (not shown) along at least a part of its length to slidably receive tubular shaft 133 of catheter 130 therein. Intermediate catheter 120 can be slid along rail 201 and locked in place on rail 201, if desired, as with catheter 110. In use, the outer surface of tubular portion 123 of catheter 120 is fluidly sealingly received through an entrance port (not shown) located proximally or within actuator/handle 116 of catheter 110 to prevent undesired leakage of fluid between any annular clearance formed between the inner surface of lumen 118 and the outer surface of tubular member 123. As with catheter 110, in use, sliding movement of carriage 220) with respect to track or rail 201 results in proximal-distal movement of catheter 120 within a patient's vasculature independently of movement of catheters 110, 130, or tether 140. Further, catheter 120 can be displaced rotationally about central axis of system 100 (e.g., about tether 140) with respect to tether 140, catheter 110, and catheter 130.

With continuing reference to FIG. 5, innermost catheter 130 is comprised of an elongate tubular body 133 having a proximal end 132 operably coupled to an actuator 136 and a free distal end 134 that may be steered by tensioning a steering wire, for example, that is actuated by one or more buttons or levers within the actuator 136. Intermediate catheter 130 further defines a lumen 138 (not shown) along at least a part of its length to slidably receive tether 140 therethrough. Innermost catheter 130 can be slid along rail 201 and locked in place on rail 201, if desired, as with catheters 110, 120. In use, the outer surface of tubular portion 133 of catheter 130 is fluidly sealingly received through an entrance port (not shown) located proximally or within actuator/handle 126 of catheter 120 to prevent undesired leakage of fluid between any annular clearance formed between the inner surface of lumen 128 and the outer surface of tubular member 133. As with catheters 110, 120, in use, sliding movement of carriage 230) with respect to track or rail 201 results in proximal-distal movement of catheter 130 within a patient's vasculature independently of movement of catheters 110, 120, or tether 140. Further, catheter 130 can be displaced rotationally about central axis of system 100 (e.g., about tether 140) with respect to tether 140, catheter 110, and catheter 120.

Each of the catheters set forth herein (e.g., 110, 120, 130) can be made from a variety of materials, including multilayer polymeric extrusions, such as those described in U.S. Pat. No. 6,464,683 to Samuelson or U.S. Pat. No. 5,538,510 to Fontirroche, the disclosure of each being incorporated by reference herein in its entirety for all purposes. Other structures are also possible, including single or multilayer tubes reinforced by braiding, such as metallic braiding material. Any of the catheters or guidewires disclosed herein or portions thereof can be provided with regions of varying or stepped-down stiffness with length using any of the techniques set forth in U.S. Pat. No. 7,785,318, which is incorporated by reference herein in its entirety for any purpose whatsoever. The catheters herein (e.g., 110, 120, 130) can be provided with these and other structures to enhance pushability and torqueability. The catheters disclosed herein (e.g., 110, 120, 130) can have a varied stiffness along their length, particularly in their distal regions by adjusting the cross-sectional dimensions of the material to impact stiffness and flexibility, while maintaining pushability, as well as the durometer of the material. Hardness/stiffness is described herein with reference to Shore hardness durometer ("D") values. Shore hardness is measured with an apparatus known as a Durometer and consequently is also known as "Durometer hardness". The hardness value is determined by the penetration of the Durometer indenter foot into the sample. The ASTM test method designation is ASTM D2240 00. For example, in some implementations, a more proximal region of the catheter can have a durometer of about 72 D, an intermediate portion of the catheter (the proximal most 20-30 cm of the last 35 cm, for example that typically traverses an aortic arch) can have a durometer of about 55 D, and the distal 5-10 cm of the catheter can have a durometer of about 35 D.

Any surface of various components of the system described herein or portions thereof (e.g., 110, 120, 130, 140, 150) can be provided with one or more suitable lubricious coatings to facilitate procedures by reduction of frictional forces. Such coatings can include, for example, hydrophobic materials such as Poly TetraFluoroEthylene ("PTFE") or silicone oil, or hydrophilic coatings such as Polyvinyl Pyrrolidone ("PVP"). Other coatings are also possible, including, echogenic materials, radiopaque materials and hydrogels, for example.

With continuing reference to FIG. 5, tether 140 has a proximal end 142 operably coupled to a hub 146, or proximal anchor, that can be used to apply tension to tether 140. Tether 140 further includes a distal end 144 that extends distally from passage 138 from the distal end of innermost catheter 130. As depicted, hub 146 is removably coupled to carriage 240, wherein sliding movement of carriage 240) with respect to track or rail 201 results in proximal-distal movement of tether 140. Preferably, hub 146 and carriage 240 are used in order to maintain tension in tether or rail 140 to facilitate use of the system 100. For example, in some implementations, hub 146 can include a tension spring or elastic member that can be stretched to maintain tension in tether 140. Likewise, if desired, any one of the carriages 210, 220, 230, 240 may include an upper component that is slidably coupled to the main body portion (e.g., 210) of the respective carriage. If so equipped, the carriage can similarly include a tension spring to cause the catheter carried by the respective carriage to return to a desired axial location along the direction of rail 201. This can be useful, for example, in the instance of catheter 130, which can be spring loaded to return from a first deformed position to a contracted position between a first axial location and a second axial location to facilitate a reciprocating cutting operation.

Figure 6:
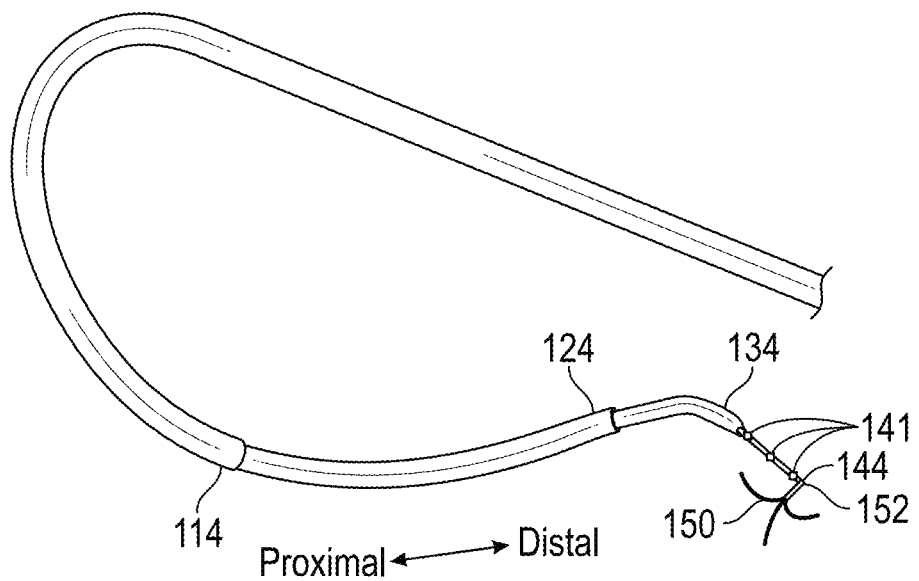
FIG. 6 illustrates aspects of the catheter-based system of FIG. 5 in accordance with some aspects of the present disclosure.

FIG. 6 illustrates further aspects of the catheter-based system 100 of FIG. 5 in accordance with some aspects of the present disclosure. For purposes of illustration, and not limitation, FIG. 6 illustrates a distal region of system 100 in accordance with some implementations of the disclosure. Illustrated are the distal end 114 of the outermost catheter 110, the distal end 124 of the intermediate catheter 120 extending distally from the lumen 118 of the outer catheter, and the distal end 134 of the innermost catheter 130 extending distally from the lumen 128 of the intermediate catheter 120. A distal region of tether 140 extends distally from the lumen 138 of the innermost catheter 130. The distal region of tether 140 can include a plurality of markers 141 that are visible under fluoroscopy or other imaging modality (e.g., MRI and the like) that are set a predetermined, and known, distance apart from each other. A distal end 144 of tether 140 is operably coupled to a tissue anchor 150. Tissue anchor 150 is anchored into tissue within a patient (discussed in further detail below) to permit tension to be applied to tether 140. Once a suitable amount of tension is present in tether 140, tether 140 acts as a guide rail to guide the movement, for example, of the distal end region of innermost catheter 130 to facilitate a tissue cutting operation. The anchor 150 can be provided with a proximally located pivoting coupling 152 to permit the tether 140 to pivot with respect to the anchor 150. The anchor 150 may be made from a radiopaque material, or may be provided with one or more radiopaque markers (not shown) or other markers, as desired. The markers (e.g., 141) can facilitate in situ measurement of a LVOTO, as well as helping to confirm the distance over which catheter 130 reciprocates to perform a cutting procedure, including helping to defined the proximal and distal movement limits of catheter 130) when a cutting element, such as an electrode, of catheter 130 is electrified. This can be used to control the length of the cut through the tissue. In some implementations, if desired, the tether 140 and anchor 150 may not be present and instead a microcatheter or needle (not shown) may be slidably received within lumen 138 of catheter 130. Moreover, innermost catheter 130 can be provided with a retractable and/or fixed electrode, as well as one or more sensors for detecting the presence of myocardium, and/or to detect electrical signals in the myocardium. In accordance with further implementations, the markers 141 and/or the anchor can be electrodes that provide a return path for electrical current that is supplied by supply electrode(s) defined in the distal region or near or at the distal end of catheter 130. If so equipped, tether 140) can include a conductive core, such as if tether 140 comprises an electrically conductive insulated tether. Anchor 150 and/or markers 141 can be in electrical communication with the conductive core of the tether 140 to provide a return path for the electrical current. In any implementation herein, a separate catheter, such as a pigtail catheter, can be provided an introduced alongside the system (e.g., 100) to provide a return electrode to provide a return path for electrical current and/or to control the direction of the flow of electrical current in a region of interest where a procedure is being performed on tissue of a patient. The cutting electrode and the return electrode are preferably moved together in tandem. The return electrode preferably has an enlarged surface area to reduce the current density at the surface electrode and to reduce ohmic heating of surrounding tissue to reduce or prevent undesired ablation and thermal effects.

In further accordance with the disclosure, the electrodes (e.g. supply, return, sensing, and the like) used in the various embodiments disclosed herein can have any desired length or shape, and if desired, can have exposed lengths that can be varied, such as by extending an exposed portion of an electrode outwardly through a port defined in an electrically insulating tubular member. The electrodes can have shapes or surface features configured to concentrate electrical charge and current density as desired. The catheters can be configured to direct flush fluid over or adjacent to electrodes to help aid in cooling the electrodes, and to help avoid the clotting of blood, and to enhance cutting, where appropriate. Any embodiment disclosed herein can be operated in a monopolar mode, or a bipolar mode, as desired, wherein the return electrode can be built into the catheter or an adjacent (e.g., pigtail) catheter to provide a return path for electrical flow.

Figure 7A:
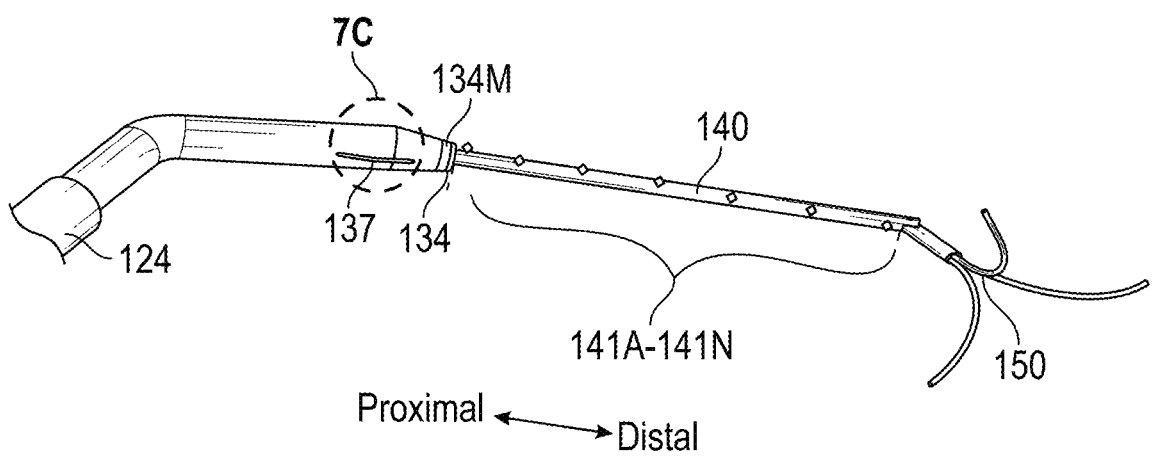
FIGS. 7A-7C illustrate still further aspects of the catheter-based system of FIG. 5 in accordance with some aspects of the present disclosure.
Figure 7B:
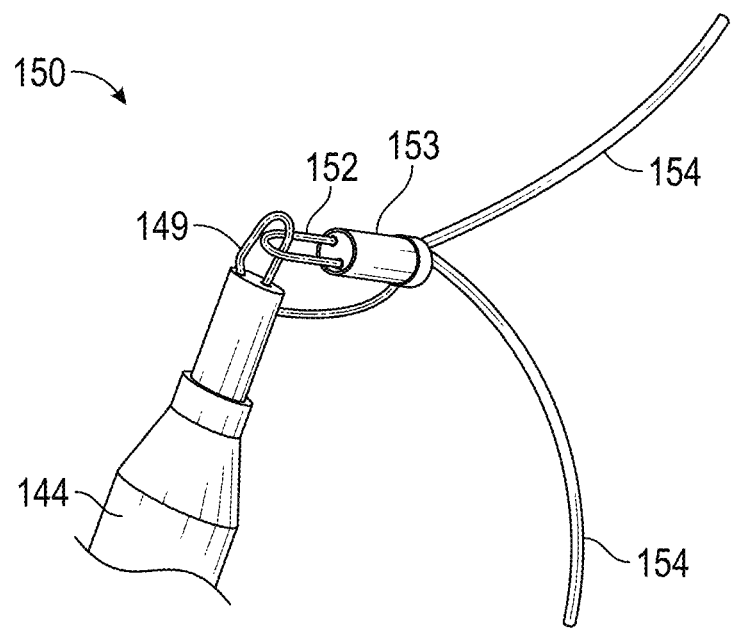
Figure 7C:
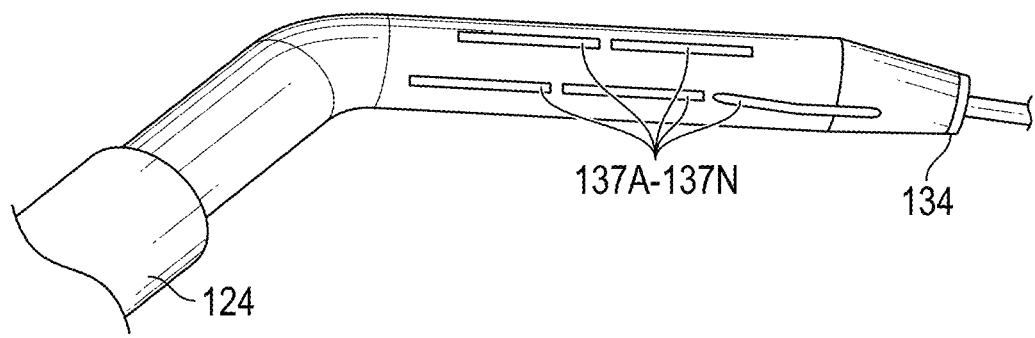

FIGS. 7A-7C illustrate still further aspects of the catheter-based system of FIG. 5 in accordance with some aspects of the present disclosure. For purposes of illustration, and not limitation, FIG. 7A illustrates a close-up view of a distal region of catheter 130 that protrudes from the distal end of intermediate catheter 120. FIG. 7B depicts a close-up view of the tissue anchor 150, and FIG. 7C illustrates placement of one or more electrodes 137 in the distal end region of catheter 130 for various purposes. Electrodes 137 are electrically coupled to one or more elongate conductors (not shown) that extend through the body 133 of catheter 130 to permit the conductors to be externalized from the patient to be coupled to diagnostic equipment and/or an electrosurgical supply.

FIG. 7A depicts a distal end region of the system 100, illustrating a distal end of catheter 120 from which a distal region of catheter 130 extends. As depicted, the catheter 130 can be a steerable catheter with active steering. The distal end 134 of catheter 130 can include a tapered region. One or more electrode(s) 137 can be present near the distal end of the catheter 130. The electrodes herein (e.g., 137, 137') can function as one or more of supply electrodes, return electrodes, and sensing electrodes. Rail 140 can define a plurality of markers 141 along the length of rail 140 in the region of where tissue is to be measured and cut. Markers 141 can be used under visualization in situ to measure the distance of tissue to be cut. The starting point for the cut and the ending point for the cut can be noted by the user. In some implementations, the markers 141 can be configured as electrodes that can function as one or more of supply electrodes, return electrodes, and sensing electrodes. If desired, stops (not shown) can be placed proximate actuator/handle 136 to limit the proximal-distal range of the distal end region of catheter 130. This can be done to define the length travel of the electrode 137 as it cuts through tissue. A distal marker 134 can be provided at the distal end 134 of catheter 130 in order to optimize positioning of the distal end 134 of catheter 130.

Figure 14:
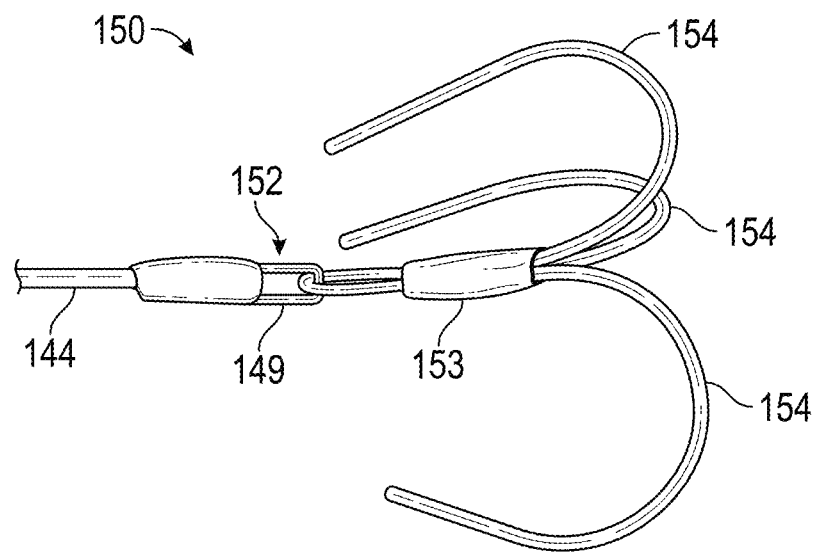
FIG. 14 is an illustrative implementation of an anchor in accordance with the present disclosure.

With reference to FIG. 7B and FIG. 14, the anchor 150 may include a pivoted coupling 152 that is pivotally coupled to a distal end 144 of the tether 140. As depicted, tether or rail 140 terminates at its distal end in a loop 149 that can be mated with loop 152 to provide a swiveling coupling to permit a large degree of rotational travel of the tether 140, particularly once the anchor 150 is anchored into tissue. The anchor can include one or more tines that can be anchored into tissue. Anchor 150 as depicted includes three tines 154. Anchor 150 is preferably formed from a shape memory material, such as a nickel-titanium alloy having shape memory formed therein such that the tines 154 of anchor 150 curl around to point proximally such that when tension is applied to the tether 140 inside a patient's heart, one or more of the tines 154 will be pulled into myocardial tissue, anchoring the anchor in place. In some implementations, anchor 150 can be made of a NiTi alloy, as indicated, and/or drawn filled tubing (DFT) that includes, for example, a NiTi alloy combined with a radiopaque material such as Platinum for visibility. Delivering the anchor 150 can be accomplished by pushing the anchor 150 to a target location confined within a distal end region of catheter 120. Catheter 130 can surround tether 140) and the distal end 134 of catheter 130 can push the anchor 150 out of the distal end of catheter 120 to deploy the anchor 150. Alternatively, anchor 150 can be withdrawn into the lumen 138 at the distal end of catheter 130 and be deployed, for example, by advancing a small profile push rod down lumen 138 to push anchor 150 out of catheter 130. Once unconstrained by the lumen 128 of catheter 120, the shape memory configuration of the anchor 150 can cause the anchor 150 to deploy. The swiveling or articulating coupling attaching the tether to the anchor can control direction of the tines 154. One or more markers 153 can be provided on the anchor near the pivot loop 152, and/or on the tines 154 to help inform a user when the anchor tines anchor in tissue under a visualization modality. The catheter 130 can be articulated to push into the myocardium such that pushing the anchor out of the catheter causes the anchor 150 to penetrate the myocardium and become anchored in the tissue. In accordance with further implementations, any anchor herein (e.g., 150, 350) can be formed in a flattened configuration. For example, rather than the three-dimensional hook implementation of FIG. 14, the tines can be formed from a planar material located adjacent widthwise with respect to each other along the planar material, and with one or more single direction hooks (with varying length and curvature) to make sure all hooks are embedded into tissue.

In some aspects, the disclosure provides sensing catheters, and/or sensing catheters that can perform additional operations such as cutting. For example, the disclosure provides implementations of a medical device having an elongate body having a proximal end and a distal end, and an elongate tether operably coupled to the elongate body. The elongate tether and elongate body are configured to be longitudinally displaceable with respect to one another. The device further includes an electrode disposed on at least one of the elongate body and elongate tether, and electrical circuitry operably coupled to the electrode, wherein the electrical circuitry is configured to determine a state of at least one of the medical device and the anatomical tissue.

In accordance with further aspects, the electrical circuitry, which can include one or more analog and/or digital circuit components, such as programmable processor programmed with machine readable code, which may be contained in a memory or other non-transient medium, can be configured or programmed to carry out the functions of the circuitry, wherein the term circuitry is intended to encompass analog and/or digital circuitry. In some implementations, the circuitry can detect an incoming signal from the anatomical tissue to confirm that the electrode (e.g., 137, 141) is in physical contact with the anatomical tissue. The incoming signal from the anatomical tissue can include an electrocardiogram signal from cardiac tissue. In further implementations, the electrical circuitry can be configured to detect a voltage or current drop across the electrode after electrical power has been applied to the electrode.

In some implementations, the electrode(s) can be configured to cut tissue when energized, and relative longitudinal movement of the elongate tether and the elongate body can cause the electrode to cut through anatomical tissue that the device is placed adjacent to when the electrode is energized. In such applications, if desired, the electrical circuitry can be configured to correlate the voltage or current drop with a physical state, such as (i) a state of tissue being cut by the electrode, and a state of fouling of the electrode. If desired, such a system may further include a one or more pressure sensors located proximate the electrode. The pressure sensor can be operably coupled to the circuitry, for example. The processor can be programmed, for example, to determine at least one biological parameter based on receiving a signal from the pressure sensor, such as blood pressure or other parameters. The pressure sensor can include any suitable pressure sensor, such as a fiber optic pressure sensor having a distal crystal configured to direct light out of the distal crystal. The characteristics (e.g., wavelength or frequency) of the reflected light can permit computation or estimation of a local fluid pressure. Such a fiber optic sensor may be slidably received within the system (e.g., 100) and may be deployed to a target location to measure local pressure. Such a blood pressure probe may have one or more visualization markers to facilitate visualization of the blood pressure sensor under an imaging modality such as fluoroscopy or MRI. In another implementation, a pressure tap (opening) can be located at a desired location (e.g., a side port or distal opening of a catheter) that is in communication with a passageway through the device (e.g., 100) to an external pressure sensor, wherein static pressure at a predetermined location (e.g., a side port or distal opening of a catheter) can be measured. A pressure sensor can be deployed to help a user understand if a catheter is located distally beyond the aortic valve and is within the left ventricle of a patient. Such a sensor can also help a user appreciate whether or not an electrode is proximal a node, such as the SA or AV node, to avoid inadvertently delivering electrical current to a node.

With reference to FIG. 7C, the electrode(s) can be retractable into a further lumen defined in the tubular member 133 (not shown) or can be fixed in place. Such electrodes 137 can be distributed about part or all of the circumference of the distal end region of catheter 130. Moreover, instead of a cutting electrode, a blade can be provided that can be fixed on the surface of catheter 130 that can be retracted into the distal end of catheter 120. If a blade is provided, it can further be retractable into catheter 130. The cutter can thus include, for example, a cutting electrode, a blade, a cutting wire such as a diamond wire, a wire with a cutting implement coupled to the cutting wire, a narrow gage metallic wire, and the like. The electrode(s) can sit proud of the surface of catheter 130 (e.g., protrude slightly when unconstrained) but can flex down to surface height to reduce profile when being delivered through the lumen 128 of catheter 120. One or more electrodes 137A-137N can be provided along the length of and/or about the periphery of tubular member 133. The electrodes herein (e.g., 137A-137N) can function as one or more of supply electrodes, return electrodes, and sensing electrodes. If used as cutting electrodes, the electrodes 137A-137N can be fired at different times or simultaneously, as desired. For example, a first row of electrodes can function as supply electrodes, and a second row of electrodes can function as return electrodes. Tissue disposed between the supply and return electrodes of FIG. 7C, as well as in any other bipolar arrangement disclosed herein, can function as a conductive medium to complete the circuit. Some electrodes can be dedicated for cutting, and some of the electrodes can be dedicated for other purposes, such as sensing electrical properties of tissue, such as myocardial tissue. For example, some electrodes can be provided that is an EKG sensing electrode. Moreover, one or more of the electrodes can have more than one state of operation. For example, one or more of the electrodes 137 can be configured to sense electrical signals or properties of the tissue they are adjacent when power is not applied to the electrode to cut tissue. Additionally, one or more of electrodes 137 can be supply electrodes that supply current, and one or more of electrodes 137 can be electrodes that return current to an electrosurgical generator. In a further implementation, the anchor 150) and/or markers can function as return electrodes as mentioned above. The system, if utilizing one or more electrosurgical cutting electrodes can operate in a monopolar state of operation, wherein the electrode(s) are supply electrodes, and the return path of the current to the electrosurgical generator is through the patient by way of a conductive pad attached to the patient. Alternatively, the system can operate in a bipolar mode of operation wherein one or more electrodes can be supply electrodes and one or more electrodes can be return electrodes such that the electricity only need to pass from a supply electrode to a return electrode to complete a circuit. Suitable electrical supply and return conductors can be provided extending through additional lumen(s) of catheter 130 or along a core conductor (not shown) of tether 140 for example that are externalized and operably coupled to an electrosurgical generator and/or diagnostic equipment, as desired.

Figure 8A:
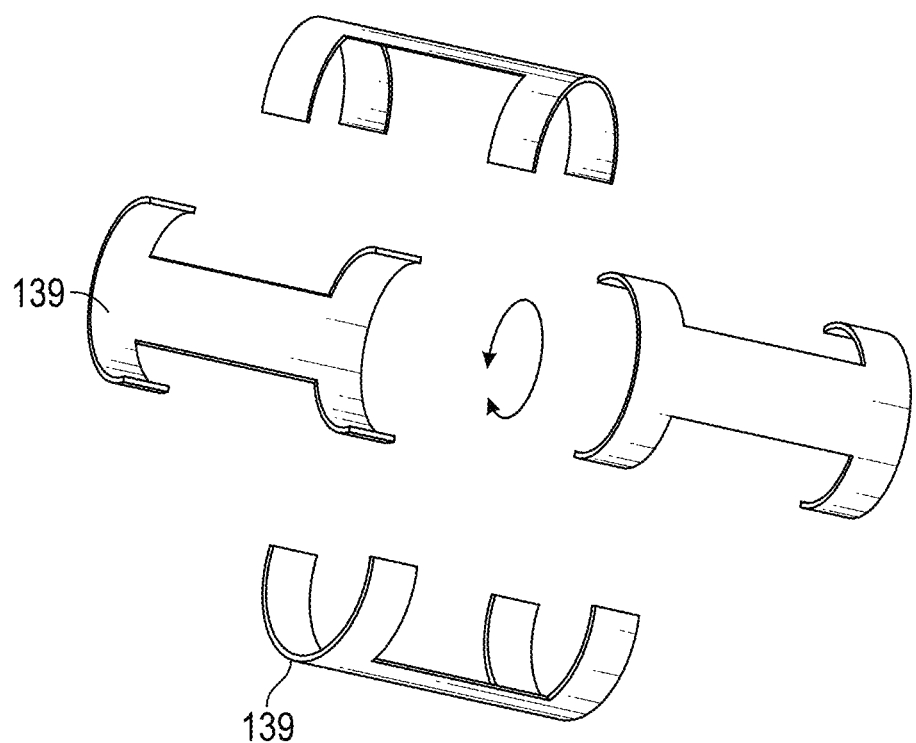
FIGS. 8A-8F illustrate features of the catheter-based system of FIG. 5 to confirm device orientation while performing a procedure in accordance with the present disclosure.
Figure 8B:
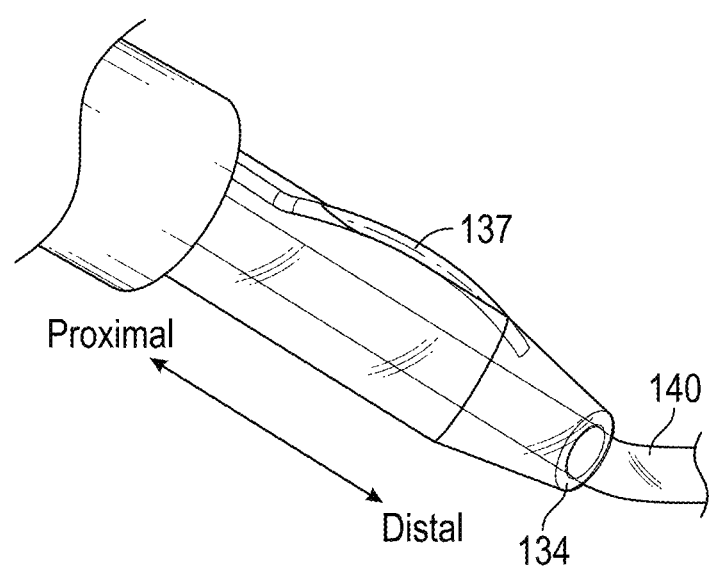

FIGS. 8A-8F illustrate features of the catheter-based system of FIG. 5 to confirm device axial and rotational orientation while performing a procedure in accordance with the present disclosure. FIG. 8A depicts a specially configured marker 139 that, when integrated into a catheter, permits a user to determine the rotational orientation of catheter 130. Moreover, an instrumentality, such as an electrode 137 and/or an exit port for a movable electrode can be positioned diametrically opposite of the marker 139. FIG. 8B depicts an implementation of a catheter 130 wherein a cutter, comprising a cutting electrode, or a blade, or an ultrasonic transducer or an ultrasonic element coupled to a cutting element 137 is provided in a distal end region of catheter 130. Where used, a cutting electrode may be coupled to an RF power supply operating in normal regimes, or microwave regimes that are less likely to interfere with the beating of the heart or the operation of cardiac nodes. An ultrasonic cutter provides advantages such as reduced tissue heating and not interfering with electrical operation of the heart, or ablation procedures. An ultrasonic transducer can be operably coupled to a cutting blade to effectuate cutting in accordance with any implementation of the present disclosure.

Figure 8C:
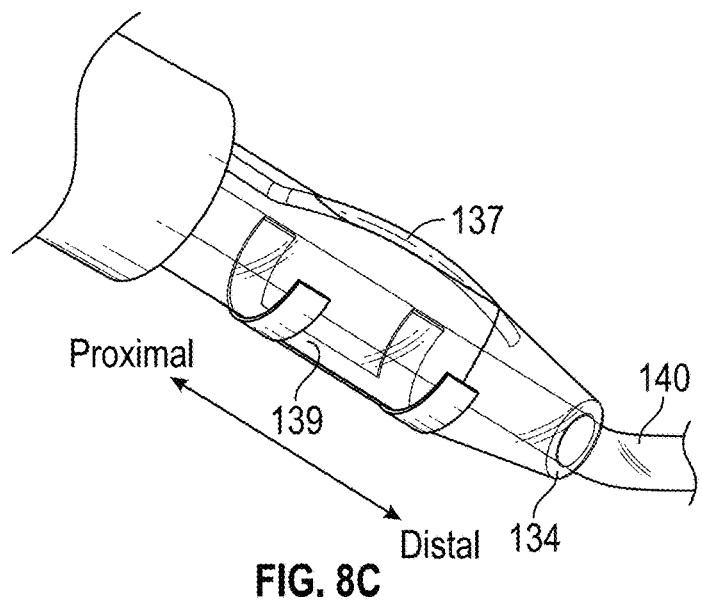
Figure 8D:
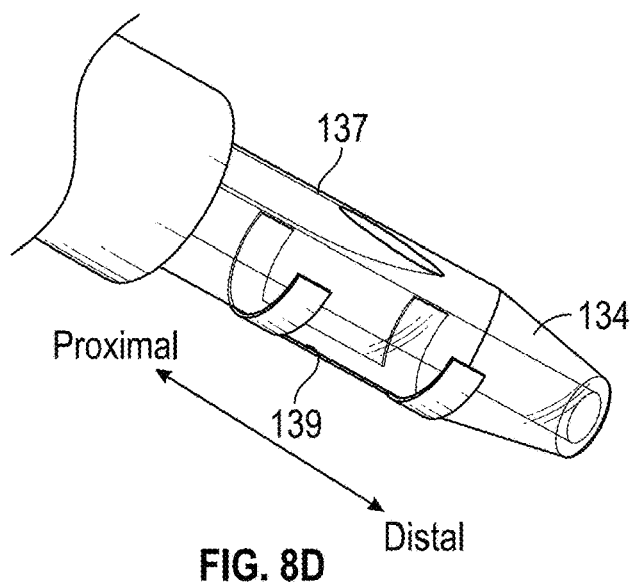
Figure 8E:
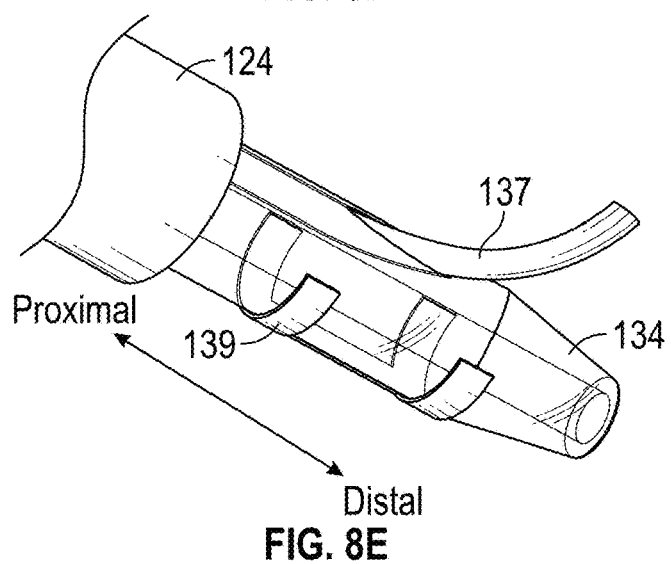
Figure 8F:
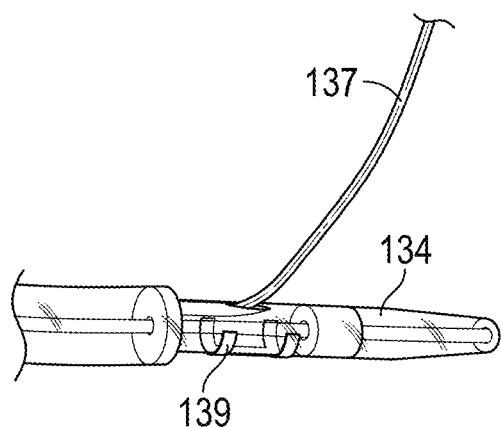

FIG. 8C depicts the implementation of FIG. 8B, but with marker 139 added. The marker 139 can also function as a return electrode for bipolar operation when attached to a current return line (not illustrated. The shape of the marker 139 includes an elongate spine section coupled to a midpoint of a "C" shape at each end of the spine, such that the "C" shaped portions wrap around a portion of the circumference of the catheter 130, above or beneath the surface of body 133. If the orientation of the marker 139 is known to the user to be diametrically opposite the electrode 137, the user can rotate the catheter 130 until the electrode is in contact with a surface to be cut. If the electrode 137 is configured to sense electrical activity in the tissue, the user can be informed that the electrode 137 is in electrical contact with myocardium, for example, if the electrode 137 conducts electrical signals from the myocardium to a signal detector or processor configured to detect such electrical signals. FIG. 8D depicts a deployable electrode 137 that is withdrawn into a lumen defined in body 133 of catheter 130. When the electrode is deployed as depicted in FIG. 8E, the location where the electrode exits is indicated by the location of marker 139. FIG. 8F is a view of the marker 139 under fluoroscopy demonstrating the electrode 137 being advanced out through a side opening of the catheter 130.

Figure 8G:
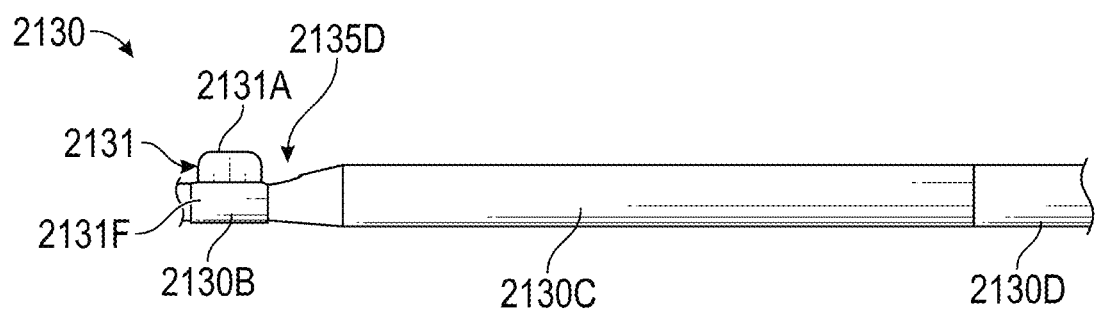
FIGS. 8G-8P depict aspects of a further implementation of a distal tip for the catheter-based system in accordance with the present disclosure, or aspects thereof.
Figure 8H:
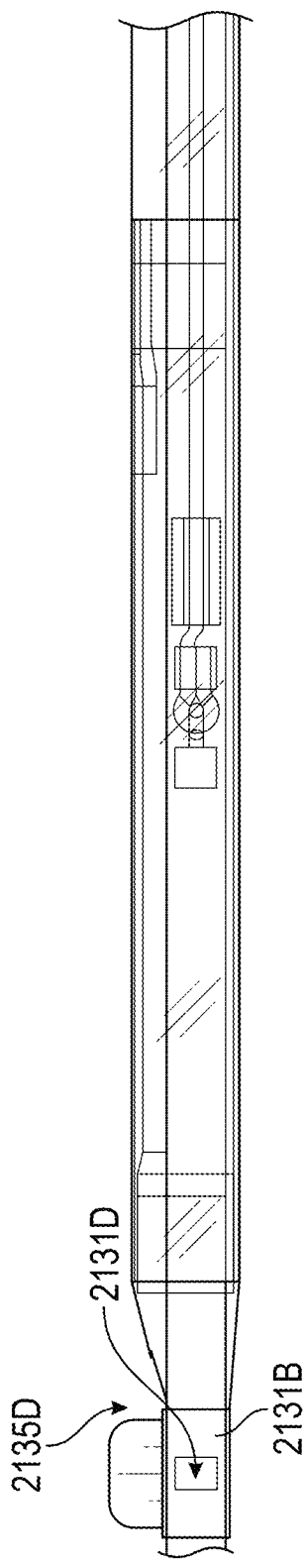
Figure 8I:
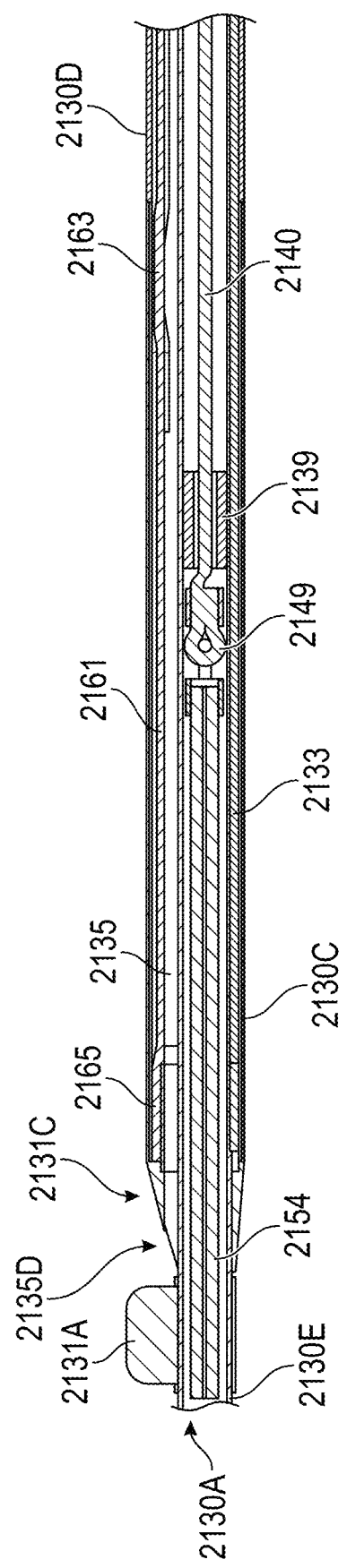
Figure 8J:
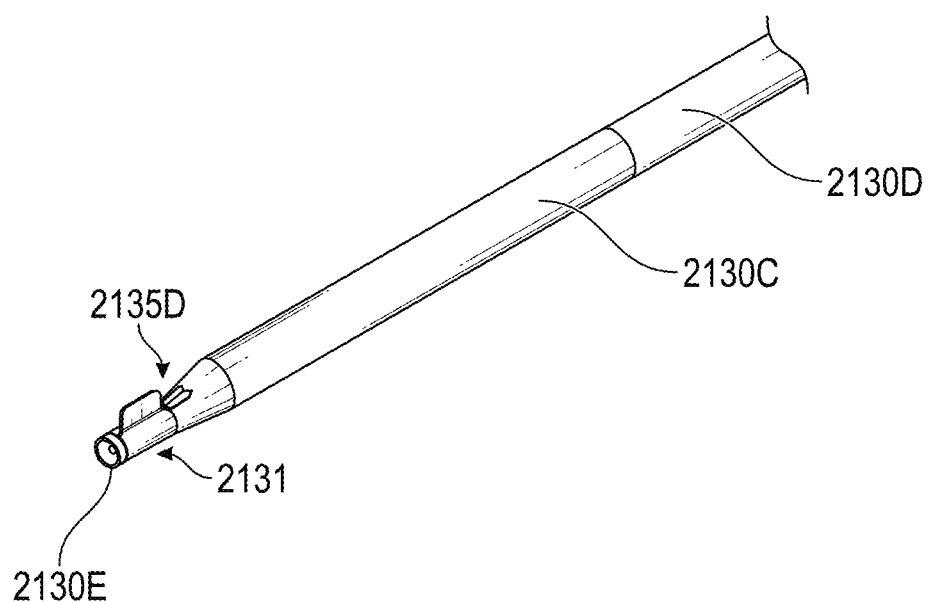
Figure 8K:
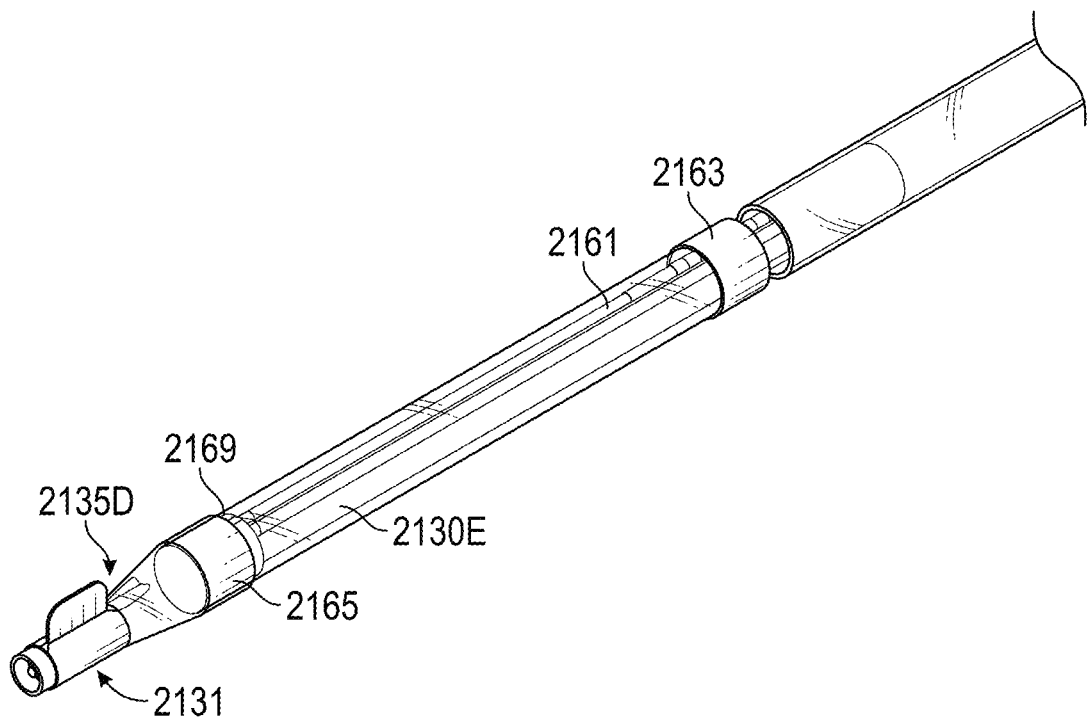

FIGS. 8G-8P depict aspects of a further implementation of a distal region of an inner catheter 2130 in accordance with the present disclosure that can be used in place of catheter 130 described above. FIG. 8G is a side view of the distal end region of the catheter 2130, FIG. 8I presents a cross-section of the distal end region of catheter 2130 down a vertical longitudinal centerline thereof and FIG. 8H presents a wireframe view of the distal end region of catheter 2130. FIG. 8J presents an isometric view of the distal end region of catheter 2130, whereas FIG. 8K presents the same view with a distal tubular covering 2130C removed to illustrate the relative location of interior components.

Catheter 2130 can be coupled at a proximal end thereof to a suitable actuator, including but not limited to those described elsewhere in this disclosure with reference to FIGS. 31-40D. The inner catheter 2130 is built around an inner tubular member 2130E that defines a lumen 2130A along at least a portion of its length (all or a part of its length). An electrode 2131 is concentrically positioned about and coupled to a distal end region of inner tubular member 2130E. The electrode 2131 is electrically coupled at a proximal end thereof to an electrical conductor, such as an electrically insulated or uninsulated elongate metallic member that extends proximally to a proximal end of catheter 2130 and operably coupled to an electrosurgical power supply (not shown). Inner tubular member 2130E may be partially or fully polymeric, or can include a braided layer of polymeric or metallic braids in a coextrusion with another material, and/or may include a polymeric or metallic coil, a lasercut hypotube to enhance flexibility, and the like.

The lumen 2130A can have an anchor 2150 and extension rod 2140 slidably disposed therein as with other implementations herein. As illustrated, proximal movement of the anchor 150 can be limited by a stop 2139 in the form of a boss, bump, protrusion, or as illustrated, a tubular member attached to an inner surface of tubular member 2130E through which rod 2140 is slidably disposed, or may be attached as a tubular member outside tubular member 2130E that applies an inward radial force to compress or restrict the inner diameter of tubular member 2130E. The catheter 2130 further includes a flush lumen 2135 that can be defined by a tubular member, for example that is disposed alongside and parallel to, or if desired concentric with, the tubular member 2130E. As depicted, the flush lumen 2135 is disposed diametrically displaced from, or opposite to, the conductor 2133 about the tubular member 2130E.

Figure 8L:
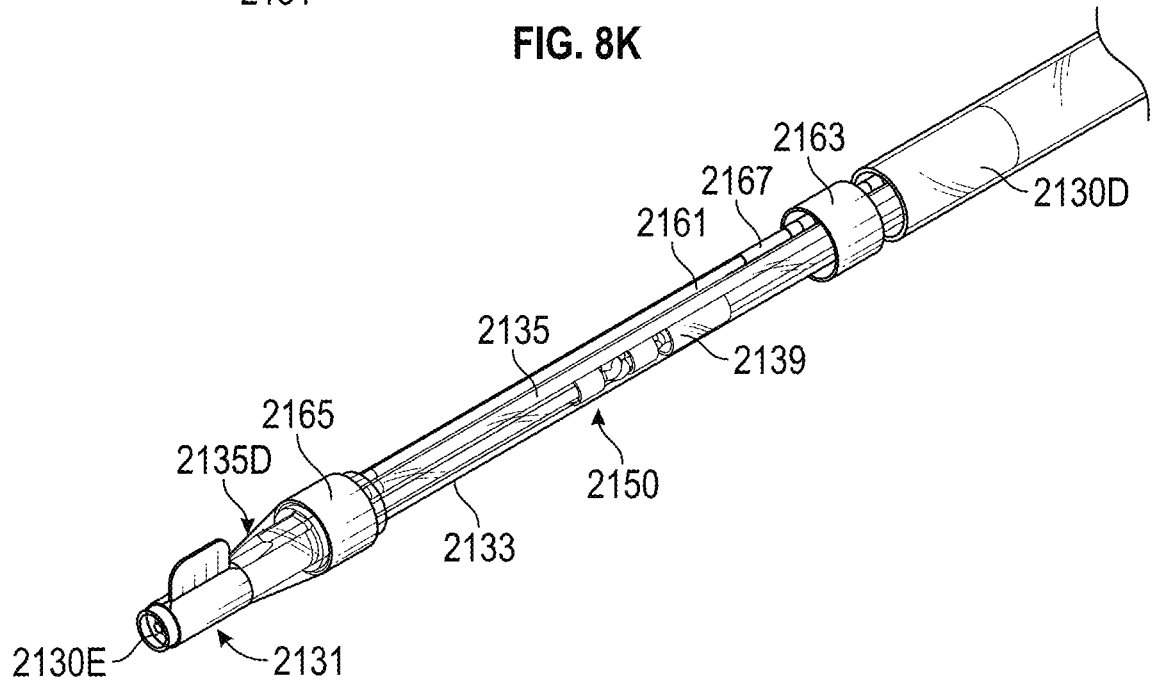

As further depicted, a pull wire 2161 is attached at a distal end thereof to a distal tip region of catheter 2130. As illustrated in FIG. 8L, the pull wire 2161 is attached, such as via welding, adhesive, or crimping to a distal retainer, anchor band or crimp 2165 having a "C" shaped or circular cross section. Distal retainer 2165 is attached directly or indirectly to the distal region of tubular member 2130E. For example, a sleeve 2169 with a longitudinal slit may be provided wherein the slit accommodates lumen 2135 and steering wire 2161, but contacts an inner cylindrical surface of anchor 2165 and an outer surface of tubular member 2130E. Outer shaft 2130C can be made from braided or other suitable material to facilitate structural deflection.

The pull or steering wire 2161 extends proximally into a distal end of a tubular member 2167 that is in turn operably coupled to a proximal region of the catheter (in a location of the distal end region of the catheter proximal to the distal retainer 2165). As illustrated, a distal location of tubular member 2167 is attached to a retainer or anchor 2163 that can be (but need not be) in turn directly or indirectly coupled to tubular member 2130E. In this manner, when tension is applied to the pull wire 2161, the catheter tip deflects in the direction of the tension to help steer the distal end of catheter 2130 through tortuous anatomy. A distal tubular covering 2130C, which may be a continuation of a braided shaft 2130D having a radiopaque polymeric (e.g., PEBAX) outer jacket and liner surrounds components 2130E, 2133, 2135 and 2161 that transitions to a proximal tubular covering 2130D that preferably has a suitable durometer to complement surrounding anatomy and facilitate deflection of the distal region of the catheter under tension of the steering wire 2161.

Figure 8M:
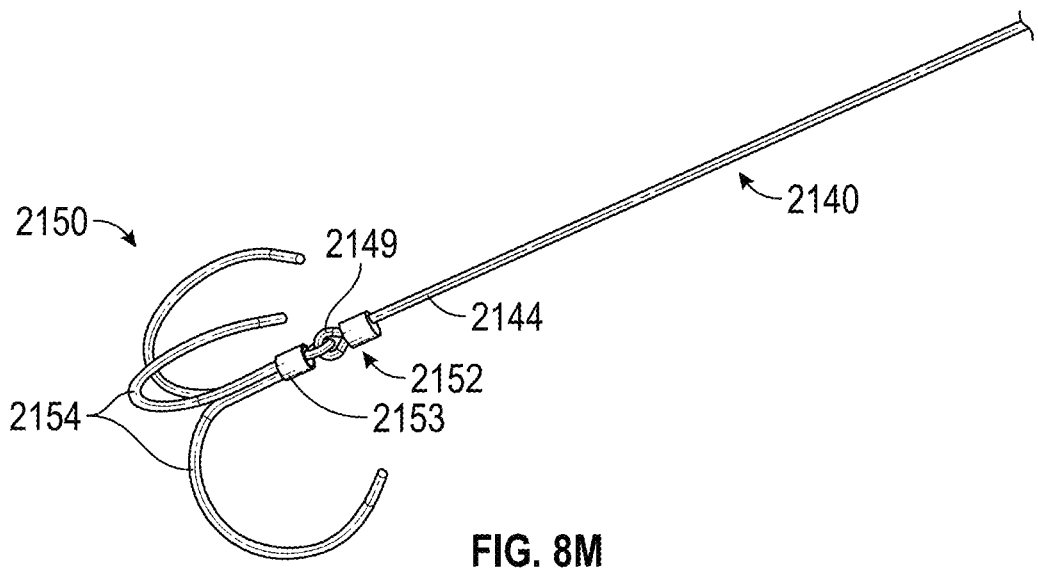
Figure 8N:
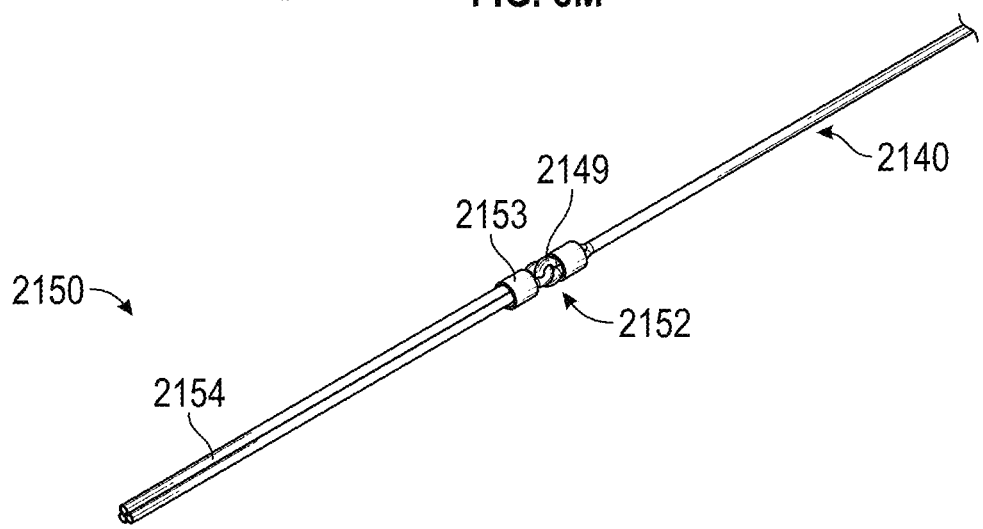
Figure 8O:
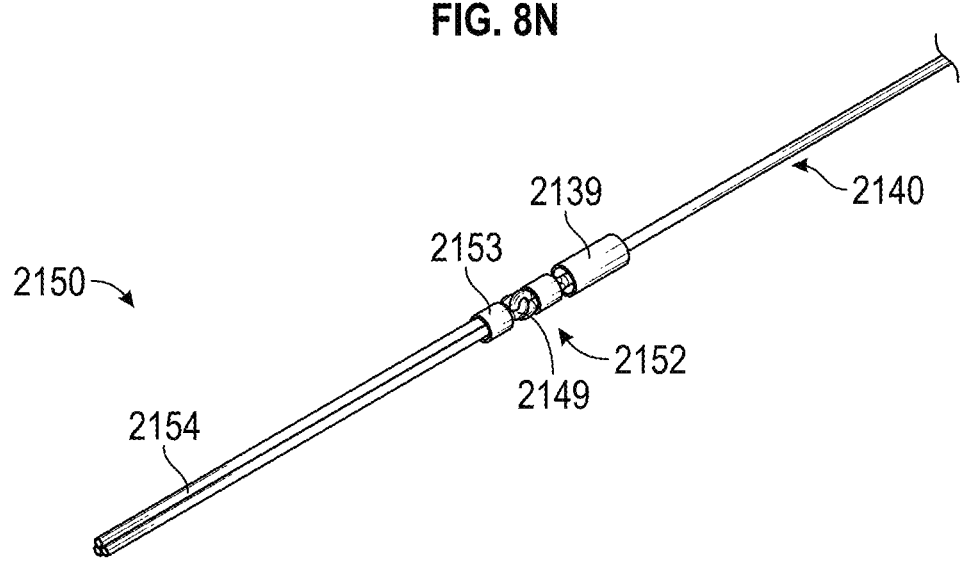
Figure 8P:
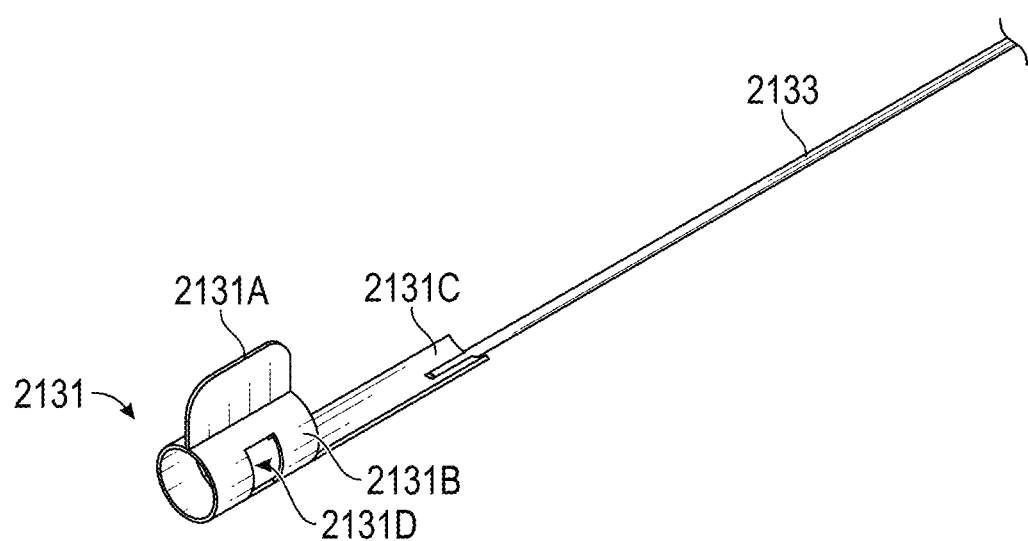

With reference to FIGS. 8P and 8L, the electrode 2131 is formed from a tubular section 2131B that surrounds the distal tip region of the tubular member 2130E. One or more windows 2131D can be defined through tubular section 2131 to provide additional contact perimeter for adhesive to facilitate coupling of the electrode 2131 to tubular member 2130E. Windows 2131D in combination with the dorsal fin 2131A and connecting structure, if formed from radiopaque material, or material that can be displayed on another imaging modality, such as MRI, can function as a three dimensional marker to help a user determine longitudinal, rotational and angular displacement and movement. In particular, windows 2131D can act as alignment holes such that when they are aligned with each other under visualization a user can conclude the orientation of the tip of the device with relative certainty. In addition, the overall shape of the structure can have a "P" shape further aiding in alignment.

Electrode 2131 further includes a proximally extending section 2131C that provides contact with conductor 2133 to facilitate electrical and structural attachment between the two components. The section 2131C can be a partial circumferential continuation of tubular section 2131B. Electrode 2131 further includes a dorsal fin 2131A that extends radially upwardly from tubular section 2131B and is oriented in a manner that is axially aligned with the exit port 2135D of the flush lumen. Electrode 2131 is preferably coated in a dielectric coating 2131F that surrounds tubular section 2131B and both planar sides of the dorsal fin 2131A, but that leaves some or all of the edge of dorsal fin 2131 A electrically exposed. In this manner, when the electrode 2131 is energized, the electrical charge is concentrated at this edge surface to provide more efficient distribution of electrical power, and also helps ensure that the electrically energized surface is within the flow stream of fluid exiting port 2135D. For example, a dextrose solution or other solution can be flushed through the flush lumen 2135 and over the fin 2131A of electrode 2131. This can keep blood cells away from the electrified surface when the electrode is energized and, in the case of dextrose or other non-conductive fluid concentrate electrical current to flow to tissue rather than fluid surrounding tissue, thereby reducing the chances of formation of thrombus and associated blood clots.

FIGS. 8M-8O more fully illustrate the anchor 2150 and pusher rod or tube 2140 that is slidably disposed in a distal end region of lumen 2130A. Anchor 2150 is similar in many regards to anchor 150 described elsewhere herein. FIGS. 8N and 8P illustrate the anchor tines 2154 in a constrained condition as when they are pulled proximally into lumen 2130A, and FIG. 8M illustrates the tines 2154 after deployment. The relative location of stop 2139 is indicated in FIG. 8O, with the understanding that the stop 2139 is coupled to the inner surface of tubular member 2130E within lumen 2130A.

Electrode 2131 can be a monopolar electrode and the system can include a return electrode as a separate catheter (or a standard return pad electrode located elsewhere) disposed near the cutting location to provide a return path for electric current. Alternatively, the catheter 2130 can be provided with one or more return electrodes (not shown) located near the electrode fin 2131A. For example, such a return electrode can be located on a dorsal surface of the catheter 2130, such as proximal to the exit port 2135D of the flush lumen 2135, or other suitable location.

Figure 9A:
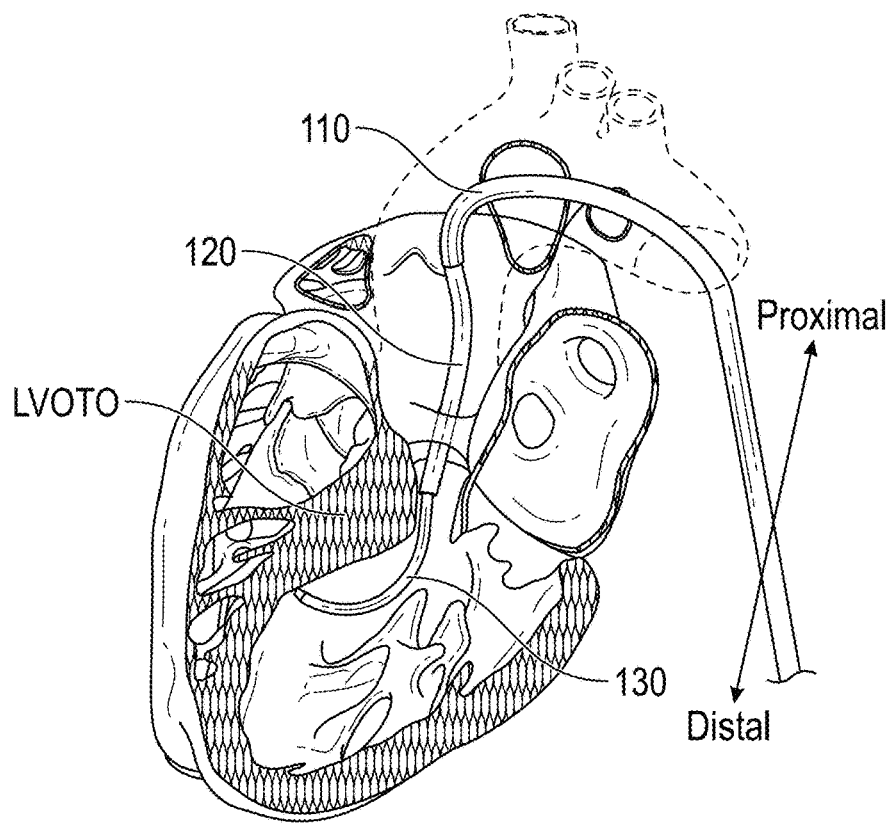
FIGS. 9A-12C illustrate aspects of a representative procedure to treat a LVOTO in accordance with some aspects of the present disclosure.
Figure 9B:
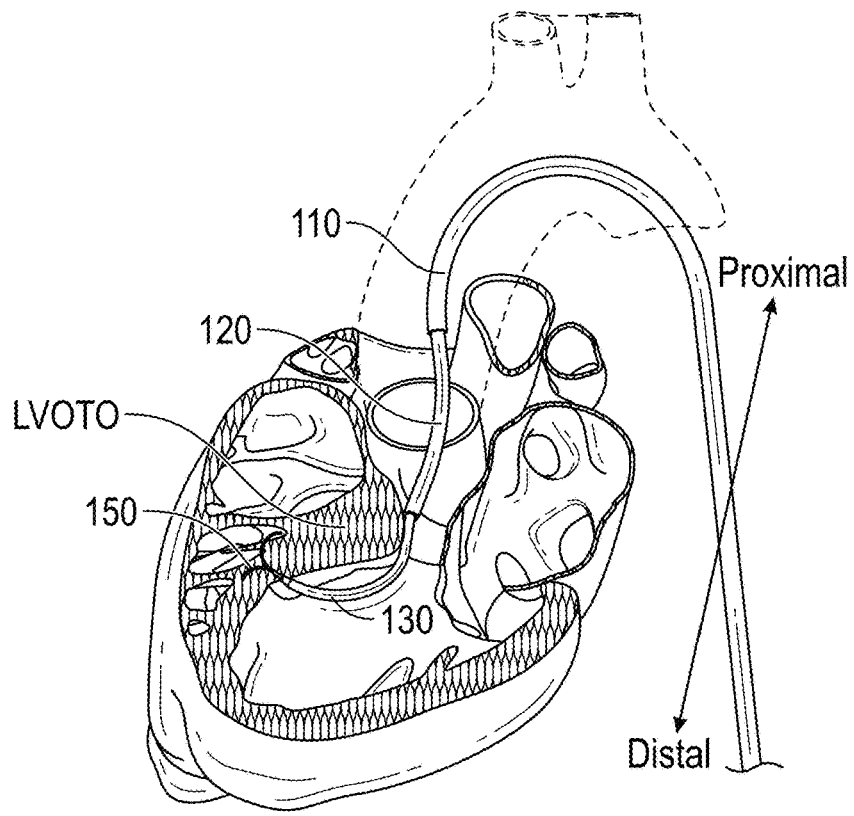
Figure 9C:
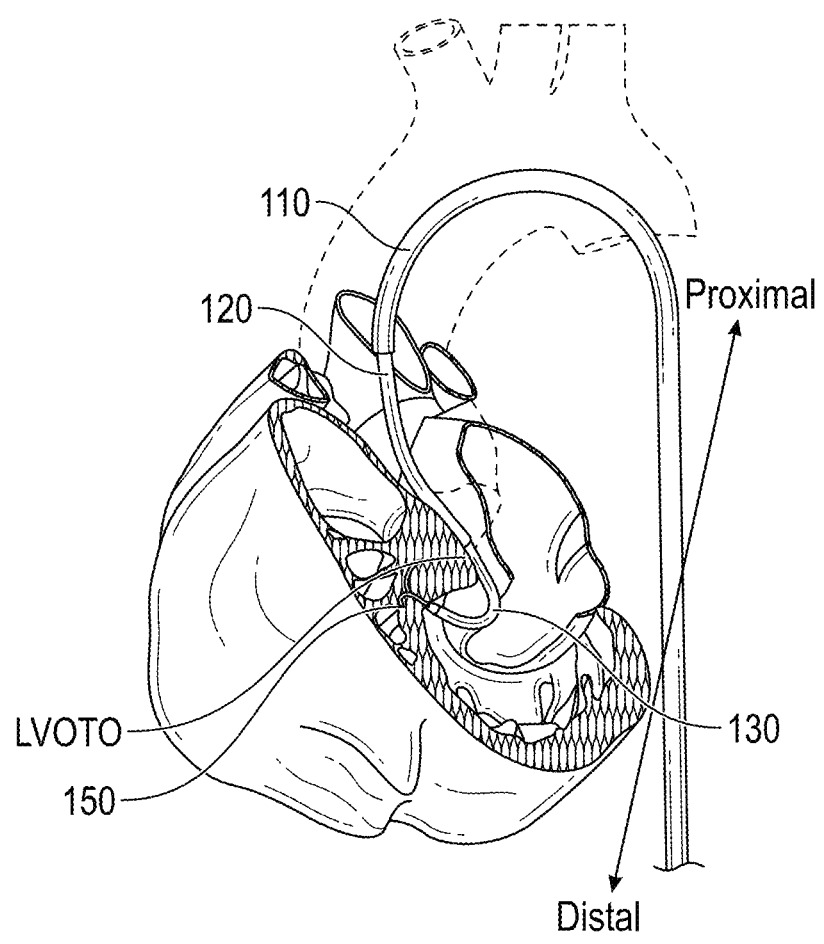
Figure 10A:
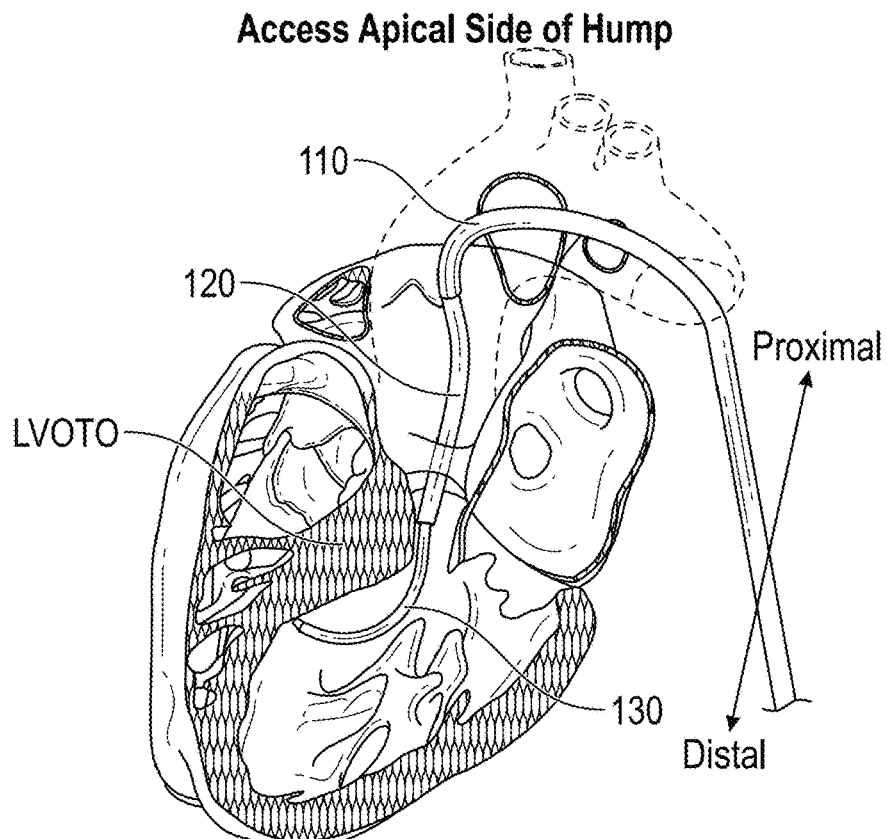
Figure 10B:
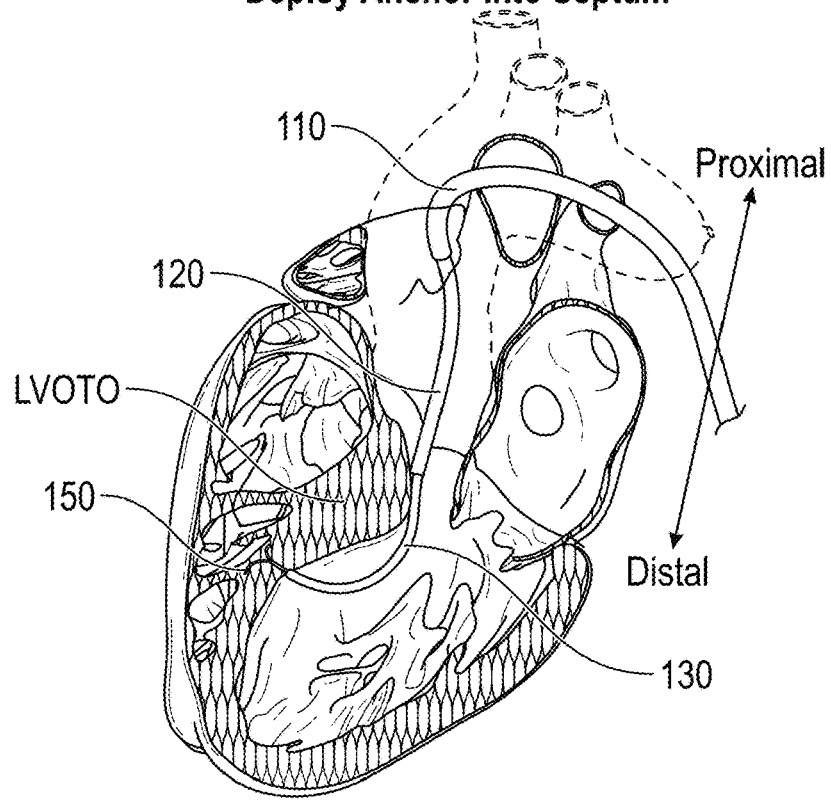
Figure 10C:
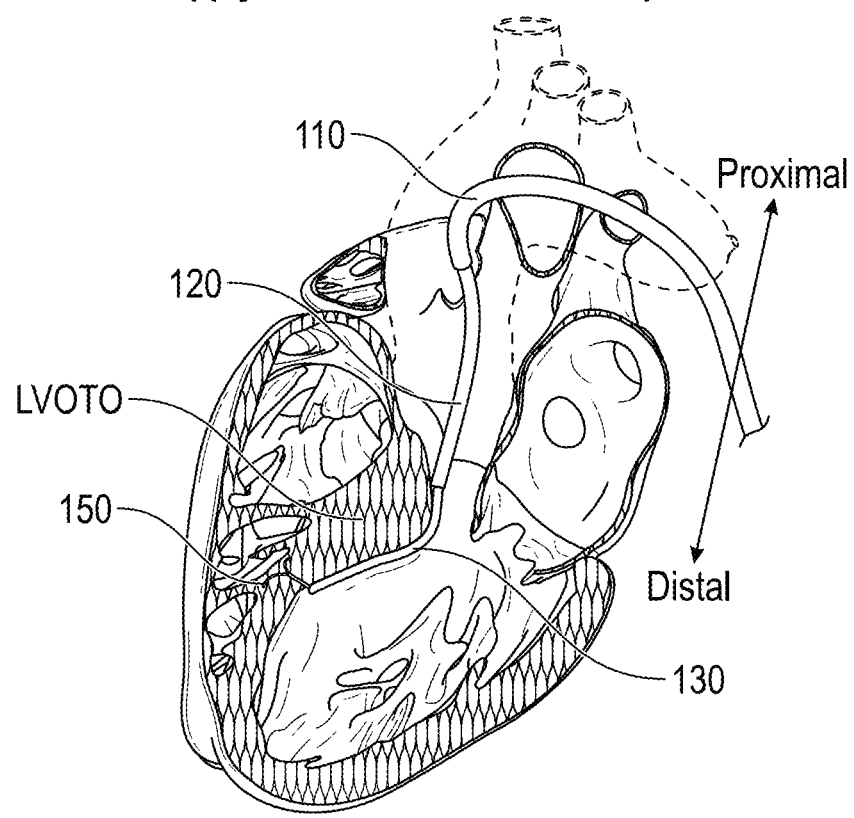

FIGS. 9A-12C illustrate aspects of a representative procedure to treat a LVOTO in accordance with some aspects of the present disclosure. For purposes of illustration, and not limitation, FIGS. 9A-9C depict the distal region of system 100 from different angles. As depicted, outermost catheter 120 deflects over the aortic arch to the ascending aorta. Catheter 120 facilitates deflection just under the valve alongside a base side of the left ventricular outflow tract obstruction ("LVOTO"). As depicted in FIGS. 10A-10B catheter 130 holds the distal end portion of catheter 130 bearing an electrode and anchor 150 and is deflected over the LVOTO in a controlled manner to deliver the anchor 150 to a location at the base of the distal end of the LVOTO toward the apex of the left ventricle. As depicted in FIG. 10C, tension is then applied to tether 140 and catheter 130 to conform catheter 130 to the shape of the obstruction.

Figure 11A:
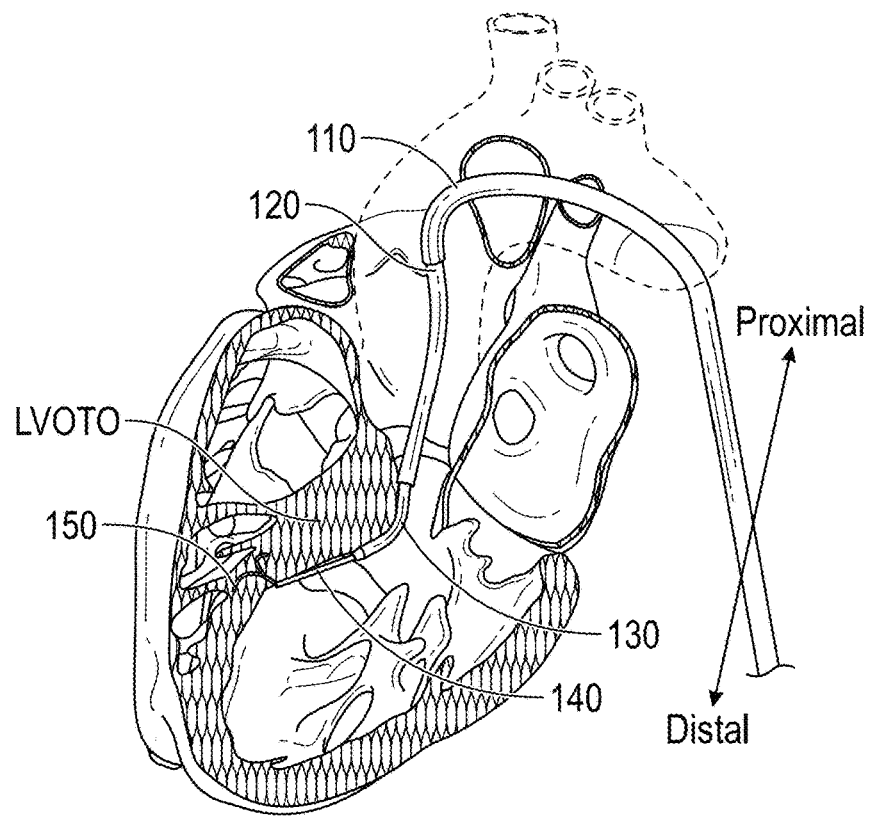
Figure 11B:
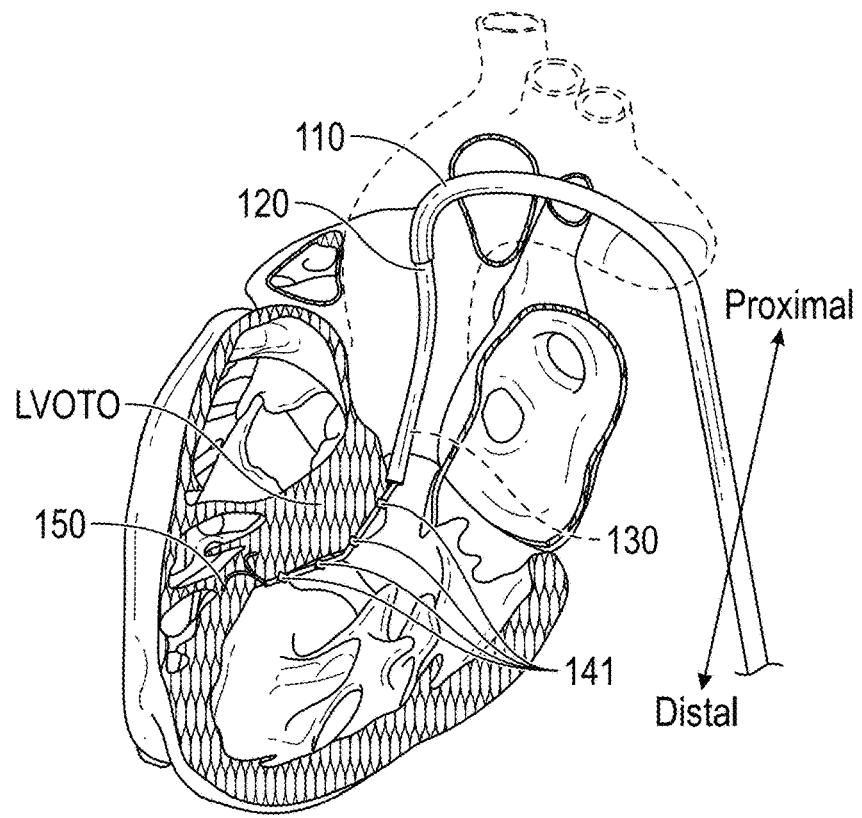
Figure 11C:
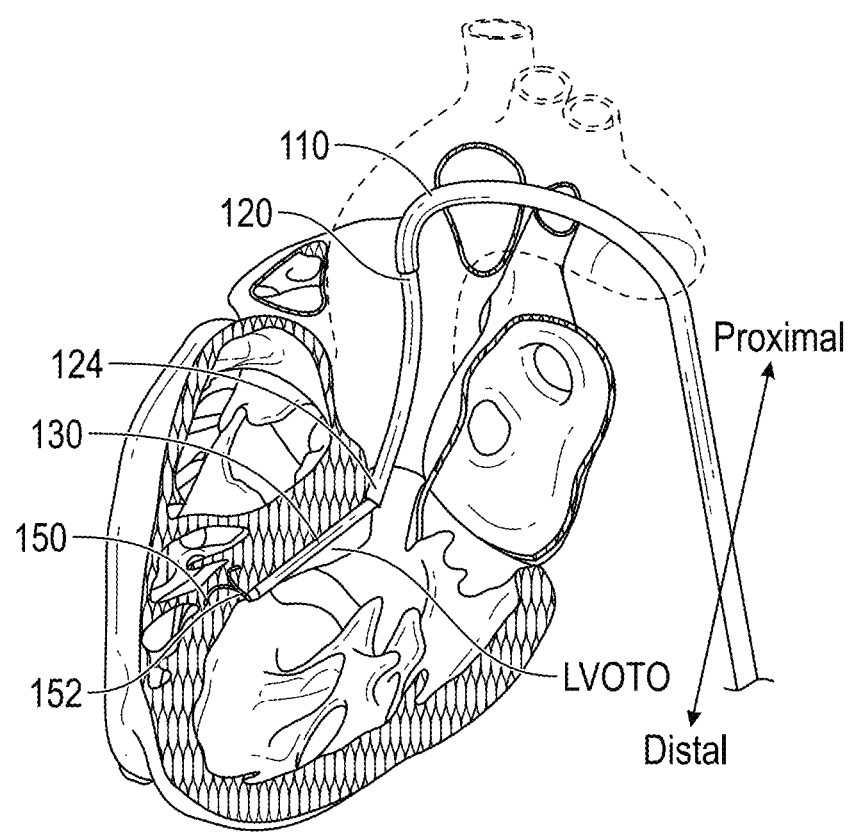
Figure 12A:
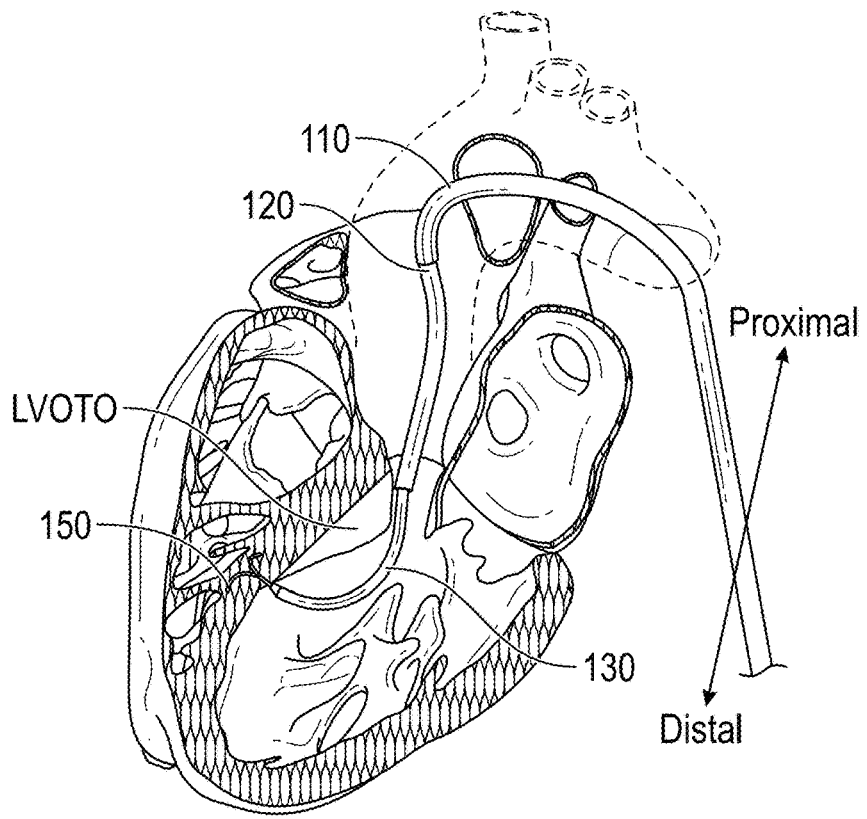
Figure 12B:
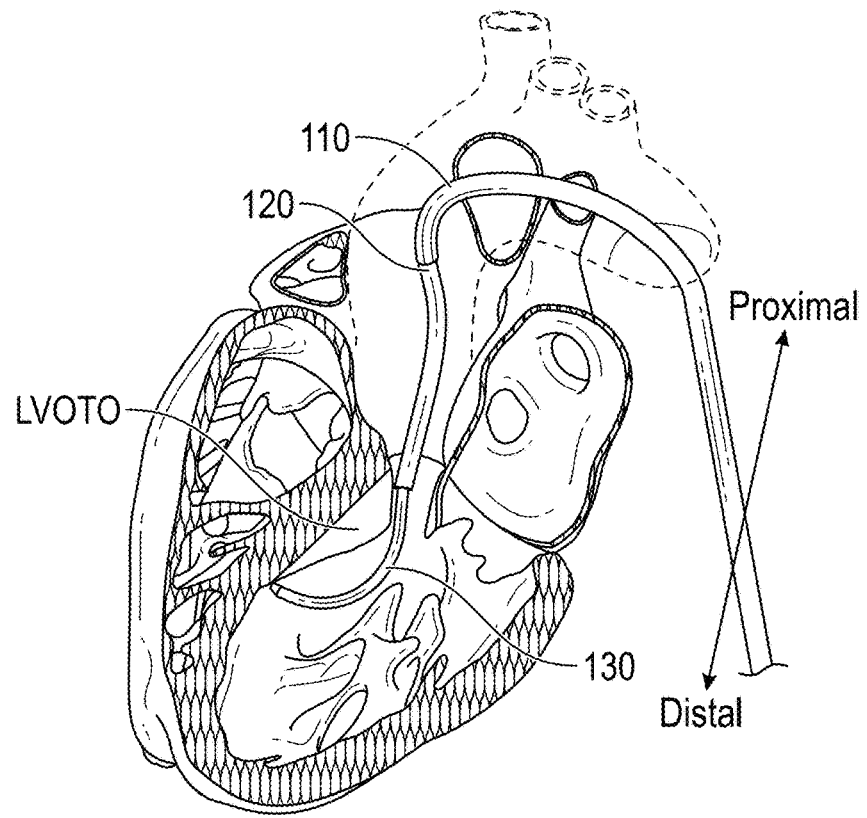
Figure 12C:
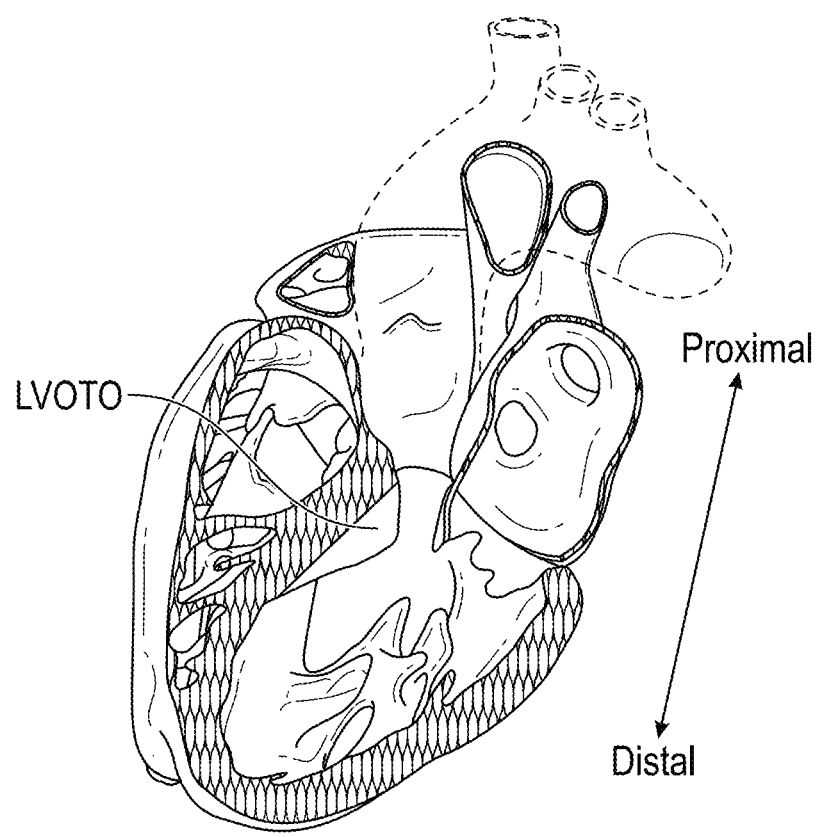
Figure 13A:
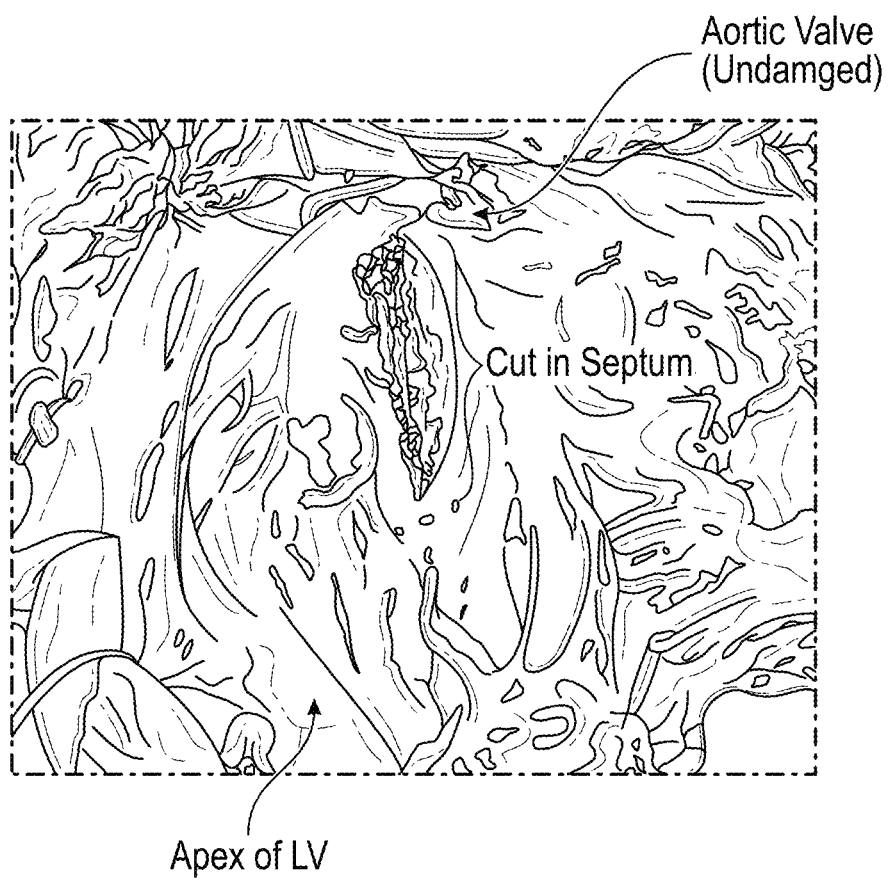
FIGS. 13A-13C illustrate results of an illustrative LVOTO treatment procedure in a porcine model in accordance with some aspects of the present disclosure.
Figure 13B:
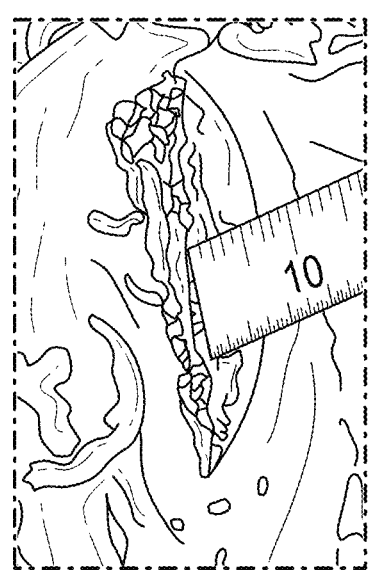
Figure 13C:
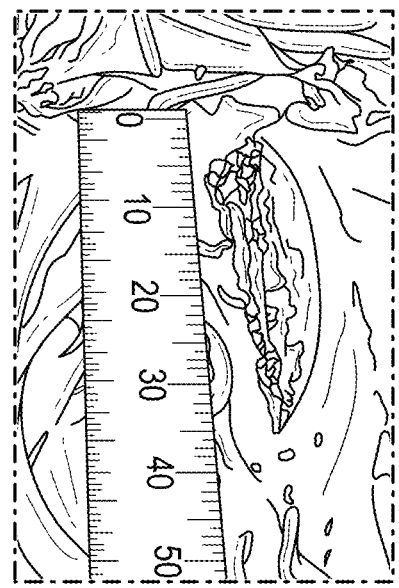

FIGS. 11A-11C depict aspects of a cutting operation in accordance with the present disclosure utilizing a reciprocating cutter. For purposes of illustration, and not limitation, the innermost catheter 130 is retracted proximally and advanced distally in a reciprocating manner while the electrode 137 is energized and in contact with the myocardium forming the obstruction. FIG. 11A depicts the innermost catheter when the distal end thereof bearing the cutting electrode (not shown) is about halfway along its reciprocating movement while traveling along tether rail 140. As depicted in FIG. 11B, markers 141 along the length of tether or rail 140 can be provided to permit a user to measure the cut length, and thus the linear travel that the actuator/handle 136 of the innermost catheter has to traverse along the proximal region of the tether 140. The linear range of motion of the actuator 136 or the carriage 230 can then be fixed, for example, by placing a clamp on either side of carriage 230 to prevent carriage 230 from moving proximally or distally by too great of an amount. The distal end of catheter 130, now functioning as a cutter due to electrode 137 being energized, reciprocated back and forth. With each movement, the electrode 137 burns further through the tissue of the obstruction until the cutter bottoms out along a line defined by the pathway of the tether between the anchor 150 and the distal end 124 of the intermediate catheter 120. The maximum depth of the cut is therefore controlled by placement of the distal end 124 of the intermediate catheter 120 and the pivot 152 of the anchor 150. FIG. 12A depicts advancing the innermost catheter 130 along a distal direction over tether/rail 140 to cause it to bow outwardly into the left ventricle until it contacts the anchor 150. The tether 140 is then withdrawn proximally into the distal end 134 of catheter 130 as depicted in FIG. 12B. The catheters 110, 120, and 130 may then be withdrawn proximally as indicated in FIG. 12C leaving behind the LVOTO which has been flayed with a cut, opening up the LVOT. If necessary, prior to removing the system 100, a second cut can be made through the LVOT that is substantially parallel to the first cut by realigning the anchor and redeploying the anchor, or by shifting the distal end 124 of the intermediate catheter 120. FIGS. 13A-13C illustrate results of an illustrative LVOTO treatment procedure in a porcine model in accordance with some aspects of the present disclosure. FIG. 13A depicts an elongate cut made in the obstruction by system 100. Also illustrated are the relative locations of the LV apex and the aortic valve, which is undamaged by the procedure. As depicted in FIG. 13B, the cut is over 5 mm deep. And, as depicted in FIG. 13C, the cut is nearly 40 mm long.

In further accordance with the disclosure, FIGS. 15-21B illustrate a further implementation of a tissue cutting system in accordance with the present disclosure.

Figure 15:
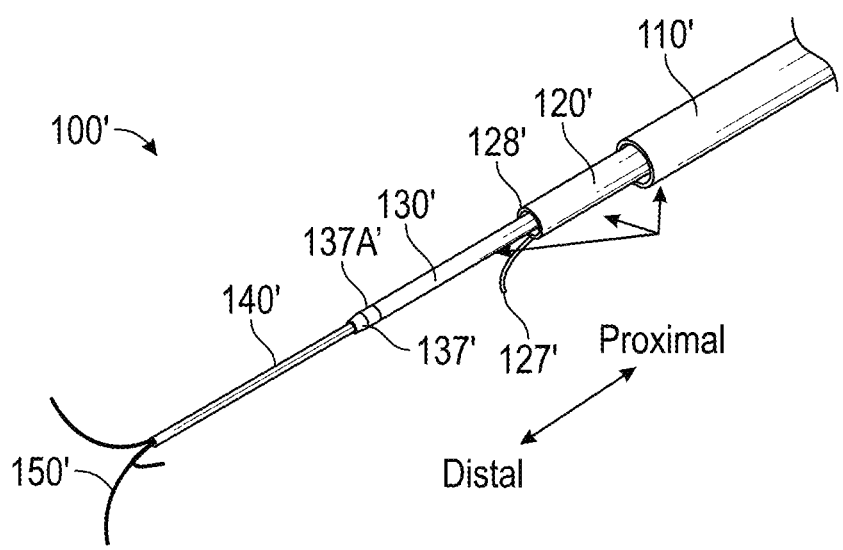
FIG. 15 is an illustration of a further system in accordance with the present disclosure for cutting tissue using a reciprocating cutter.

For purposes of illustration, and not limitation, FIG. 15 illustrates a multi-catheter system 100' wherein like reference numerals are directed to analogous system components as system 100 described above. System 100' is illustrated as having the same basic catheter arrangement as system 100, with an outermost catheter 110', an intermediate catheter 120' and an innermost catheter 130 that can be actively steerable as with implementation 100. While system 100 set forth above describes use of an inner tether or rail 140, system 100' instead includes an inner push tube 140' that extends along a passageway defined through catheter 130' that includes an anchor 150' disposed at a distal end thereof. System 100' can be made of similar materials and dimensions as system 100. The anchor 150' pivots at the distal end 144' of the push tube 140' to allow the push tube 140' to lay against and along myocardial tissue, such as the septum, as a guide rail in a manner similar to rail/tether 140 discussed with respect to implementation 100.

Innermost catheter 130' can include a ring-shaped electrode 137' that is configured to cut tissue to which it is adjacent when it is energized. One or more supplemental electrodes 137A' can be provided that can sense electrical parameters of myocardial tissue and/or act as a return path for electrical current to facilitate bipolar operation of system 100'. Similarly, push tube 140' or a conductor disposed therein (not shown) can serve as an electrically conductive return path to facilitate bipolar operation. The electrode 137' at the distal tip of catheter 130' may be of a fixed depth to cut a predetermined amount, or may be adjustable to permit the cutting depth to be adjusted. The electrode 137 may further be operably coupled to a hollow needle disposed within catheter 130 to permit access of a movable electrode or other wire.

System 100' can further be configured to permit a blood pressure reading to be taken from within lumen 128' of intermediate catheter 120' to confirm placement of the distal end of catheter 120 below the aortic valve of the patient. Moreover, with regard to any catheter system set forth in the present disclosure, a fluid channel can be provided to deliver a beneficial agent, such as a flush (e.g., a dextrose flush) to the area being treated. Such fluid can be delivered through the annular space defined between an inner wall of catheter 130' and an outer surface of push tube 140', as desired, or by another route or separate catheter.

With continuing reference to FIG. 15, the intermediate catheter 120' can further include a deployable anchor wire 127' to facilitate anchoring the distal end of catheter 120' in a desired location, such as at the base of the LVOTO. In some implementations, the anchor wire 127' can be deployed distally from a lumen defined in the distal end of catheter 120. In other implementations, the anchor wire can be deployed from a location of the innermost catheter 130. The anchor wire 127' can comprise a tubular member, such as a hypotube that can permit a guidewire or other wire, such as an electrode. In other implementations the anchor wire 127' can comprise a wire pigtail-like loop to sit in an aortic valve cusp.

Figure 16:
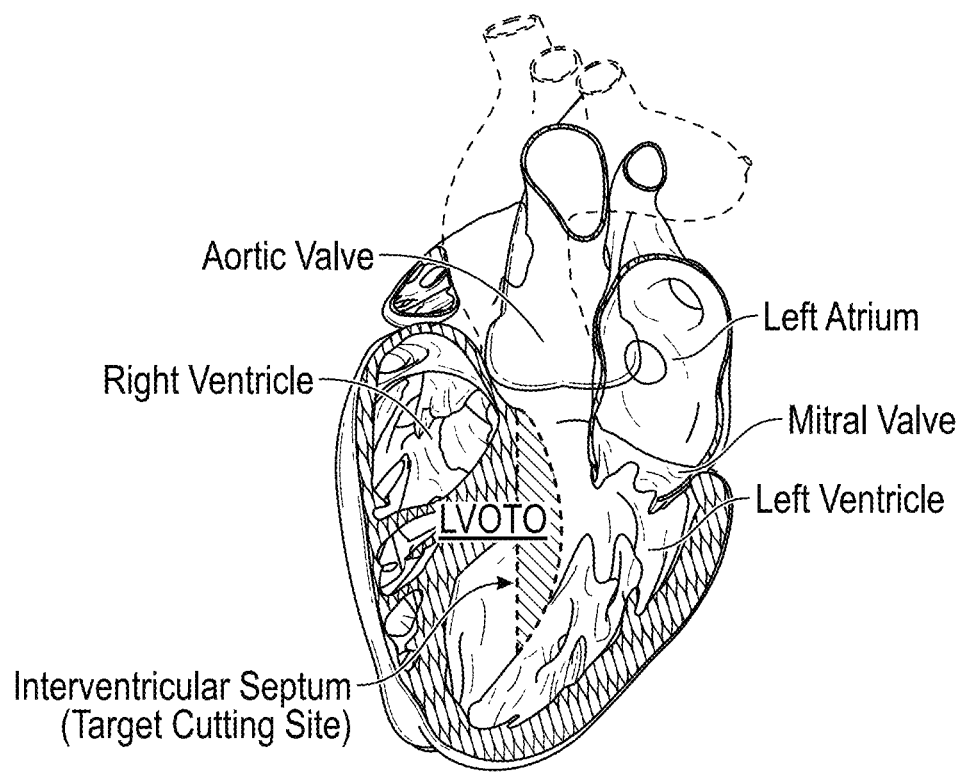
FIG. 16 is a schematic of anatomy of a heart illustrating a target cutting site for treating a LVOTO in accordance with the present disclosure.
Figure 17A:
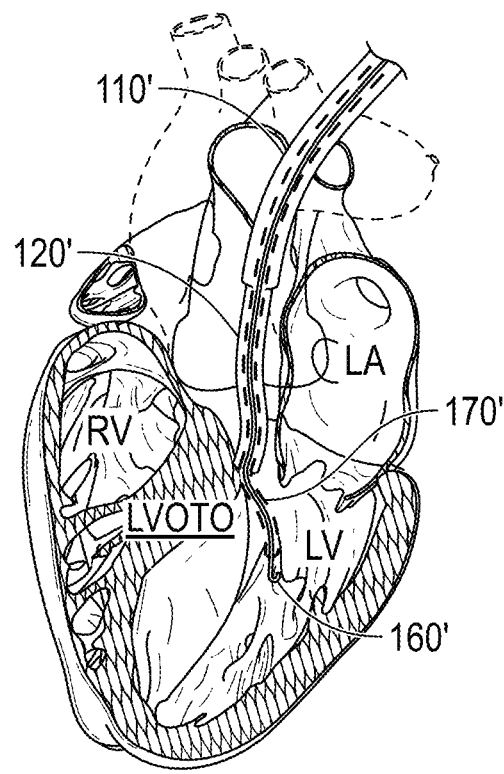
FIGS. 17A-17B are schematics illustrating aspects of introducing a system into a patient's heart to treat a LVOTO in accordance with the present disclosure.
Figure 17B:
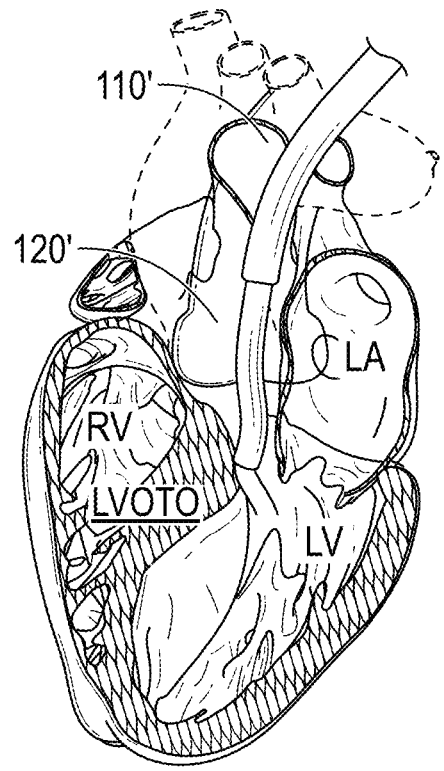

FIG. 16 is a schematic of anatomy of a heart illustrating a target cutting site for treating a LVOTO in accordance with the present disclosure. Specifically, the schematic illustrates a cross-section of the heart illustrating the relative locations of the left ventricle, right ventricle, left atrium, aortic valve, and LVOTO, indicating the boundaries of the LVOTO with respect to what would be considered a normal septal wall. FIGS. 17A-17B are schematics illustrating aspects of introducing a system into a patient's heart to treat a LVOTO in accordance with the present disclosure. Specifically, a guidewire 160' is introduced into the left ventricle (e.g., a 0.035-inch wire), and a dilator catheter 170' is introduced over guidewire 160'. Catheters 110' and 120' can then be introduced over the dilation catheter 170' to deliver the distal ends of catheter 110' proximal to the aortic valve, and catheter 120' proximate the tissue mass to be cut with the system 100'.

Figure 18A:
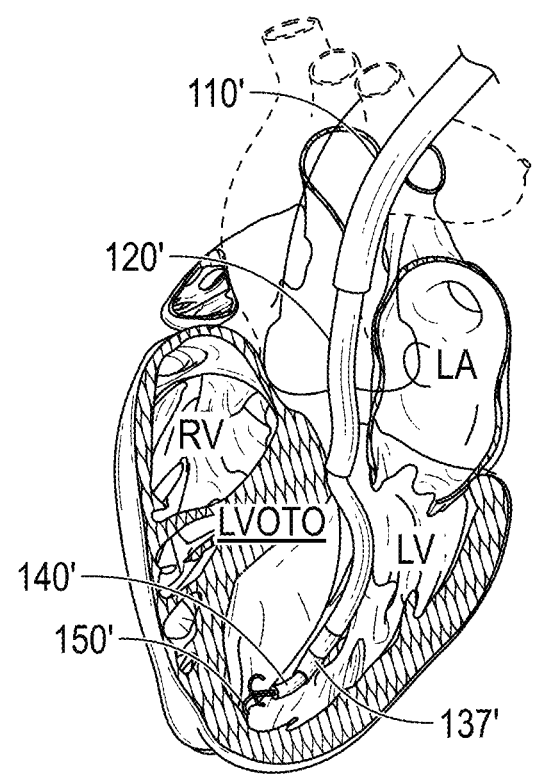
FIGS. 18A-18B are schematics illustrating further aspects of a technique to treat a LVOTO in accordance with the present disclosure including delivering an anchor to hold a treatment system in place within a patient's heart.
Figure 18B:
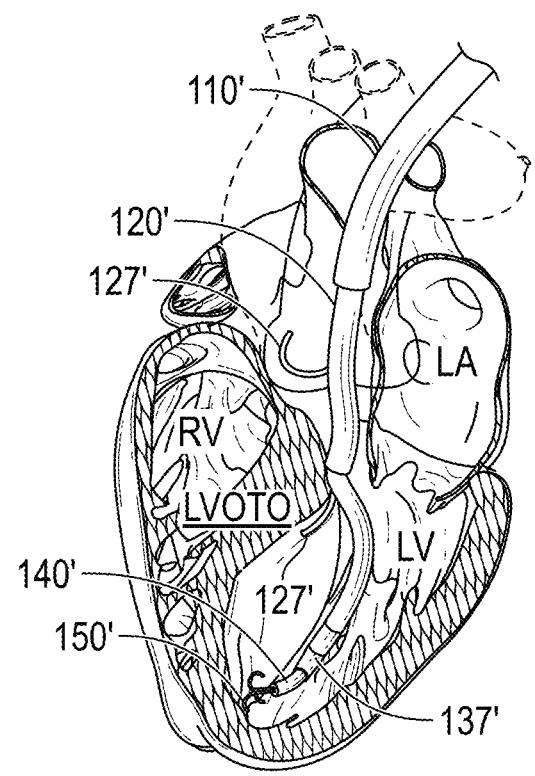

FIGS. 18A-18B are schematics illustrating further aspects of deployment of system 100'. FIG. 18A depicts anchor 150' deployed into the myocardium with the push tube 140' surrounded by the distal regions of catheters 130' and 120'. If needed, catheter 120' can be advanced to the site of the anchor 150' to support the deployment of the anchor 150'. FIG. 18B illustrates the system after the intermediate catheter 120 has been retracted proximally over the obstruction a location near the base of the obstruction at the proximal side of the obstruction, and indicating the deployment of the anchor 127' into the tissue of the mass. Also illustrated is an alternative placement of anchor 127 in the cusp of the aortic valve wherein the anchor 127' acts as a brake that pushes against the cusp of and that gets trapped to an extent in the aortic valve cusp.

Figure 19A:
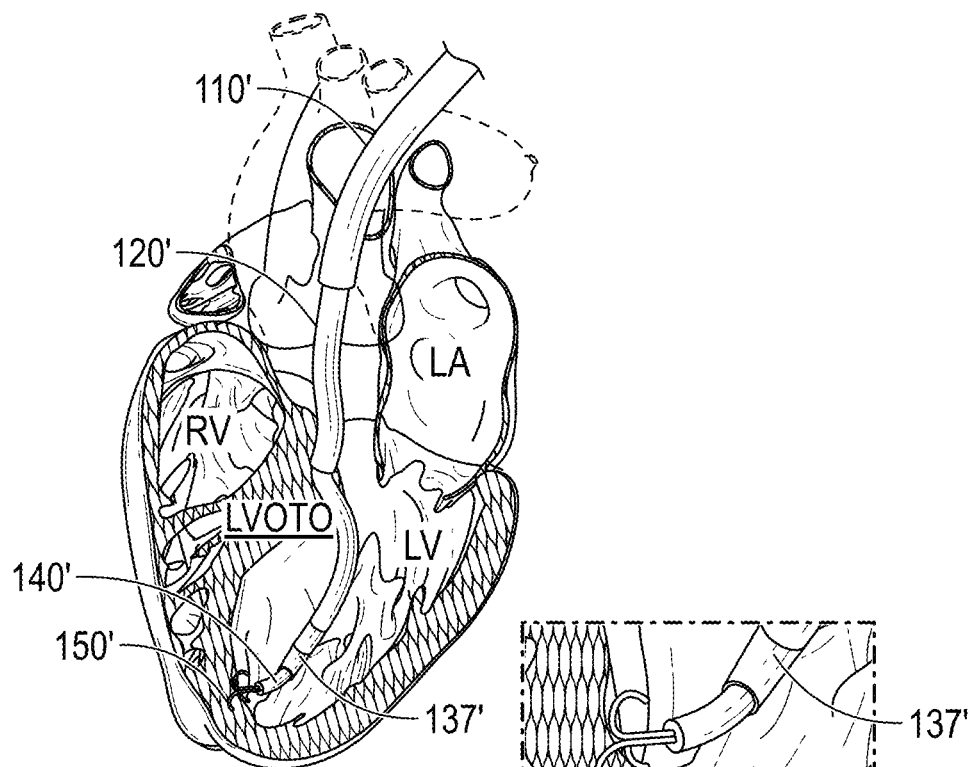
FIGS. 19A-19C are schematics illustrating further aspects of a technique to treat a LVOTO in accordance with the present disclosure including performing a cutting operation on the LVOTO using a reciprocating cutter.
Figure 19B:
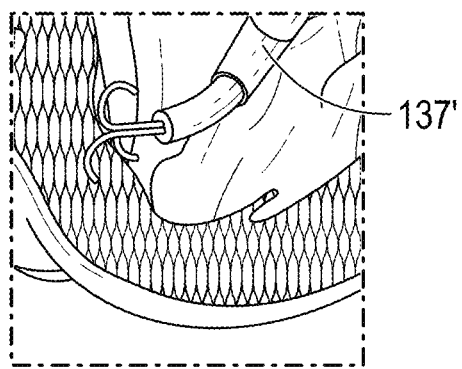
Figure 19C:
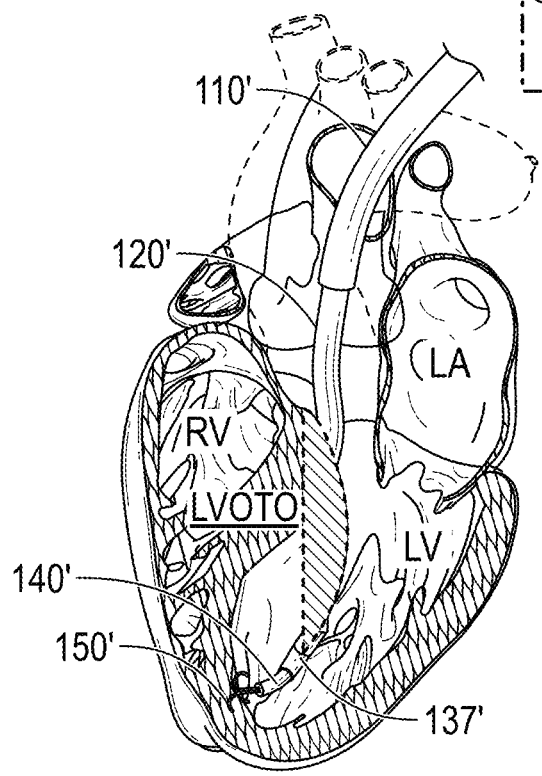

FIGS. 19A-19C are schematics illustrating further aspects of use of system 100' to treat a LVOTO in accordance with the present disclosure. FIG. 19A depicts deployment of a dynamic electrode 137' that may be advanced distally and radially outwardly with respect to the distal end of catheter 130. The catheter may alternatively be a fixed or static electrode 137' as indicated in FIG. 19B. As a dynamic electrode 137', the depth of the cut can be adjusted by advancing more or less of the electrode 137' from the catheter 130'. To complete a pass of cutting tissue, the catheter 130' is then withdrawn proximally over the push tube 140' which functions as a guide rail. One or a plurality of passes may be performed to cut the tissue multiple times along the same line of cutting to obtain a sufficiently deep cut to open the LVOT to an adequate degree.

Figure 20A:
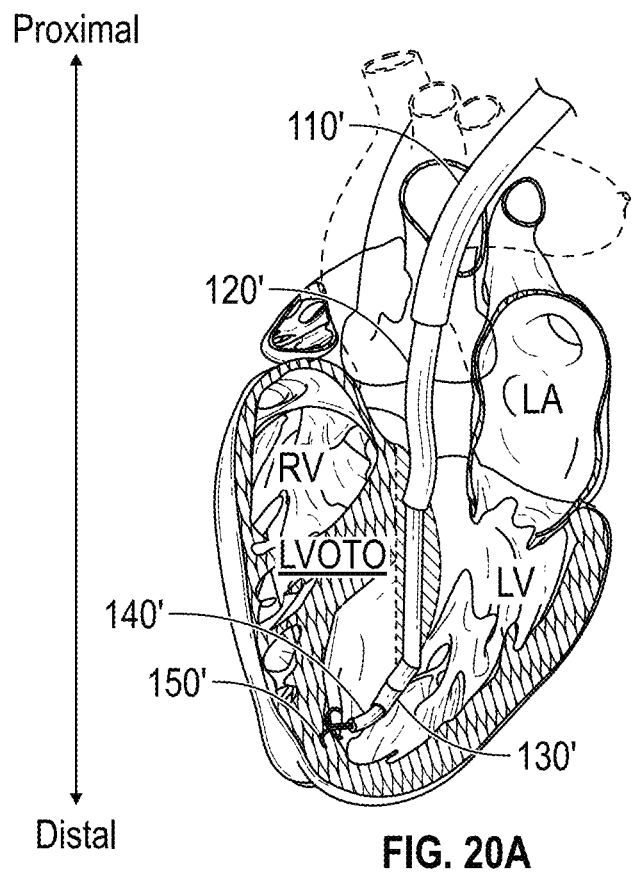
FIGS. 20A-20B are schematics illustrating further aspects of a technique to treat a LVOTO in accordance with the present disclosure including re-sheathing the cutter and retrieving the anchor of the system.
Figure 20B:
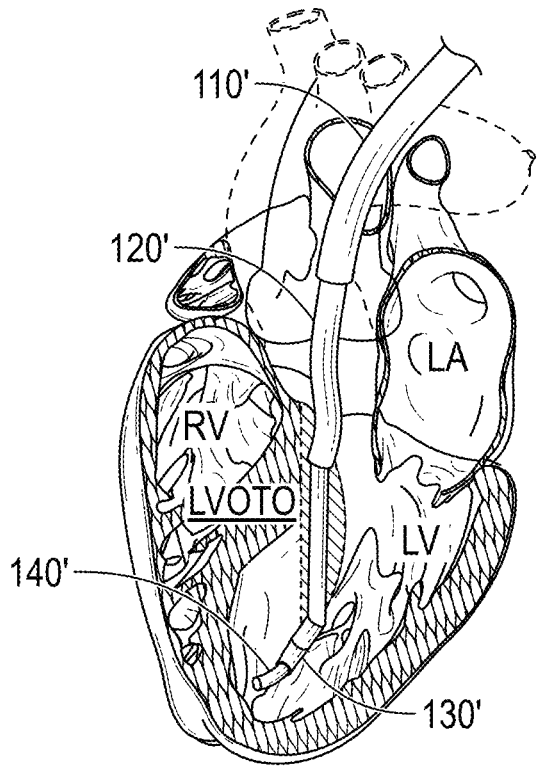
Figure 21A:
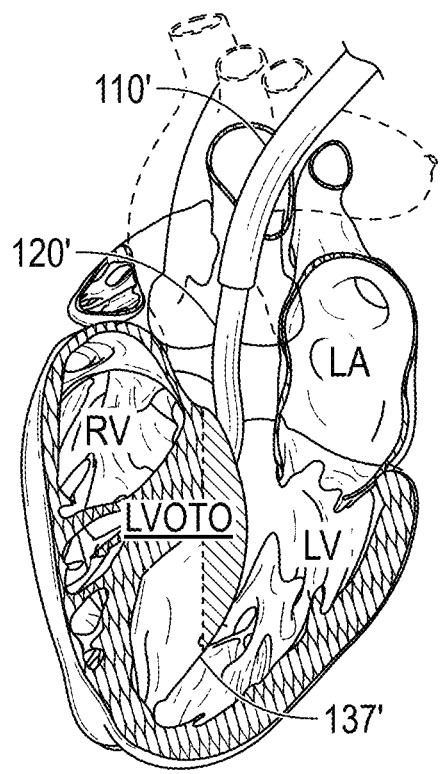
FIGS. 21A-21B are schematics illustrating further aspects of a technique to treat a LVOTO in accordance with the present disclosure including withdrawing the catheter-based system from the patient and illustrating the treated LVOTO.
Figure 21B:
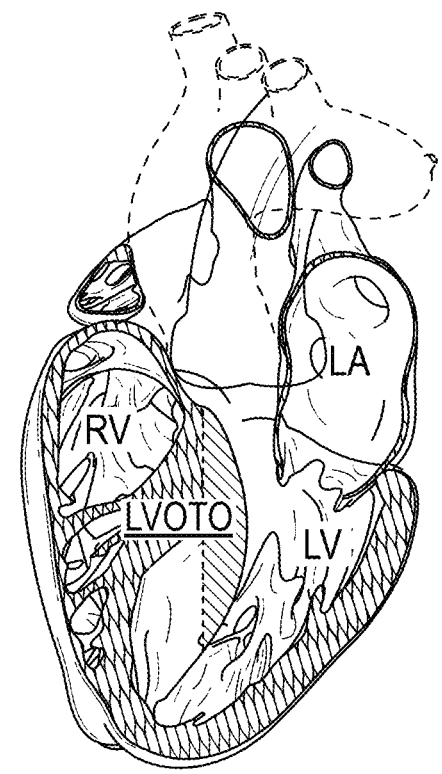

FIGS. 20A-20B are schematics illustrating further aspects of system 100' and its use to treat a LVOTO in accordance with the present disclosure including resheathing the cutter and retrieving the anchor of the system. FIG. 20A depicts the innermost catheter 130)' being advanced distally over push tube 140' to the location of anchor 150'. As illustrated in FIG. 20B, the push tube 140' is withdrawn into the distal end of catheter 130'. FIGS. 21A-21B depict withdrawing the catheter-based system from the patient and illustrating the treated LVOTO. FIG. 21A depicts the distal portion of the catheter system 100' as it is withdrawn from the patient's heart. FIG. 22 depicts the bottom of the cut through the LVOTO, which helps open a channel to enlarge the cross-sectional area of the LVOT. If it is desired to make the cut deeper, or to make a second cut in the tissue generally parallel to the first cut, the system 100' can be re-deployed into the left ventricle, the anchor 150' can be re-anchored in a laterally displaced location from the first site of deployment of anchor 150', and a second cut can be performed in a manner similar to the first cut.

FIGS. 22A-23C illustrate aspects of a further technique to treat a LVOTO in accordance with the present disclosure utilizing a further variation of a catheter-based system 100". System 100" incudes an inner rod or tubular member 140" that forms a main body of the system about which other system components are arranged concentrically. An intermediate anchoring catheter 120" is slidably disposed about member 140" to permit catheter 120" to slide proximally and distally over member 140". A second, distal catheter 180" is disposed distally of catheter 120" and also disposed slidably about member 140". In embodiment 100", the catheter system 100" is anchored in place at the distal base of the obstruction (e.g., an LVOTO) to hold the system in place to perform a cut along the obstruction at a location that is proximal to the anchor. As illustrated, the system 100" is deployed into the left ventricle, wherein the distal catheter 180 is advanced distally past the obstruction toward the apex of the left ventricle. The distal end region of the catheter 120" is advanced to the base of the obstruction, and an anchor wire exit port is "aimed" at the distal base of the obstruction. An anchor wire 127" is similar to anchor wire 127' can be advanced proximally into the distal base portion of the obstruction and pulled proximally into the tissue mass. In the implementation of FIGS. 22A-22C, this is effectuated by pulling outer catheter 180" proximally, which is attached to the anchor wire 127". This pushes the anchor wire 127" proximally into the tissue mass. At this point in the procedure, catheters 120" and 180" are maintained in position by the anchor wire 127". This permits tension to be applied to the system to push the catheter system against the tissue mass.

Figure 23C:
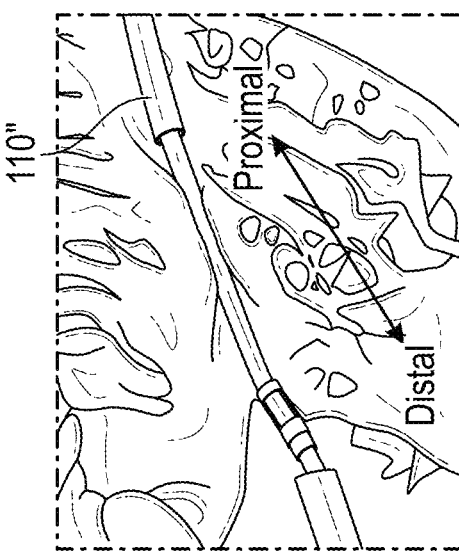
FIGS. 23A-23C illustrate aspects of yet a further method and system to cut tissue in accordance with the present disclosure utilizing a deflectable cutting catheter.
Figure 23B:
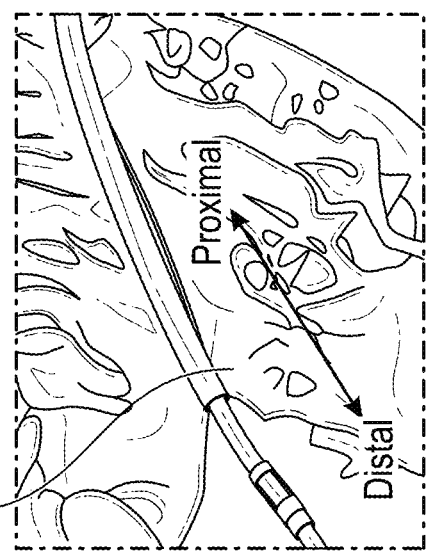
Figure 23A:
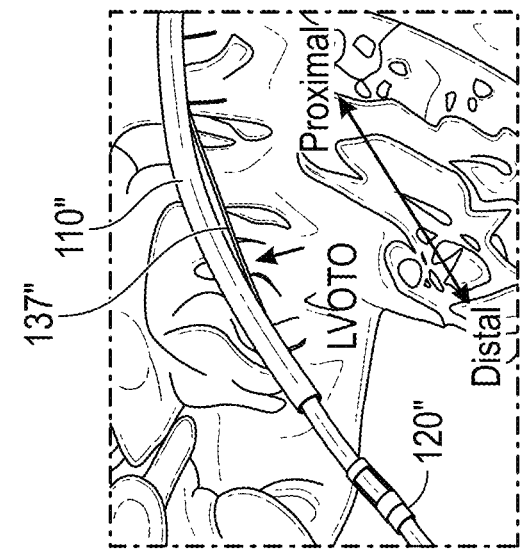
Figure 25C:
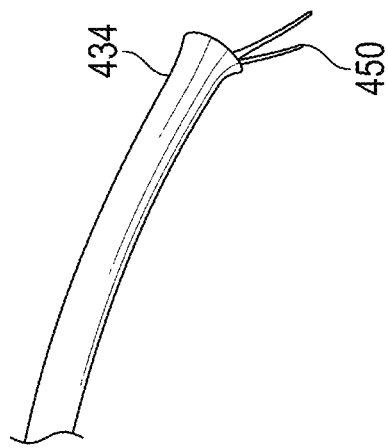
Figure 25B:
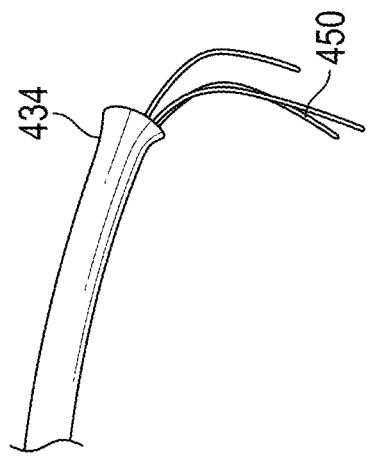
Figure 25A:
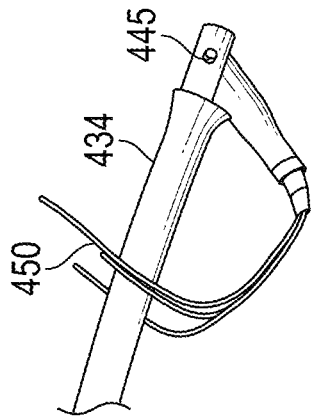

With reference to FIGS. 23A-23C, an outer catheter 110" is slidably disposed about intermediate catheter 120". An elongate cutting electrode 137" extends alongside outer catheter 110", wherein articulating, or steering the catheter 110" or applying tension to the cutting wire while the catheter 110" is bent over the tissue mass causes the electrified wire 137" to urge against the tissue. When energized, electrode 137" completes a circuit through the tissue mass in a monopolar manner, or a bipolar manner, wherein a bipolar circuit can be completed through anchor wire 127". The outer catheter 110" can be reciprocated along a proximal-distal direction over intermediate catheter 120" to complete the cutting procedure. The system 100' can then be removed by pushing catheter 180" distally over core member 140", causing the anchor wire 127" to be withdrawn into catheter 120". The system can then be removed, leaving behind the obstruction that has now been cut along its length to open the LVOT channel. While not specifically illustrated, the system components may be surrounded in a proximal location in the region of the aortic valve by an outer deflectable catheter to protect the aortic valve from electrode 137".

FIGS. 24A-25C illustrate aspects of still a further technique to treat a LVOTO in accordance with the present disclosure that includes deploying a further implementation of an anchor. As illustrated, rather than using an anchor similar to anchor 150 or 127" as set forth above, further implementations of an anchor (350, 450) are described that can be deployed out of a distal end of an innermost catheter (e.g., 130, 130') to anchor a rail (e.g., 140, 140') in place to facilitate a reciprocating cutting operation through a tissue mass (e.g., LVOTO) as discussed elsewhere herein.

FIGS. 24A-24C illustrate an anchor 350 that is pivotally coupled to a distal end of an elongate inner member 340, such as a tubular member about a pivot point 345. It is preferable that the elongate inner member 340 includes sufficient pushability to push anchor 350 distally out of a hypotube (e.g., 140' in FIG. 15), polymeric or composite tubular member, or the like. Inner member 340 can be deployed distally from a distal end 334 of a sheath or innermost catheter, for example. A tension member 344, such as a tether, can be coupled at a distal end to the anchor 350, and may be directed proximally into an exit port 342 of inner member 340 into a lumen thereof, and be externalized from a patient. FIG. 24A depicts the anchor 350 being deployed from the sheath or inner catheter, wherein a free distal, tissue piercing end of the anchor 350, which may be a flat wire or other shape, contacts the tissue along a direction indicated by the arrow. Tension is applied to the tether 344 causing it to shorten and cause anchor 350 to articulate about the pivot point 345 until the tine(s) of the anchor 350 begin to point along a proximal direction as indicated by the arrow in FIGS. 24B and 24C. In some implementations, tether 344 can include a pushable wire that can both be pulled proximally and pushed distally to help pivot the anchor about the pivot point 345 to deploy, and retrieve the anchor 350. When the anchor 350 is sufficiently proximally directed, the inner member 340 can be pulled proximally, anchoring the tine(s) of the anchor 350 into tissue, such as at the distal base of an obstruction such as a LVOTO. FIGS. 2A-25C depict an alternate version of anchor 450 that is also configured to be pulled by a proximally tensioned tether (not shown) to cause the anchor 450 to articulate about pivot 445. Tension can then be applied to the inner member of the system, pulling the tines of the anchor 450 along a proximal direction into the tissue mass.

FIGS. 26-30B illustrate aspects of a further illustrative system 500 and associated method to cut tissue in accordance with the present disclosure.

Figure 26:
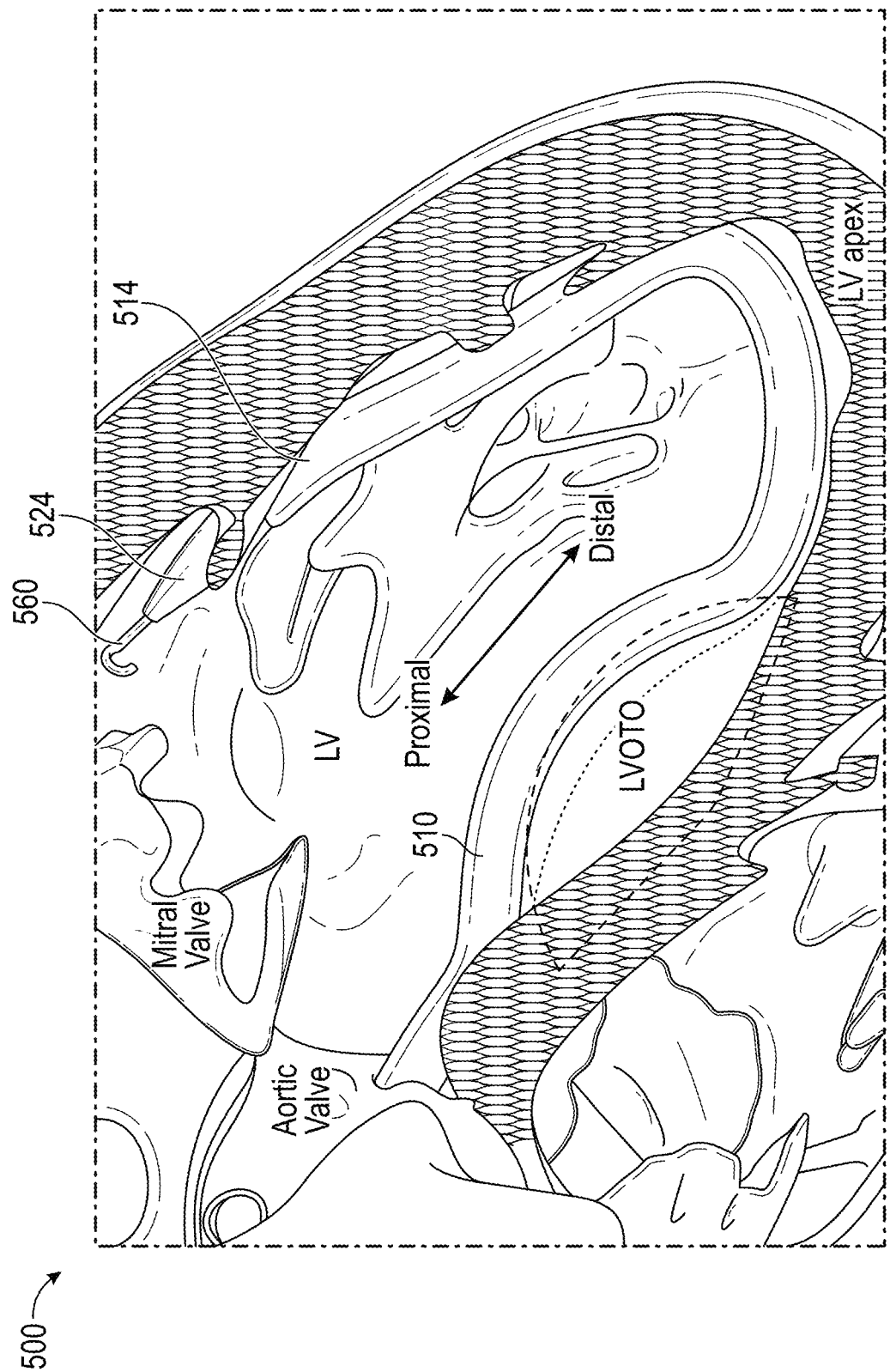
FIGS. 26-30B illustrate aspects of a further method and system to cut tissue in accordance with the present disclosure.

FIG. 26 depicts a catheter-based system encased in a sheath 500, or outer steerable catheter, that can surround the system as it is delivered to the left ventricle of a patient. The outer sheath 510 has a distal end that abuts a soft distal tip 524 of the system. The distal end of any system herein can be rounded or tapered, as desired. An inner lumen of system 500 can accommodate a guidewire 560. The guidewire 560 is first advanced to the left ventricle, and the system 500 can then be advanced over the guidewire. System 500 is sufficiently flexible to conform to the inner surface of the left ventricle as depicted in FIG. 26. The outer catheter 510 may be deflectable and/or preset with a curvature to facilitate delivery and later control of the cutting system operation, discussed in further detail below. The outer catheter 510 can be retracted proximally to a desired extent to expose a cutting wire 537, discussed in further detail below. As depicted in FIG. 26, the system 500 is situated within the left ventricle such that a primary curve is formed in the system in the apex of the left ventricle and the distal end portion of the system is situated between papillary muscles on the far wall of the ventricle. The system further conforms to and bends around an obstruction in the LVOT.

Figure 27:
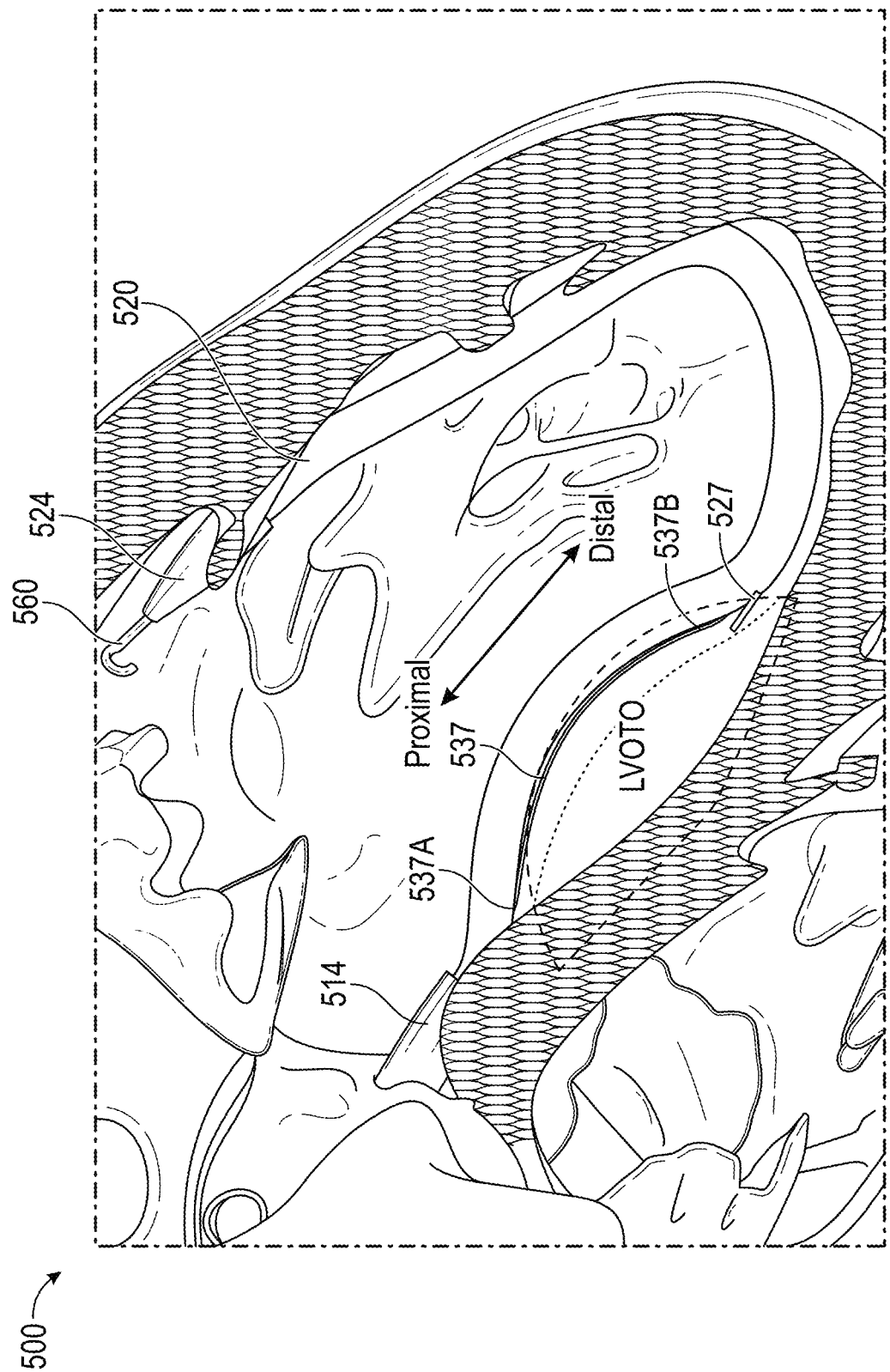

FIG. 27 depicts a further step in the procedure of using system 500 to form a cut in the LVOT. In this state, the outer sheath 510 has been retracted to the extent that the distal end 514 of the outer sheath is proximal to the tissue obstruction, but distal to the aortic valve to provide protection to the aortic valve during the cutting procedure. An inner catheter 520 is coupled to the soft distal tip 524 of the system. In addition, the inner catheter 520 defines a cutter exit port 537A and a cutter entrance port 537B that receive therethrough a reciprocating cutting element 537 therethrough. The cutting element 537 can extend distally into the body of catheter 520 through distal port 537B and be anchored at a fixed location to a rigid structure, or to an elastic structure such as a tension spring or piece of elastic. The cutting element 537 can also extend proximally into the body of catheter 520 through proximal port 537A to an actuator (not shown) that is external to the patient. When tension is applied to the cutting element 537 in a proximal direction, the cutting element is pulled proximally against the force, for example, of a tension spring (not shown) disposed within the body of the catheter 520 located distal to distal port 537B. When proximal tension is released, the cutting element 537 is pulled distally. Thus, repeated applications and removal of proximal tension to the cutting element 537 create a sawing action that cuts through the tissue either if the cutting element 537 is electrified, and/or is sharpened. Moreover, the cutting element 537 can include one or more discrete electrodes thereon that, when energized, cut through tissue as they are pulled along with the cutting element. If desired, a distal anchoring wire 527 and associated exit port 527 can be provided, wherein the anchoring wire 527 can be advanced proximally into the distal base portion of the tissue mass to help stabilize the system 500 in place. If desired, one or more radiopaque markers (not shown) can be provided at various locations on system 500, such as at the distal and 514 of the sheath, as well as at the exit port 537A, entrance port 537B, and the distal tip 524 of the system.

A variety of aspects can be used to anchor and/or stabilize system 500 in place. For example, the inner catheter 520 can be placed in the apex of the left ventricle with the distal segment against the free wall of the ventricle between the papillary muscles. This stability can be enhanced with preset curves to fit the hypertrophic cardiomyopathy (HC) or obstruction on the septum. Distal and/or proximal to the cutting target, an exit port may allow an anchoring/stabilizing element to exit the shaft, such as element 527 mentioned above. This element may include, for example, a wire that crosses the myocardium into the right ventricle, a curved element that embeds in the myocardium, or a preformed element (e.g., from a NiTi alloy) that presents as stabilizer feet. A preformed curve may be formed into body 520 in the location where it crosses over the cutting target (LVOTO) to predispose the curve to pull the distal point of the curve closer to the base of the cutting target. This can be enhanced by shortening the cutting element from the proximal handle to apply tensile force to the region of the device 520 that is distal to the entrance port 537B. The sheath 510 may be a deflectable catheter with the curve directed toward the proximal portion of the cutting target. This keeps the proximal portion of the arch close to the myocardium. The proximal sheath 510 may also help control the location of the proximal anchoring element relative to the cutting target and mechanism.

Figure 28:
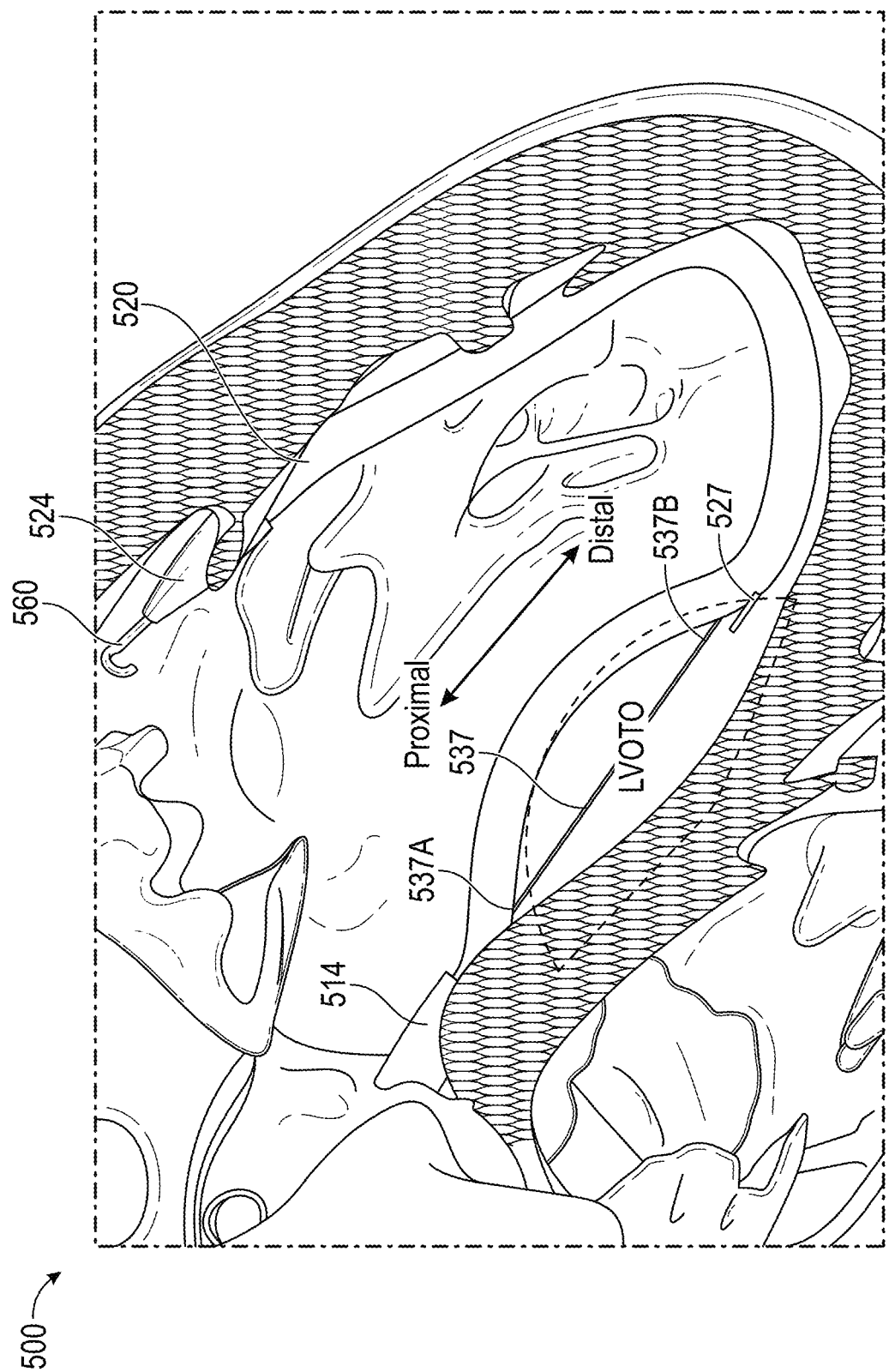

With reference to FIG. 28, the system 500 is depicted in the same side cross sectional view as FIGS. 26-27 wherein the exposed cutter 537 has penetrated tissue through various potential cutting mechanisms (e.g., reciprocating elements) that move back and forth along the tissue. A variety of reciprocating mechanisms may be used to effectuating cutting with cutting element 537. For example, as mentioned above, distally located spring disposed, for example, in body 520 may be used to return the cutting element distally after the cutter is pulled proximally. Alternatively, both ends of the cutting element 537 may be connected to a proximal tension element, wherein the cutting element or tether attached thereto reverses direction about a transition point, such as the distal entrance port 537B or a rounded boss located inside inner catheter 520 located distally to the distal entrance port 537B. Thus, both ends of the tension element coupled to the cutter 537 can be externalized and each end can be pulled alternately to effect reciprocating cutting motion. In another implementation, a proximal end of the cutter 537 can be connected to a tube or rod (not shown) located within inner catheter 520 located proximally with respect to exit port 537A that advances and retracts through inner catheter 520 the distal end of the cutter 537 is connected to a spring or other elastic element disposed within the inner catheter 520. Cutting element 537 in the region where cutting is performed may include a smooth radiopaque wire or tether, a textured radiopaque wire or tether, a diamond coated wire, a radiofrequency ("RF") wire or electrode operating in RF or microwave regimes, a length of razor wire, a cutting blade coupled to a reciprocating tether, an ultrasonic transducer or element coupled to an ultrasonic transducer, and the like.

Figure 29:
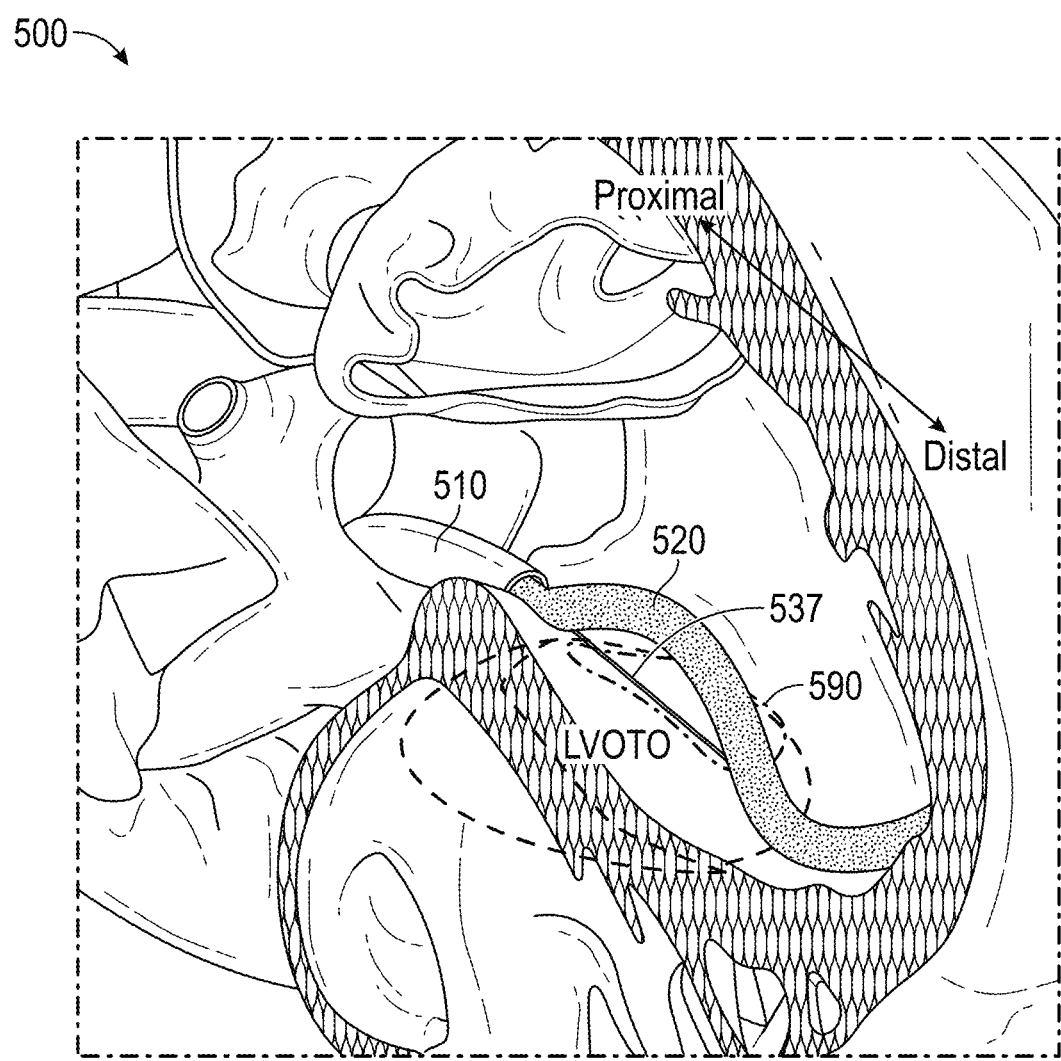

FIG. 29 depicts an isometric view of the implementations presented in FIGS. 26-28. As depicted, once cutting is complete, the tissue of the LVOTO is splayed open as defined by the perimeter 590 illustrated in FIG. 29. This splaying open of the tissue enlarges the cross-sectional area of the LVOT, thereby reducing the risks associated with implanting an artificial valve, as mentioned above. The system 500 can then be removed, for example, by advancing the sheath 510 distally over inner catheter 520 and cutter 537 to protect surrounding tissue from the cutter 537 during withdrawal. The system 500 can then be withdrawn with the guidewire 560.

Figure 30A:
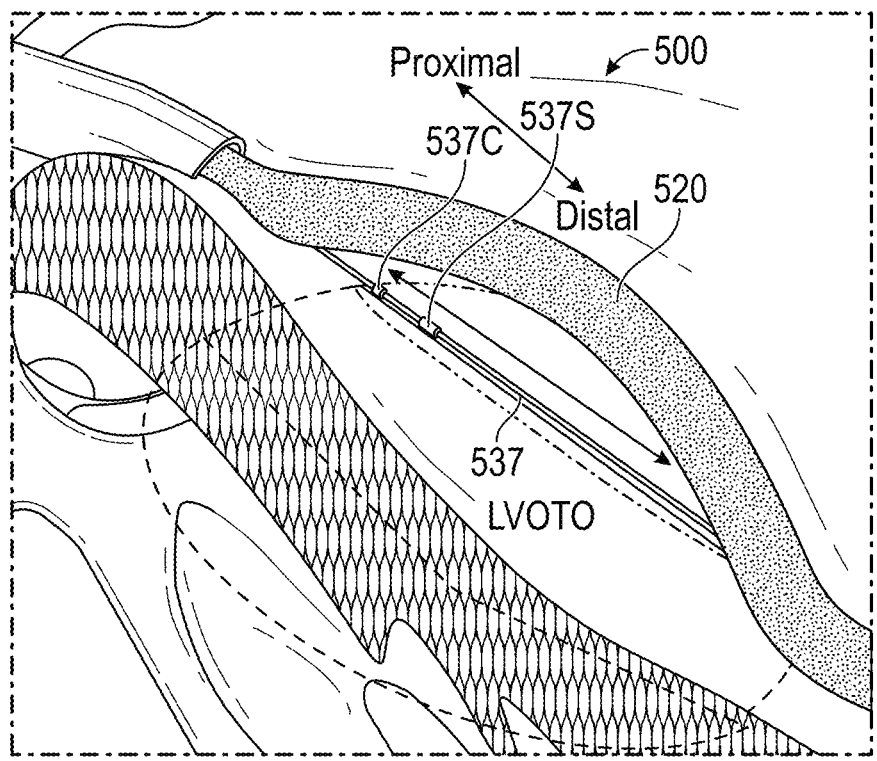
Figure 30B:
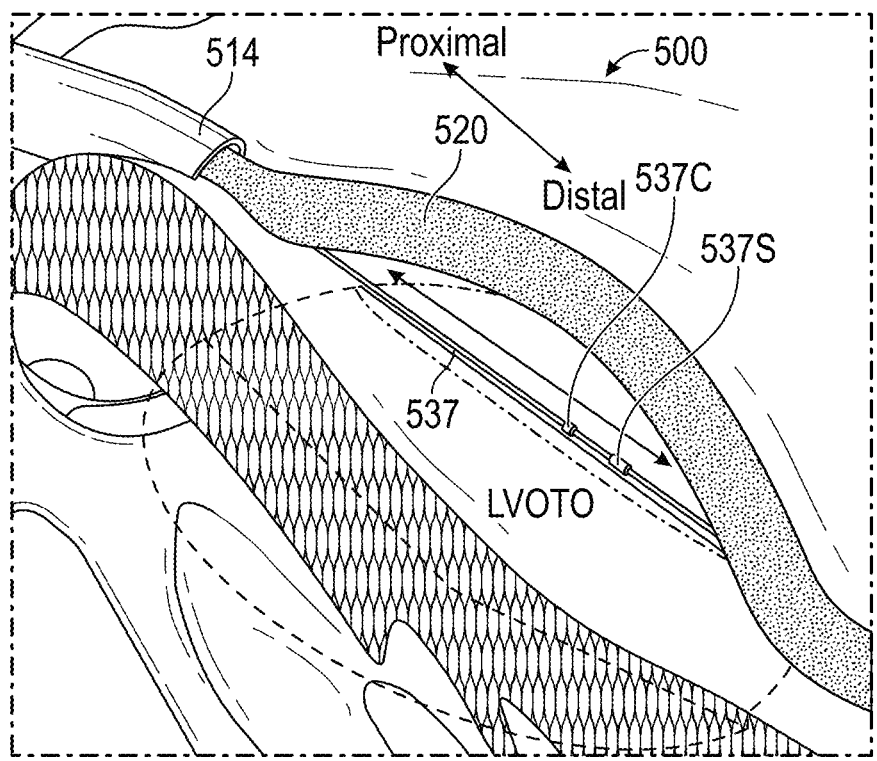

FIGS. 30A-30B depict a variation of system 500 wherein the reciprocating cutter 537 includes a first electrode 537C disposed thereon for RF cutting, and a second electrode 537S mounted thereon for EDEN (Electrocardiogramadial Depth Navigation) sensing. EDEN sensing is based on detection of an EKG signal to detect tissue depth. Each electrode 537C, 537S is electrically coupled to a conductor that may pass inside of cutter 537 and extend proximally through system 500 and out of the patient. As the cutting is being performed by electrode 537C, electrode 537S picks up EKG signals that can be used to help estimate the current depth of the cut into the myocardial tissue.

FIGS. 31-40 depict further implementations of a catheter system in accordance with the present disclosure, or aspects thereof, having a different actuator assembly than the system of FIG. 5. For purposes of reference, the proximal and distal directions of the assembly are indicated in various figures.

Figure 31:
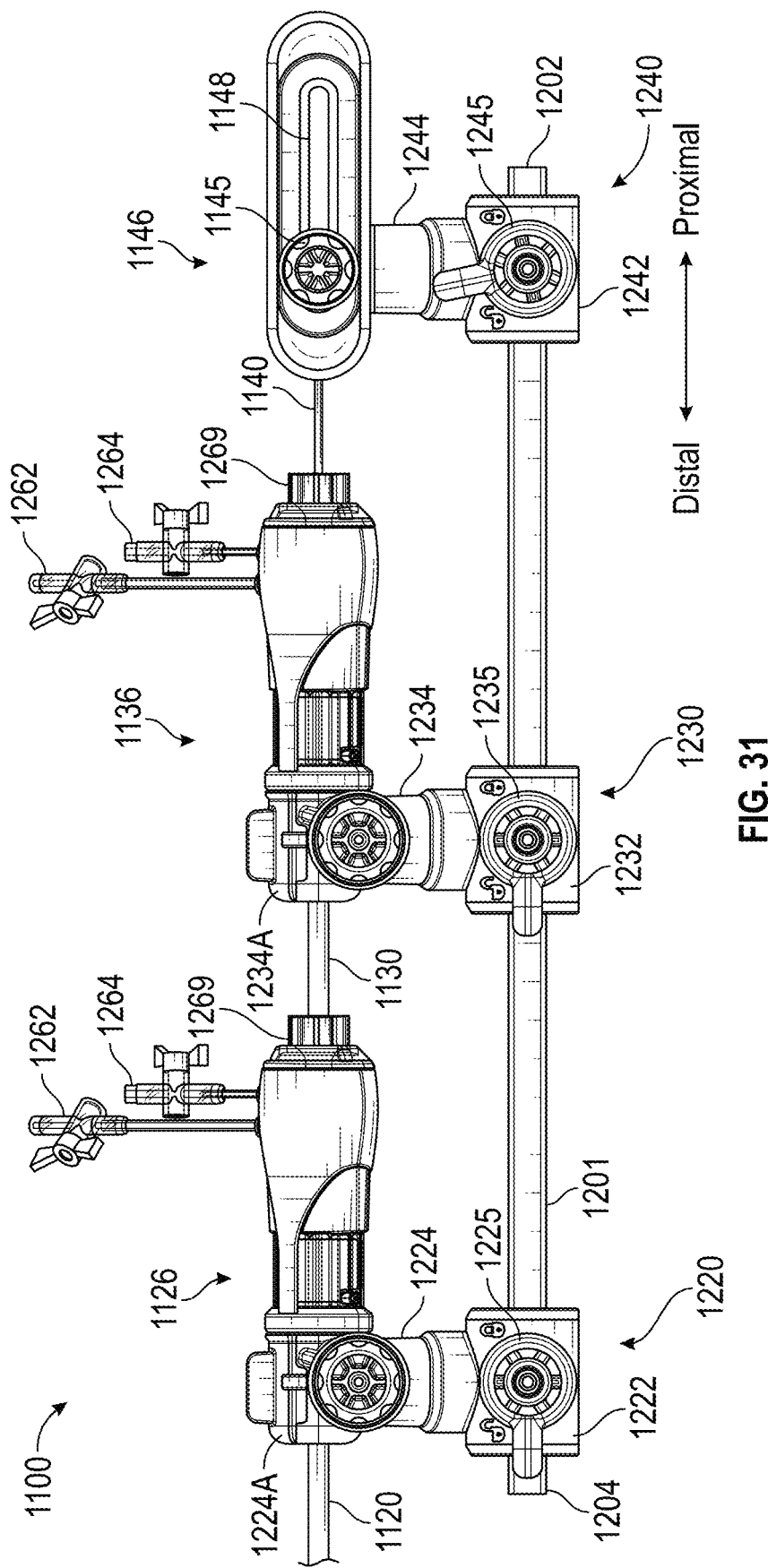
FIG. 31 is a side plan view of a further implementation of an actuator assembly for a catheter system in accordance with the present disclosure.

FIG. 31 is a side view of a catheter-based system 1100 to perform a percutaneous procedure to cut tissue in accordance with the present disclosure. While the system 1100 can utilize a reciprocating cutter as described elsewhere herein, the system 1100 can be configured with different end effectors to perform different procedures, and can be provided with any desired number of overlapping catheters. For example, while the illustrated implementation 1100 includes a pair of concentric catheters 1120, 1130 surrounding a central tether 1140, a third, fourth and/or fifth concentric catheter can be added surrounding catheter 1120. By way of further example, the central tether 1140 may be omitted in the assembly and the system can be used as a two-catheter system. Alternatively, a smaller catheter, such as a microcatheter can be inserted inside the lumen of catheter 1130, and a further actuator similar to or the same as actuators 1126, 1136 can be used proximally of catheter 1130 and inside of catheter 1130.

As indicated above, system 1100 includes two concentrically disposed deflectable catheters including a radially outermost catheter 1120, within which a second deflectable intermediate catheter 1130 is slidably received. A tether 1140 in the form of a flexible suture, a wire with column strength and pushability, or a pushable tubular member, or other instrumentality, such as a guidewire, a snare or the like is slidably received within catheter 1130. Each deflectable catheter 1120, 1130 can include one or more steering wires (FIG. 34, 1121) to which tension can be applied to selectively cause the distal end of each respective catheter 1120, 1130 to bend in a preferential direction. References to steerability or deflectability of catheters herein can encompass active steering, such as with a tension wire, or steering using flexible or deflectable catheters of lower relative durometer. The distal region of one or more catheters may be configured to bend in a preferential direction. Rotating each respective catheter 1120, 1130 about their central axis will cause the bent distal end of each respective catheter to point in any desired direction inside the patient. The catheter 1120, 1130 can then be advanced distally into a desired anatomical structure.

As depicted in FIG. 31, each 1120, 1130 is comprised of a tubular body having a proximal end coupled to an actuator 1126, 1136 and a free distal end (not shown) in a manner that is similar to, or the same as, catheters 120, 130. Each catheter 1120, 1130 can be moved axially and rotationally with respect to the other components of system 1100. Each catheter 1120, 1130 is held in relative position by a respective carriage 1220, 1230 that is slidably received on a rail 1201 of a stand 1200 (see FIGS. 37, 38). Tether 1140 is likewise coupled to a tensionable anchor 1146 that is in turn operably coupled to a carriage 1240. Each carriage 1220, 1230, 1240 can be axially translated between the proximal end 1202 and the distal end 1204 of the rail 1201. In the illustrated implementation, one or more of the carriages 1220, 1230, 1240 can be locked in place with respect to the rail 1201 by engaging a rail lock by rotating a lock handle 1225, 1235, 1245. For example, the lock handle 1225, 1235, 1245 can actuate a clamping mechanism to clamp the actuator 1126 in place with respect to rail 1201, for example, by advancing a threaded fastener against the rail 1201, or by tighten a clamp that surrounds the rail 1201, or by rotationally advancing a cammed fastener against the rail 1201, among other options.

Figure 32:
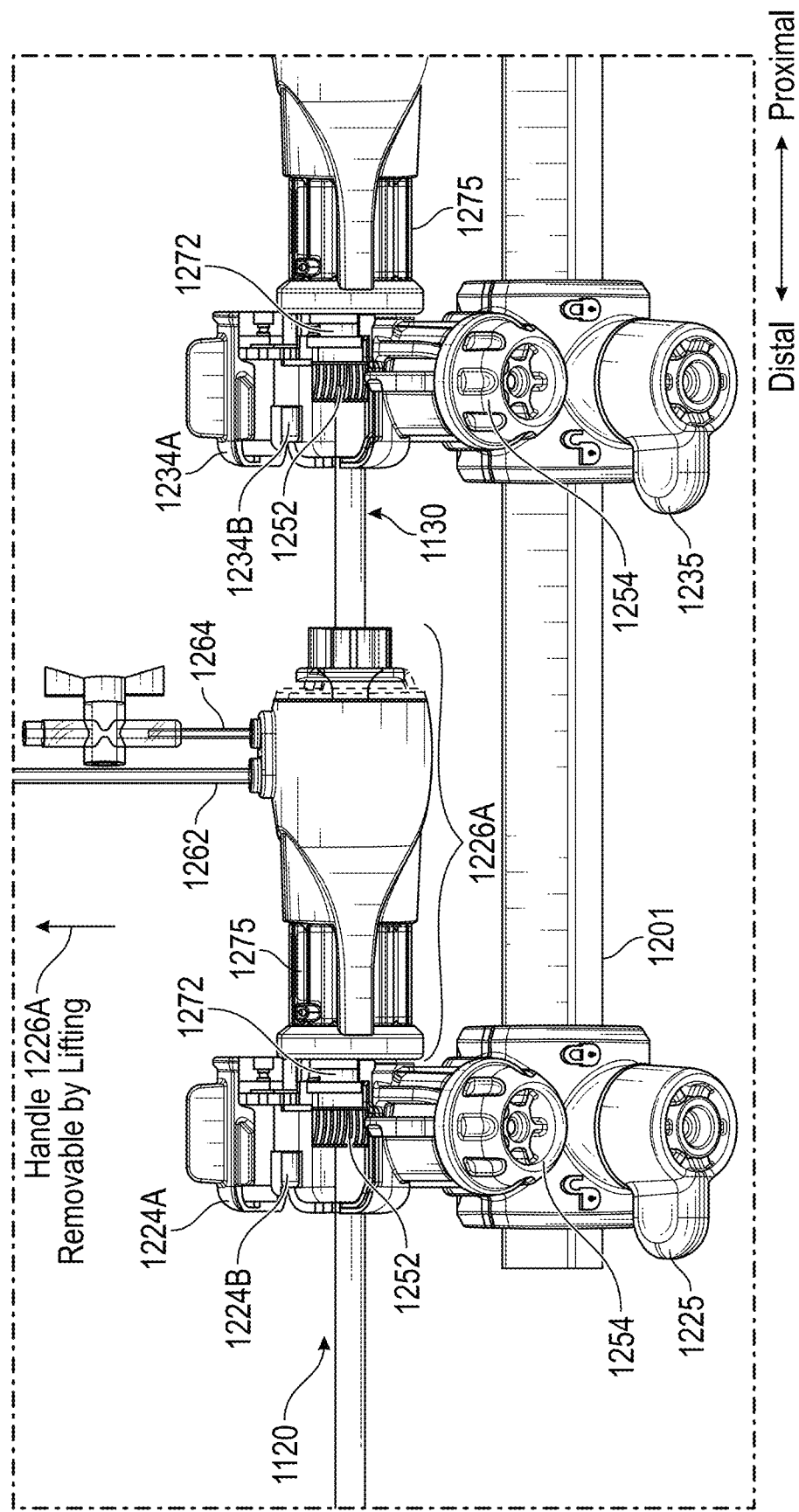
FIG. 32 is an enlarged upper isometric view of a portion of the actuator assembly of FIG. 31.

With continuing reference to FIGS. 31-32, actuator 1126 is formed from a first component including a main body portion 1222 that can partially or fully surround rail 1201 and slide proximally and distally over rail 1201 when the lock handle 1225 is disengaged. The actuator 1126 extends upwardly from the base portion 1222 into an upwardly extending portion or mount 1224, illustrated in FIG. 31 as a hollow outer housing portion that extends upwardly into an upward housing portion that defines a cradle to receive the proximal end of catheter 1120 therein. A clamp or door 1224A closes over the catheter, holding it in place, for example, by way of an interference fit or other suitable disengageable connection.

With reference to FIG. 32, as with the implementation of FIG. 5, each catheter 1120, 1130 is received along a vertical direction into an upwardly extending mount 1224, 1234' of a respective carriage 1220, 1230. More specifically, a handle portion 1226A, 1236A of each actuator 1126, 1136 can be lifted out of each mount 1224, 1234 when a removable cover 1224A, 1234A is removed, permitting the respective catheter and handle to be lifted out of the mount. In the implementation of FIG. 5, the catheter is received in a fork shaped coupling. In the implementation of FIG. 32, the proximal end of each catheter 1120, 1130 is surrounded by a hub 1272 that is comprised of a gear 1252 and a flange 1272A-1272E that defines a circumferential channel 1272E about at least a portion of its periphery that straddles a ridge or boss 1229 (FIG. 33) in the mount 1224, and is rotatably received with respect to the ridge or boss 1229 so that the handle 1126A may be rotated within mount 1224 when the knob 1254 and worm gear are 1256 is rotated, causing gear 1252 to rotate. When installed about ridge 1229, the catheter including handle portion 1226A is held in place longitudinally in mount 1224 when door 1224 A is closed, but the handle and hub 1272 can rotate in place in the mount 1224 when knob 1254 is rotated. Placement in mount 1224 prevents axial movement of catheters 1120, 1130 with respect to carriage 1220, 1230. Each carriage (e.g., 1240) is defined by a main body portion (e.g., 1242) that defines a channel (e.g., 1248) therethrough to at least partially surround rail 2201 of stand 2200.

Figure 33:
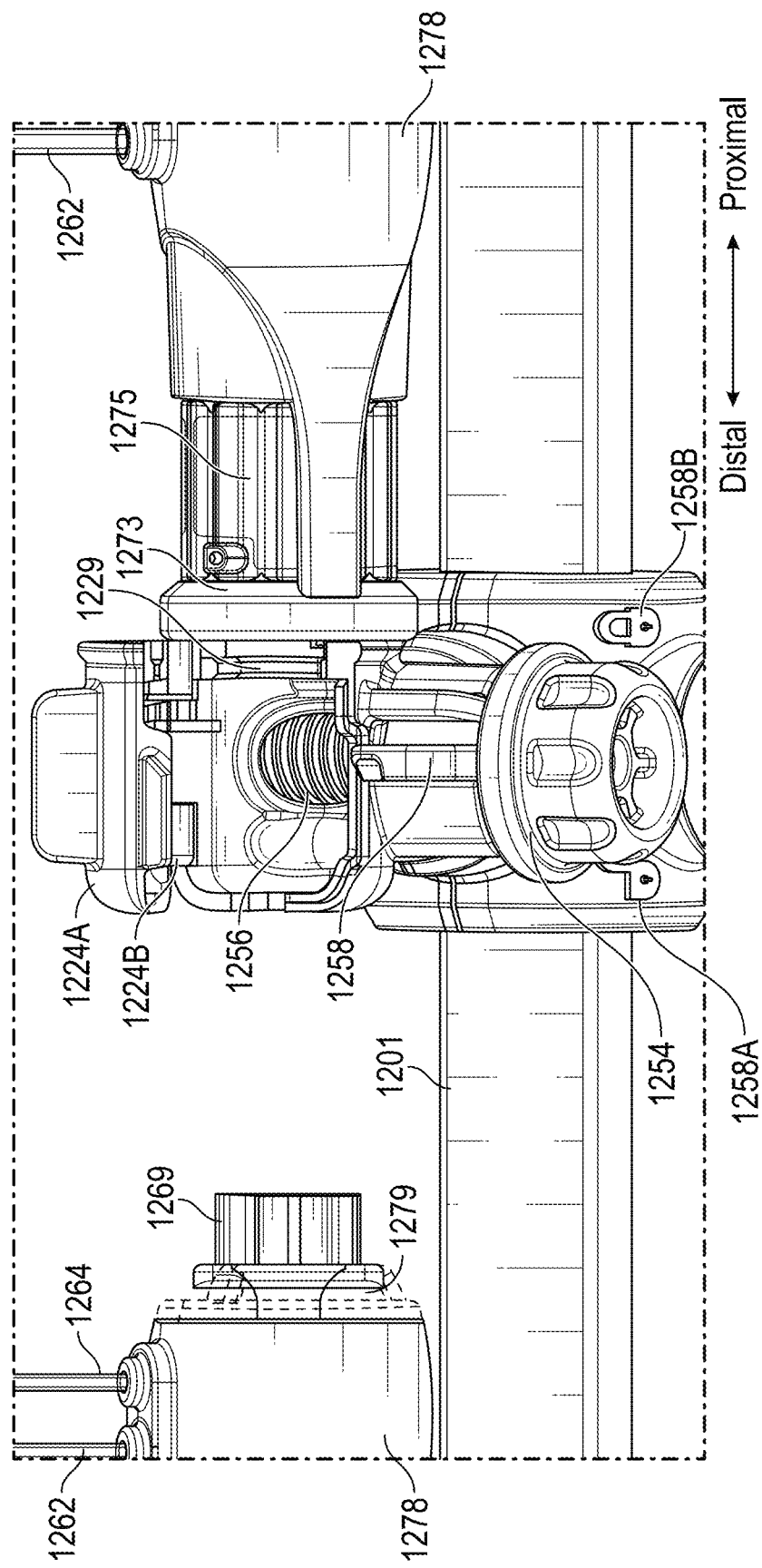
FIG. 33 is a further enlarged upper isometric view of a portion of the actuator assembly of FIG. 31.

With reference to FIGS. 32-33, when installed in mount 1224, 1234, each catheter the proximal gear 1252 that is operably coupled to each catheter meshes with a respective worm gear 1256 that is rotatably situated within each mount and operably coupled to a respective handle 1254. In this manner, rotation of the handle 1254 causes the worm gear 1256 to rotate about a central axis of rotation. The intermeshing of the winding of the worm gear with the teeth of the gear 1252 causes gear 1252 to rotate about a central axis of catheters 1120, 1130. Since gear 1252 is directly or indirectly coupled to the proximal end of each catheter 1120, 1130, the catheter 1120, 1130 also rotates when its respective handle or knob 1254 is rotated. This provides a fine adjustment to help steer each catheter through tortuous anatomy.

As such, each of catheters 1120, 1130 can be displaced rotationally about a central axis of the system (e.g., about tether 1140), and with respect to each other. It will be appreciated that any of catheters 1120, 1130 (or additional catheters combined with catheters 1120, 1130) can be utilized with stand 1200 alone, or in combination with other system components. Thus, a double catheter assembly may be used as depicted in FIG. 31, or a single or double catheter assembly may be used if all three catheters are not required.

Catheters 1120, 1130 can be of any desired length. In accordance with some implementations, catheter 1120 can be between about 90 cm and about 140 cm in length, or any increment therebetween of about one centimeter. In accordance with still further aspects, catheter 1130 can be between about 100 cm and about 160 cm in length, or any increment therebetween of about one centimeter. Tether 1140 can be any desired length, such as between about 120 and 300 cm in length, or any increment therebetween of about one centimeter. Other than the actuator portion(s) catheters 1120, 1130 can be the same or substantially the same as catheters 120, 130, for example.

As further depicted in FIGS. 31-32, the actuators 1126, 1136 can be selectively translated proximally or distally with respect to rail 1201 by unclamping the lock that holds each actuator in place by rotating lock handle 1225. When a respective lock handle 1225 is loosened, each actuator 1136, 1136 can be slid along the rail 1201. When a desired location within a patient's vasculature is reached, the actuator 1126, 1136 can then be locked in place by tightening its respective lock handle 1225. This provides for a "coarse" adjustment of the position of each catheter 1120, 1130. If desired, a finer adjustment can be provided between the carriage 1220, 1230, 1240 and the rail, for example, by forming a gear rack into or on top of rail 1201 that engages a rotational actuator of each carriage (not shown) with gear teeth that engage the rack to permit the position of the carriage 1220, 1230, 1240 to be adjusted by rotating a knob of the rotational actuator. The illustrated carriages are depicted with only having the aforementioned coarse adjustment.

Figure 34:
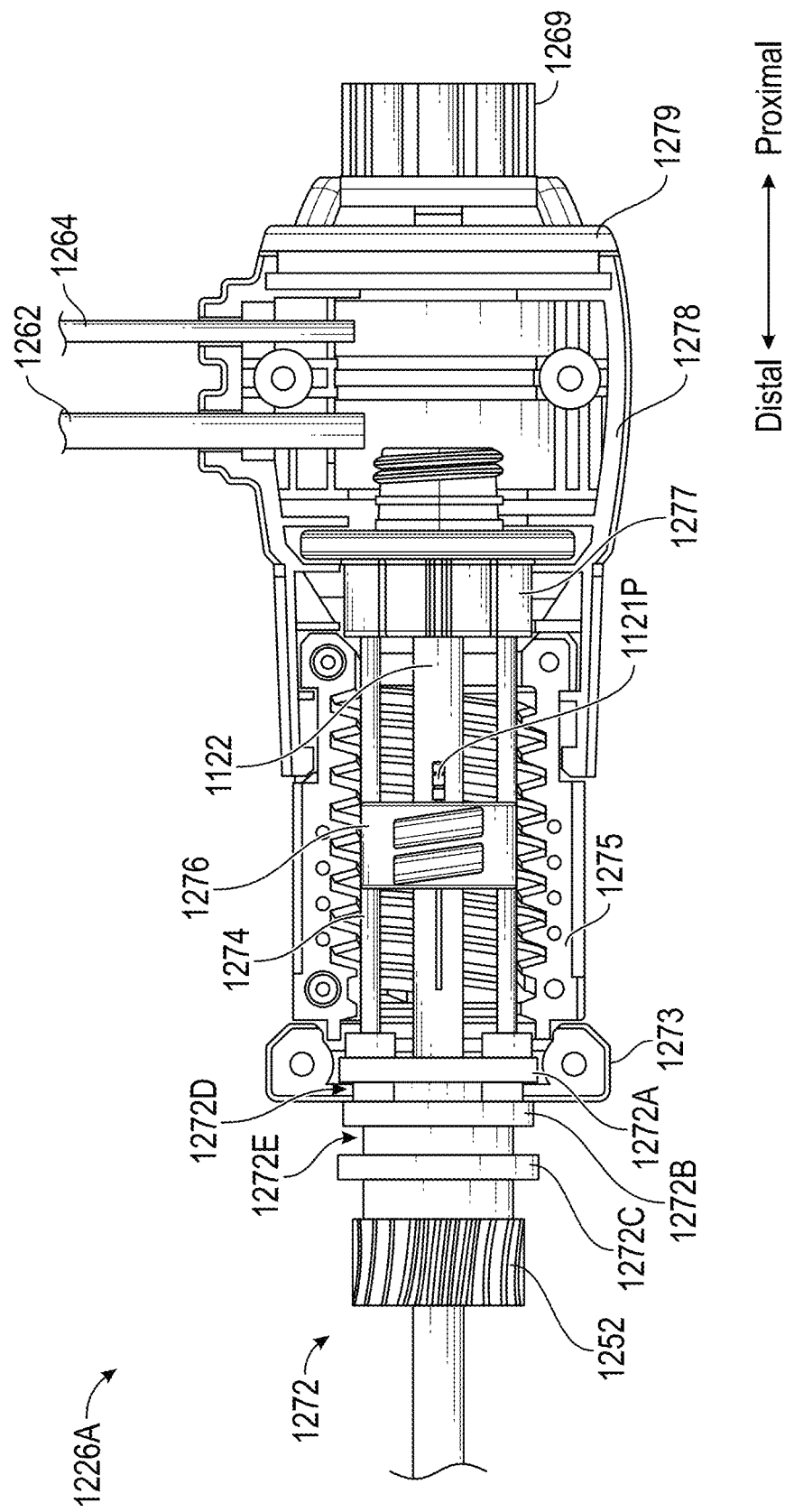
FIG. 34 is a side view of a handle portion of an actuator assembly of FIG. 31 with a lateral half of the outer housing removed.

With reference to FIGS. 33-34, each actuator 1126, 1136 can include a steering mechanism that utilizes one or more tensioned pull wires that are actuated from within the handle (e.g., 1226A) of the actuator 1126. FIG. 34 depicts the catheter 1120 and handle 1226A after it has been lifted out of mount 1224, and after removal of one half of the outer housing to view interior components. The handle 1226A is constructed from an outer housing that includes a distal housing section 1273 coupled to a proximal housing section 1278 by one or more longitudinal bridges that pass radially outwardly past a rotatable pull wire actuator handle 1275 defining threads along its interior surface. The hub 1272 including gear 1252 and flange 1272A-1272E can be formed from a single molding that is received in the distal housing component 1273. As illustrated, the flange portion of the hub 1272 includes two distally located disc shaped portions 1272B, 1272C separated by a channel 1272 defined by an outwardly facing annular surface that contacts ridge or flange 1229 of actuator 1126. The hub 1272 further includes a proximal enlarged portion 1272A having a shape that is slidably received within a channel defined in each half of the housing of handle 1226A to prevent relative rotation of hub 1272 with respect to the housing 1273, 1278 of the handle 1226A. On its proximal face, hub 1272 defines a pair of sockets to slidably receive a distal end of one or more rails 1274. The proximal end of the one or more rails 1274 are received by a proximal collar 1277. The proximal collar 1277 is fixedly coupled to the proximal end 1122 of the tubular portion of the catheter 1120. A carriage 1276 defining a plurality of threads thereon is threadably received by the interior threaded surface of handle 1275 and is slidably received over the rails 1274. Carriage 1276 is attached to a proximal end 1121P of a pull wire 1121 that is operably coupled to a distal end of catheter 1120. Movement of the carriage proximally or distally over rails 1274 is effectuated by rotating handle 1275 with respect to the housing of handle 1226A. The interior threaded surface of handle 1275 pushes the carriage 1276 along the rails. Movement of the carriage 1276 proximally applies tension to the pull wire 1121, causing the distal tip of the catheter 1120 to deflect off of the catheter's longitudinal axis. Rotation of the handle 1226A with respect to and within the carrier 1220 permits rotation of the deflected end of the catheter, permitting the distal end of the catheter to be advanced through tortuous anatomy.

FIG. 34 further illustrates that the proximal collar 1277 is held in a fixed rotational and axial position within the housing of the handle 1226A such that the proximal end 1122 of catheter is also held axially and rotationally in place with respect to the housing of the handle 1226A. A proximal portion of the handle 1226A is defined and surrounded by proximal housing portion 1278, which receives flush line 1262 and inflation line 1264, discussed below; as well as a proximal cap 1279 and a further lock collar 1269 containing a further circumferential fluid seal to prevent liquids accumulating within handle 1226A from leaking out.

Figure 35:
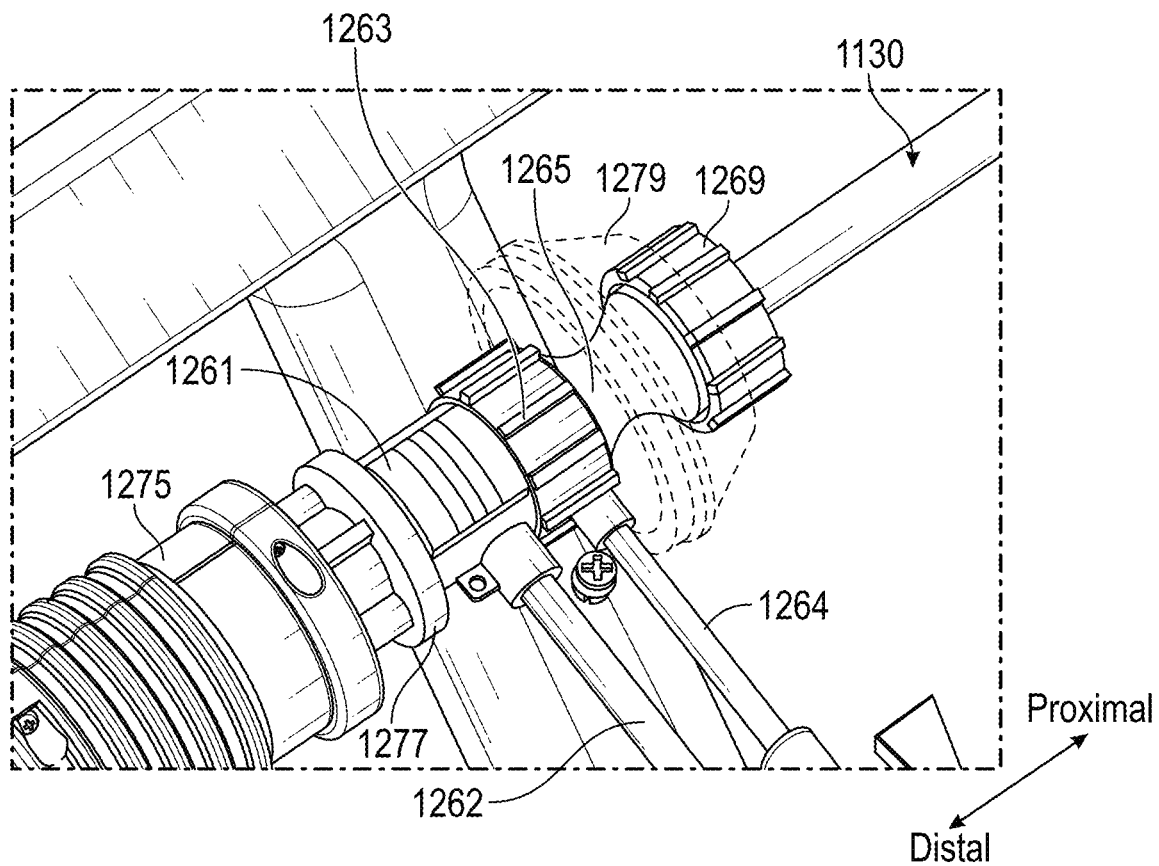
FIG. 35 is a view of internal components of an illustrative handle assembly in accordance with the present disclosure.

As further illustrated in FIGS. 31, 34, and 35 actuator 1126 includes a valved flush line 1262 in fluid communication with an interior lumen of catheter 1120 and a second lumen 1264 to receive a pressurized fluid to inflate a toroidally shaped inflatable member, or balloon 1265 (FIG. 35) that seals against the outer surface of catheter 1130, to prevent leakage of fluids from a patient past the proximal end of catheter 1120. FIG. 35 depicts a slight variation 1226A of handle 1226A (also illustrated in FIGS. 36 and FIGS. 38-40) showing interior components of the handle 1226. Although not visible in FIG. 34, FIG. 35 illustrates additional internal components to which the flush line 1262 and inflation line 1264 attach. Specifically, an interior fluid manifold is depicted that includes a flush housing 1261, an inflation housing 1263, an inflatable member 1265 and a proximal lock collar 1269. The fluid manifold can be formed from components that are integral or separate. Flush line 1262 is in fluid communication with an interior volume (not shown) within flush housing 1261 that in turn is in fluid communication with the interior lumen of catheter 1120. In this manner, a flushing fluid, or other beneficial agent, can be introduced to a tissue region being treated by directing the fluid through line 1262, into the chamber within flush housing 1261, and down the lumen of catheter 1120 to the distal end of catheter 1120 where the fluid is ejected at the location proximate tissue being cut during an electrosurgical process, for example. The beneficial agent or flush can include a dextrose flush, for example, to the area being treated.

With continuing reference to FIG. 35, adjacent to and proximal to the flush housing 1261 is an inflation housing 1263 having an interior cavity (not shown) that is in fluid communication with inflation line 1264. The chamber within inflation housing 1263 is in turn in fluid communication with annularly or toroidally shaped inflatable member 1265, which is defined by inner and outer flexible surfaces that deflect when the inflatable member 1265 is inflated by directing pressurized fluid through inflation line 1264. The annular inflatable member inflates radially inwardly to seal around the outer surface of catheter 1130, and radially outwardly to occupy volume within the housing of the handle 1226A to prevent leakage of flushing fluid, for example, out of handle 1226A, or bodily fluids from a patient. The fluid manifold terminates at a proximal end with lock collar 1269, which can comprise an internally threaded outer member that can rotate with respect to an externally threaded inner member and a compressible seal between the two components to cause the compressible seal to be urged against the outer surface of catheter 1130 when the lock collar 1269 is tightened.

Figure 36:
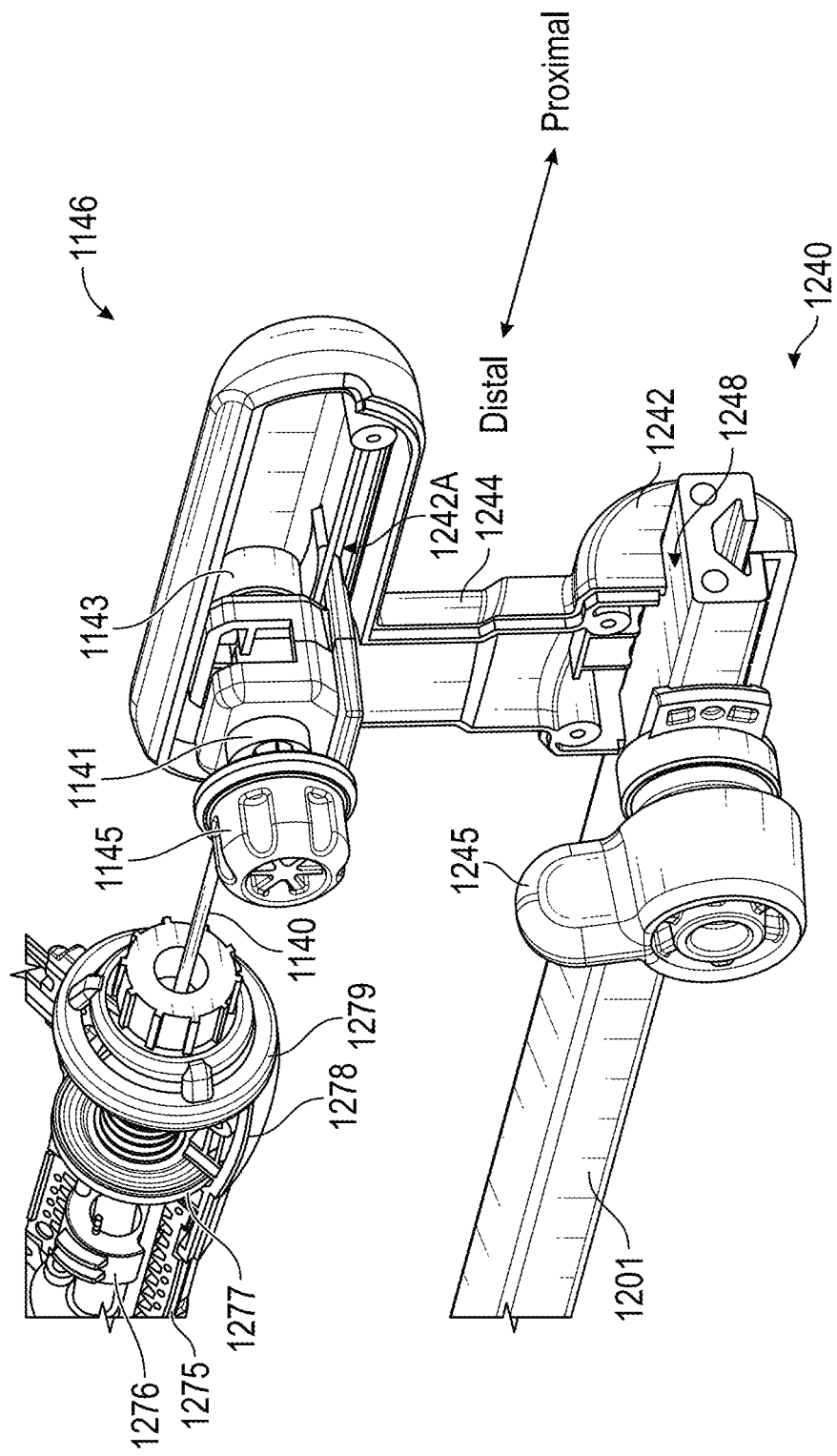
FIG. 36 is an isometric view of a linear tensioner in accordance with the present disclosure depicting half of the housing portion removed.
Figure 37:
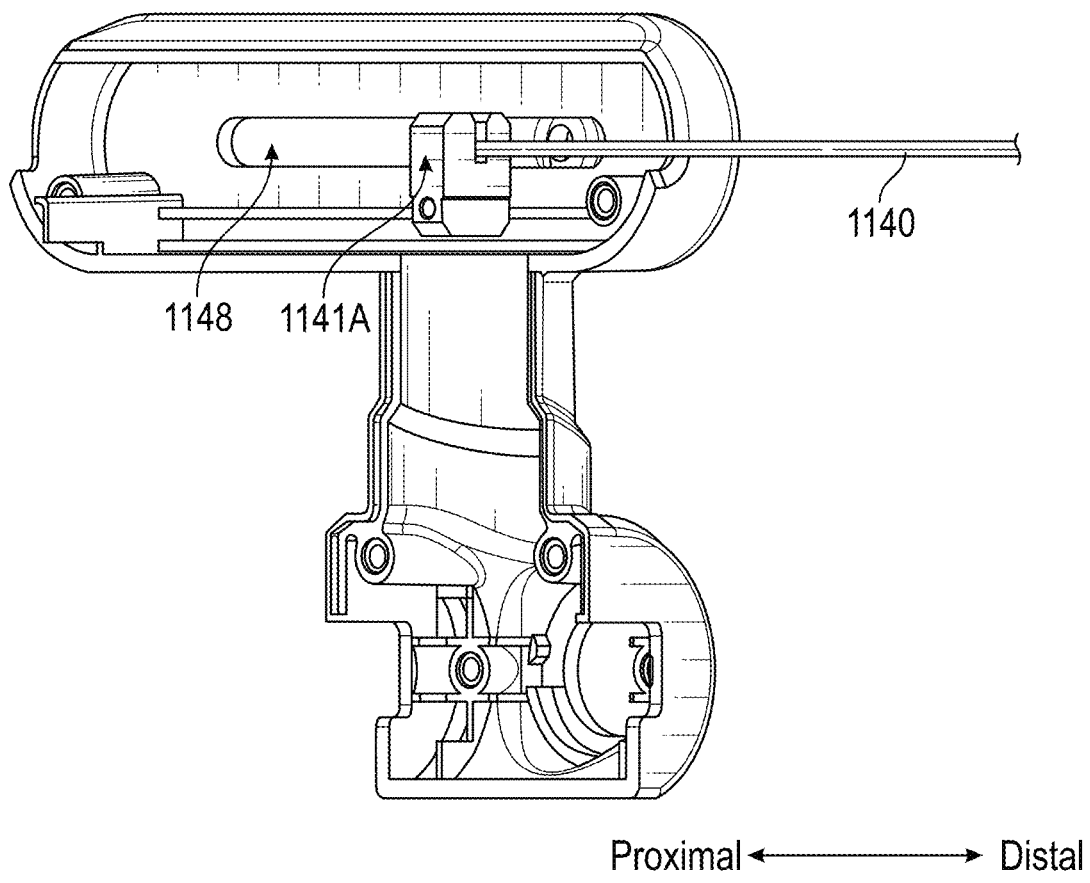
FIG. 37 is an isometric view of the housing component omitted from FIG. 36.
Figure 38:
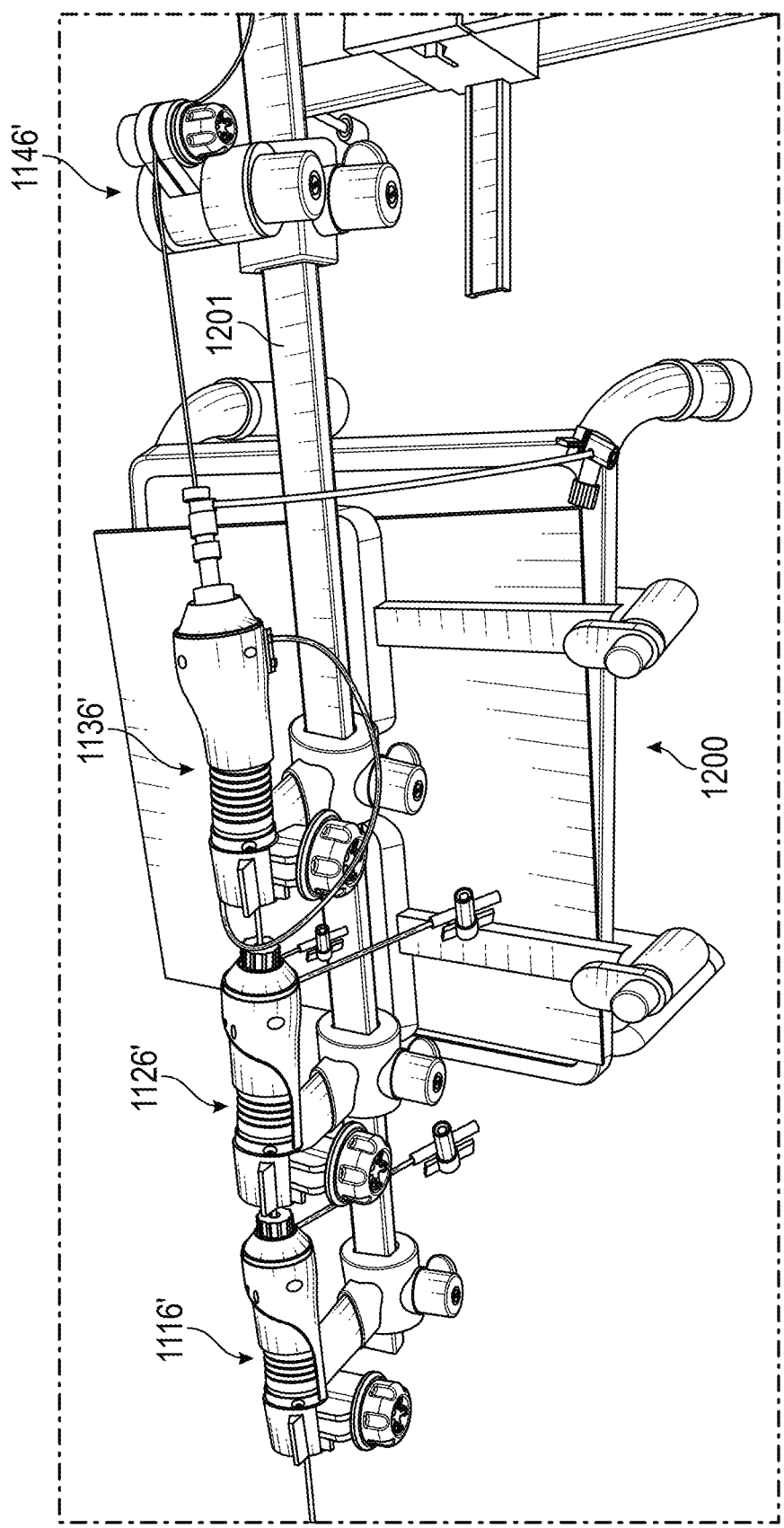
FIG. 38 is an isometric view of a variation of an actuator assembly in accordance with the present disclosure.

A detailed illustration of tensionable anchor 1146 is depicted in FIG. 36. Anchor 1146 includes a housing having a slidable handle 1145 that slides along a slot 1148 (FIG. 31, FIG. 37) in the outer surface of the housing of the anchor 1146. Handle 1145 is operably coupled to a proximal region, or a proximal end, of tether 1140 in any of a variety of manners. In the illustrated implementation, the handle 1145 can be coupled to a shaft (not shown) that passes through a shuttle 1141 that in turn is connected to a coil spring 1143, wherein the coil spring 1143 is coupled to an interior portion of the housing of anchor 1146. The tension on the coil spring 1143 can be adjusted by rotating handle 1145, which then applies a proximally directed force on a proximal end or end region of the tether 1140 to apply tension to the tether 1140 when the distal anchor coupled to the tether is anchored in tissue. FIG. 36 depicts a half of the housing of anchor 1146 as being removed, and presented in FIG. 37. The shuttle 1141 includes one or more bosses that ride in a channel 1242A formed into the housing of the anchor 1146. An anchor block 1141A (FIG. 37) is operably coupled to the proximal end of the tether 1140. Anchor block 1141 can be slidably received (e.g., along a vertical direction) in shuttle 1141.

Figure 39B:
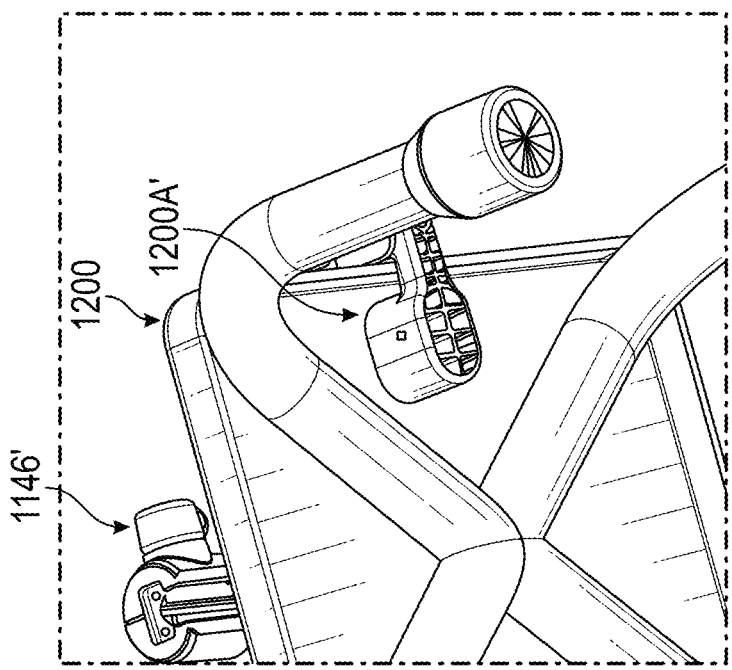
FIGS. 39A-39B are different isometric views of the actuator assembly of FIG. 38 mounted to a stool.
Figure 39A:
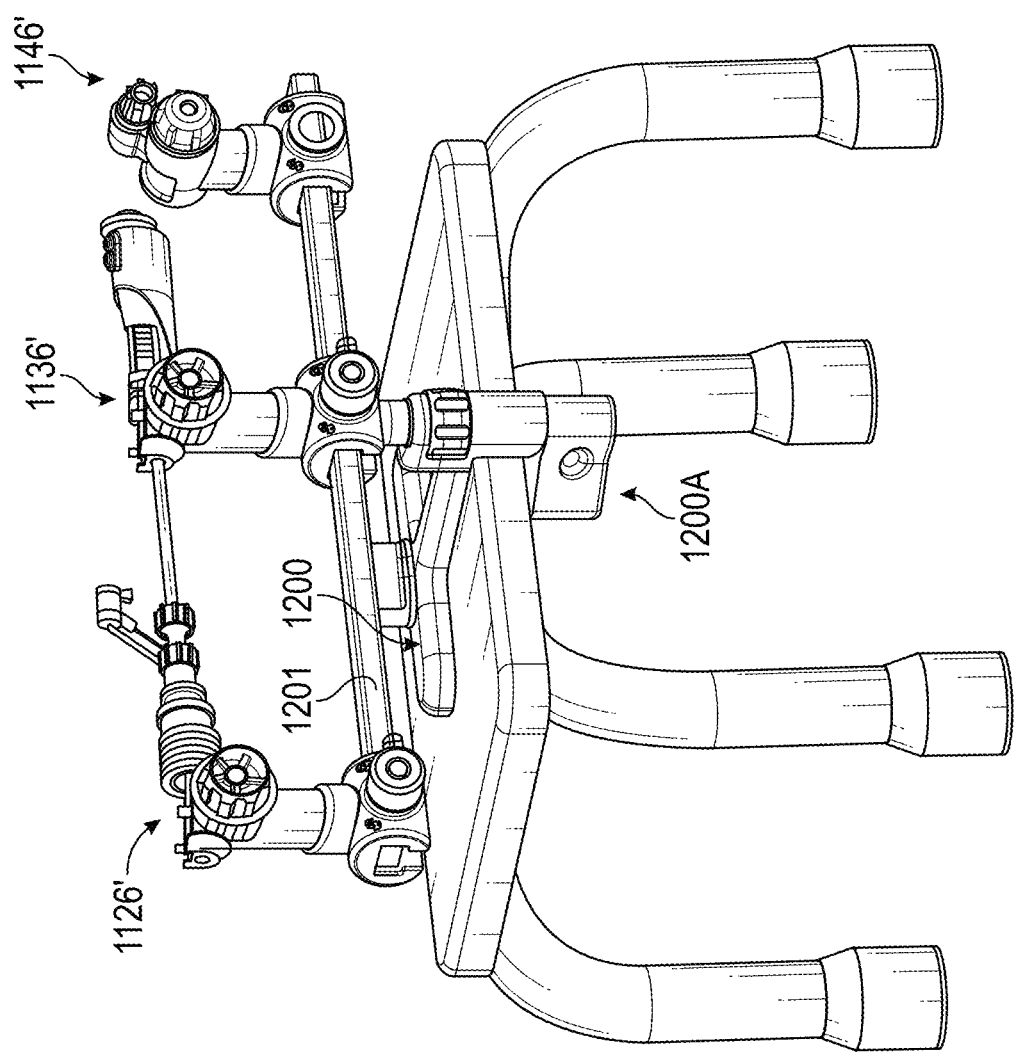

FIG. 35 depicts a slight variation of the actuator assembly 1100 showing three actuators 1116', 1126', 1136' having components and functionality similar to actuator 1126, 1136 that are configured to be coupled to three concentric catheters, such as catheters 110, 120, 130. A further anchor 1146' is depicted that applies tension to a central tether, wherein the anchor includes an arm that is attached to the tether, wherein the arm pivots about a pivot point, and is spring loaded to apply tension to the tether. The actuators are slidably mounted to a rail 1201 that in turn is coupled to a base frame 1200 that is clamped to a stool or other object by a clamp 1200A. FIGS. 39A and 39B illustrate vies of the manner in which the actuator assembly can be coupled to a stool or other object. Specifically, the rail 1201 is coupled to a base portion 1200 that rests on a surface, such as a table or stool, that can be clamped in place using a clamp 1200A that wraps around an edge of the surface on which the base portion is sitting. In the illustrated implementation, the clamp is actuated by up and down movement. If desired, the rail 1201 may include measurement indicia along its surface and if desired may be provided with additional stoppers (not shown) that can be received over the rail 1201, slid to a desired position, and tightened in place against the rail 1201. The stoppers can be placed in locations on either side of one or more of the actuators to limit the degree of travel of the respective actuator along the rail 1201.

In further accordance with the disclosure, a variety of methods are provided of performing a medical procedure using the actuator assembly and catheter arrangements described herein. For example, a system of nested catheters (e.g., 110, 120, 130) can be directed or advanced to a target location inside a patient. A distal end of an outermost tubular catheter (e.g., 110) can be placed in a first location. A distal end of a further tubular catheter (e.g., 120) can be placed in a second location located distally with respect to the first location. A distal end of an inner tubular catheter (e.g., 130) can be placed in a third location located distally with respect to the second location. The method can then include performing any one or more of a variety of a therapeutic or diagnostic procedures using at least one of the catheters (e.g., 110, 120, 130).

In some implementations, a distal region of the outermost catheter (e.g., 110) can be disposed in an aortic arch of a patient, a distal region of the further tubular catheter (e.g., 120) can be disposed through a cardiac valve of a patient, and the innermost tubular catheter (e.g., 130) can be manipulated to perform a therapeutic or diagnostic procedure, such as a SESAME procedure as set forth herein, or other procedure(s). As such, the therapeutic procedure can include, in some implementations, cutting into a left ventricular outflow tract obstruction to increase the effective cross-sectional area of the left ventricular outflow tract.

In some implementations, the innermost tubular catheter can include a microcatheter, and the method may include directing the microcatheter into a right ventricle of a patient, through a septum of the patient into the left ventricle of the patient, and cutting into a left ventricular outflow tract obstruction to increase the effective cross-sectional area of the left ventricular outflow tract, or other procedure. In some implementations, the first tubular catheter can include a delivery catheter to deliver a beneficial agent (e.g., liquid medicament, saline, dextrose solution, and the like) or a medical device (e.g., stent, shunt, or the like) to an anatomical location. One or more of the catheters can include one or more visualization markers (e.g., viewable under fluoroscopy or MRI) and/or one or more electrodes or one or more cutting elements to cut through anatomical tissue. The diagnostic or therapeutic procedure can be selected from the group consisting of a MIRTH procedure, a LAMPOON procedure, a PASTA (Pledget-assisted suture tricuspid valve annuloplasty) procedure, an ELASTIC procedure, a BASILICA procedure, a robotic surgical procedure, a cerclage procedure, or delivery of a medical device. In one illustration of FIG. 39C, the system of the disclosure is set up to perform a MIRTH procedure.

Figure 39C:
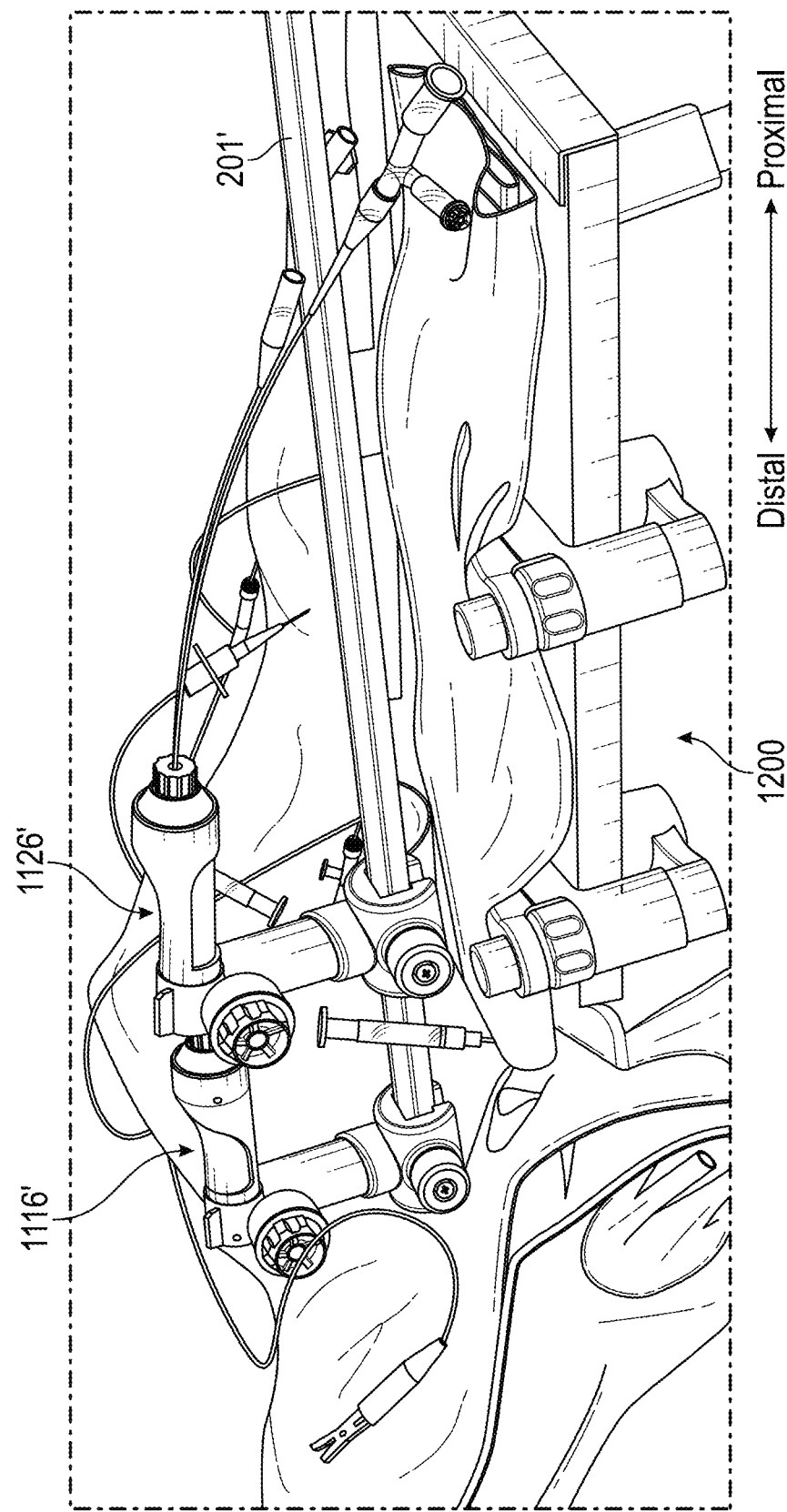
FIG. 39C is an isometric view of an actuator assembly in accordance with the present disclosure including two actuators.

A MIRTH (Myocardial Intramural Remodeling by Transvenous Tether) procedure is a transcatheter ventricular remodeling procedure, wherein a transvenous tension element is placed within the walls of the beating left ventricle and shortened to narrow chamber dimensions. Further details of the MIRTH procedure can be found in U.S. patent application Ser. No. 18/151,601, which is incorporated by reference in its entirety for all purposes. The MIRTH method can be used to reduce the dimensional size of a portion of a patient's heart. The method can include advancing a guidewire into a patient's circulatory system and into the patient's heart, advancing the guidewire through the myocardium (between layers of cardiac tissue around a chamber of a heart, for example) to define a passageway around at least a portion of the heart between an outer surface of the heart and an inner surface of the heart, exchanging the guidewire with an implant including a tensioning element so that the tensioning element traverses the passageway, advancing a lock over the tensioning element, applying tension to the tensioning element to change the dimensional size of a portion of the heart, and locking the lock to maintain the tension in the tensioning element. Such a technique can be performed utilizing system 100, or components thereof. Various supporting catheters are useful in performing a MIRTH procedure. In the context of the present disclosure, a two-catheter system can be used, as illustrated in FIG. 39C, wherein catheters 110 and 120, for example, are used to steer to the myocardium and perform a MIRTH procedure. A further illustrative procedure is set forth in International Application No. PCT/US2020/045674, which is incorporated herein by reference, wherein the disclosed catheter system 100 can be used to perform this procedure.

Figure 40A:
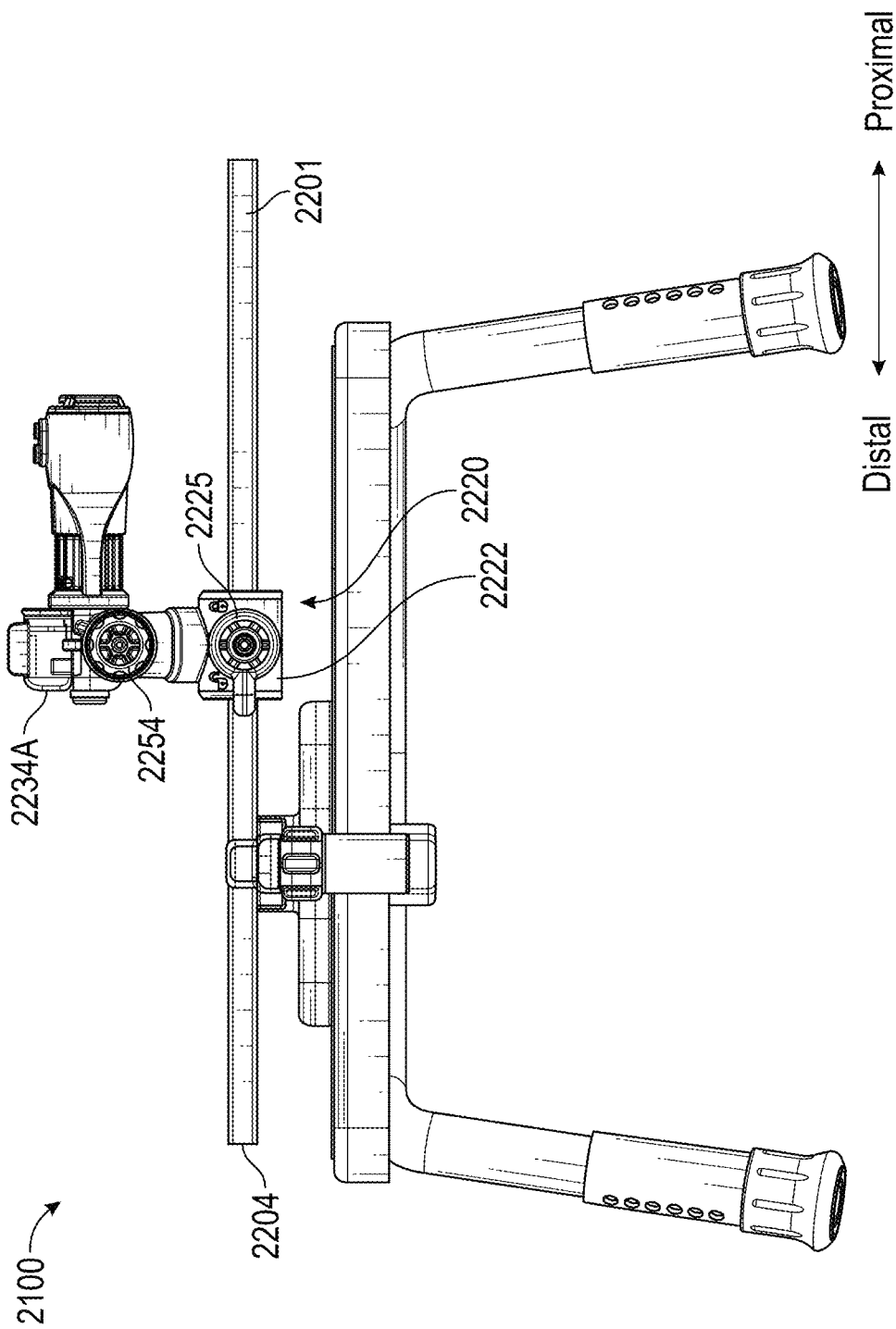
FIGS. 40A-40D are different isometric views of a further actuator assembly in accordance with the present disclosure.
Figure 40B:
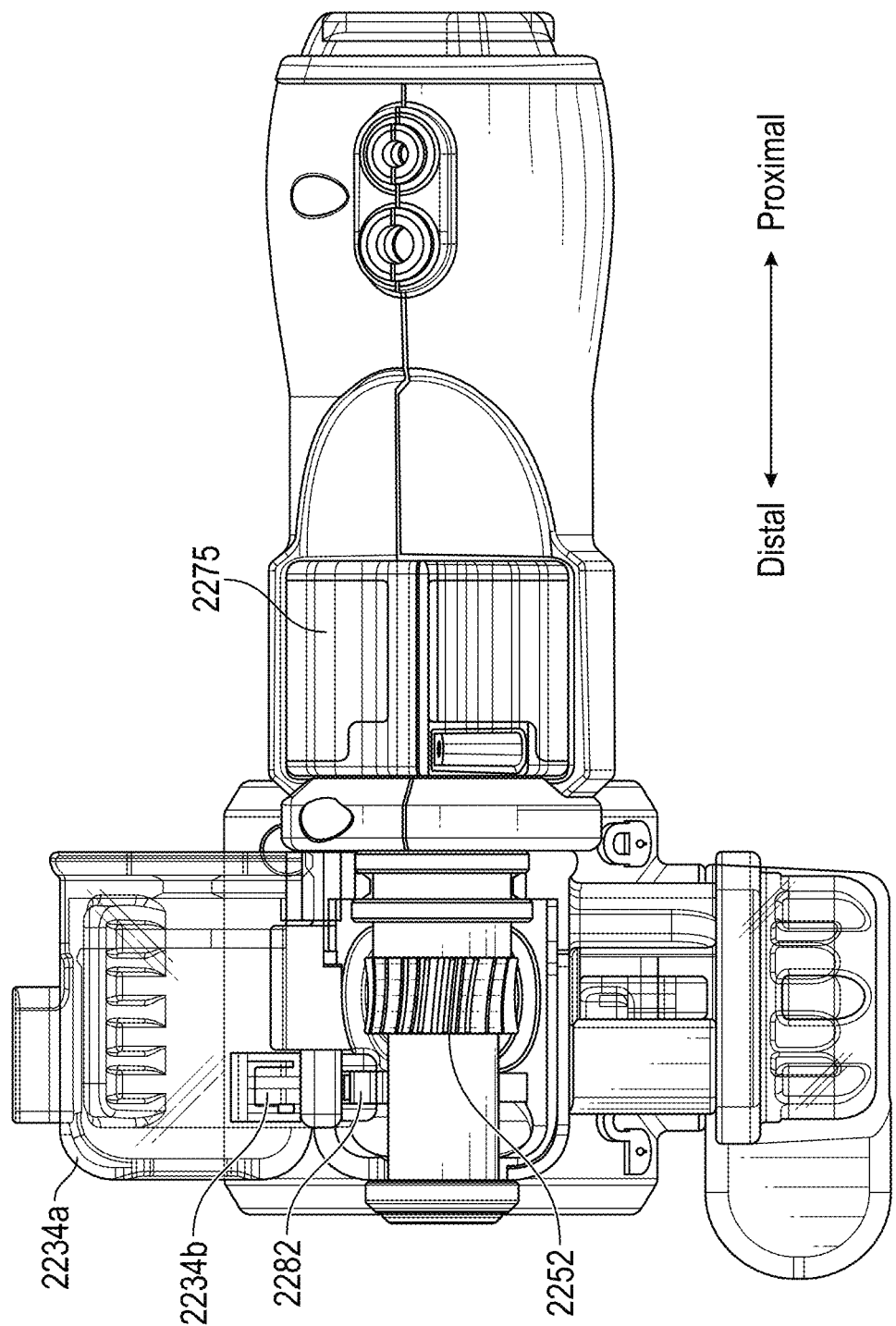
Figure 40C:
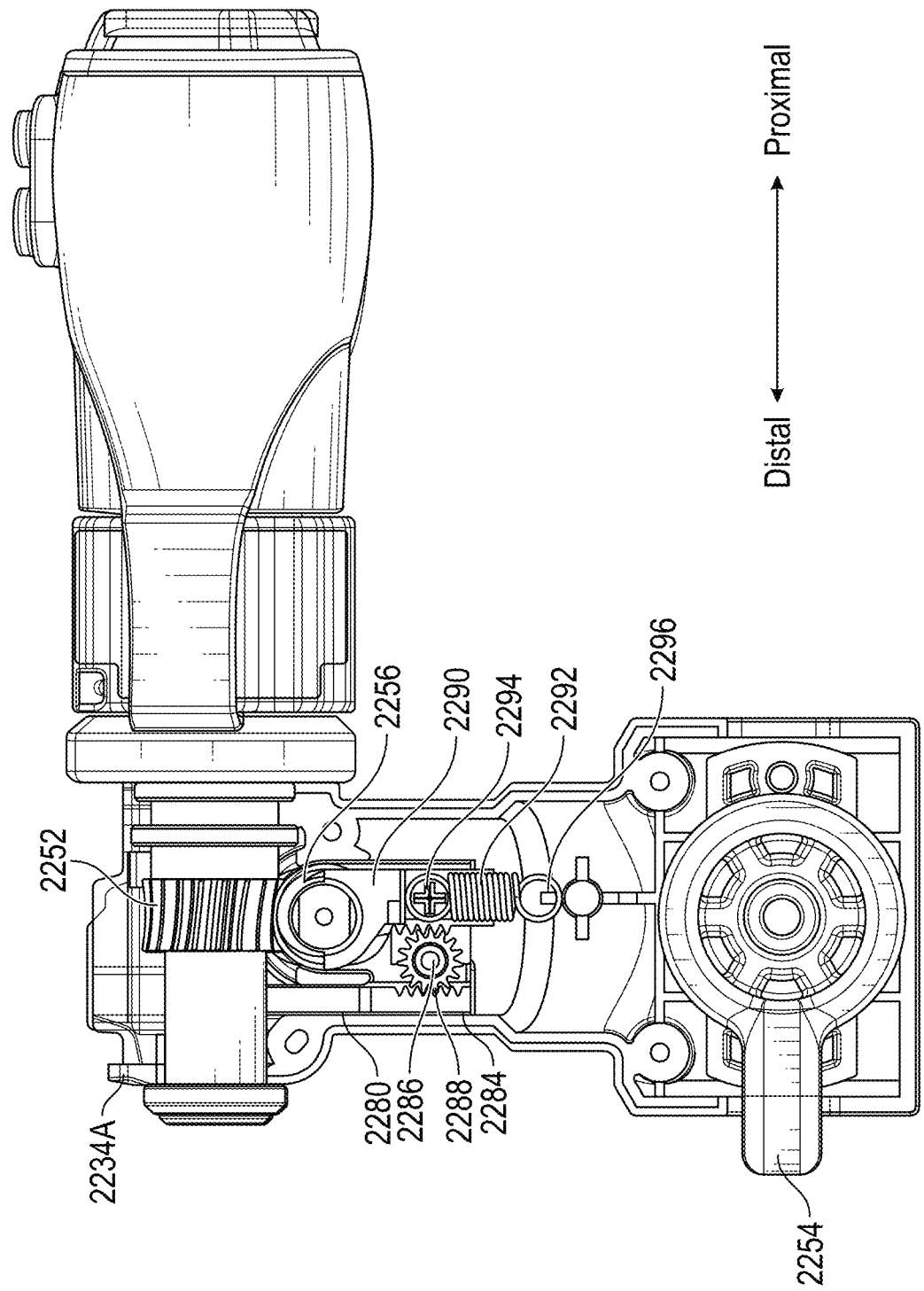

FIGS. 40A-40D depict further implementations of a catheter system in accordance with the present disclosure, or aspects thereof, having a different actuator assembly than the system of FIGS. 31-40. For purposes of reference, the proximal and distal directions of the assembly are indicated in various figures. This illustrated implementation of the actuator includes a variation with respect to that of FIGS. 31-39C, wherein the closing of the cover 2234A pushes downwardly on a pin 2280 that rotates a gear 2288 that pushes an inner support or journal 2290 upward that rotatably receives the worm gear 2256. The journal 2290 is slidably disposed within the housing of the actuator assembly, and is biased into a downward location by a tension spring 2292, wherein, when the cover 2234A is open, as illustrated in FIG. 40C, the spring 2292 pulls the journal or support 2290 downward, causing the worm gear 2256 to lower and disengage from gear 2252, permitting the gear 2252, and thus the catheter seated in the actuator, to rotate about its axis without mechanical interference from the worm gear 2256. When a desired rotational orientation is obtained for the catheter with the cover 2234A open, the cover can then be closed, causing a boss 2234B formed on the underside of the cover to push downwardly on an upper end surface 2282 (FIG. 40B) of pin 2280. With reference to FIG. 40C, downward motion of pin 2280 causes a gear rack 2284 formed into a lower surface of the pin 2280 to cause rotation of a sprocket or gear 2288 about an axle 2286. The teeth of gear 2288 are further engaged with a complementary toothed rack on journal 2290, causing journal 2290 to be pushed up against the force of the tension spring 2292, resulting in mechanical engagement between the worm gear 2256 and the gear 2252 that surrounds and is operably coupled to a respective catheter (e.g., 130).

With reference to FIG. 40A, the actuator assembly can be similar in design and operation to those illustrated in FIGS. 31-39C, with the addition of the above-described mechanism, which permits a coarse rotational adjustment of a catheter about its longitudinal axis when open. Thus, like reference numerals for the rail 2201 and other components are meant to parallel and mirror the embodiment of FIGS. 31-39C.

The top view of the assembly in FIG. 40B illustrates the cover 2234A in an open position, showing the relative location of boss 2234B that contacts and pushes down on the upper surface 2282 of pin 2280. A similar dial adjustment 2275 can be operably coupled to a pull wire as with the embodiment of FIGS. 31-39C and the same flush and sealing ports can be provided.

As mentioned above, with reference to FIG. 40C, when the top cover 2234A is open, the tension spring 2292 goes back to its contracted rest position and pulls the worm gear 2256 and its journal or mount 2290 downwardly so the worm gear 2256 disengages from the gear 2252. At this time, the catheter is free to rotate within the housing of the carriage.

Figure 40D:
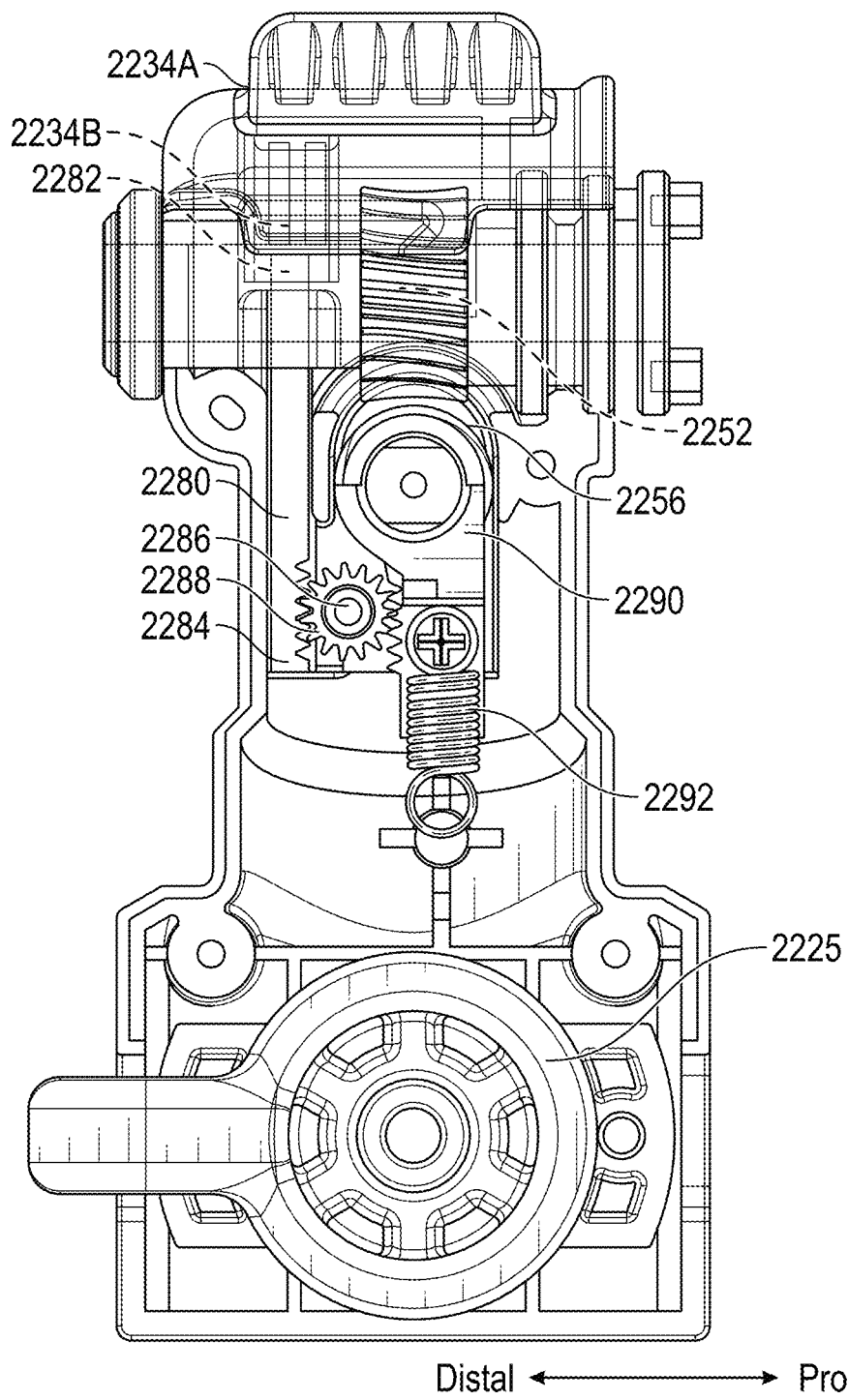

As illustrated in FIG. 40D, when the carriage top cover 2234A is closed, the boss 2234B inside the top cover 2234A pushes the pin 2280 down. The pin rotates the gear 2288 and the spring 2292 stretches and the worm gear 2256 goes up to engage gear 2252 such that the catheter rotational position is locked. Under this condition, spring 2292 is actually under tension, although this is not directly illustrated in FIG. 40D.

Figure 41:
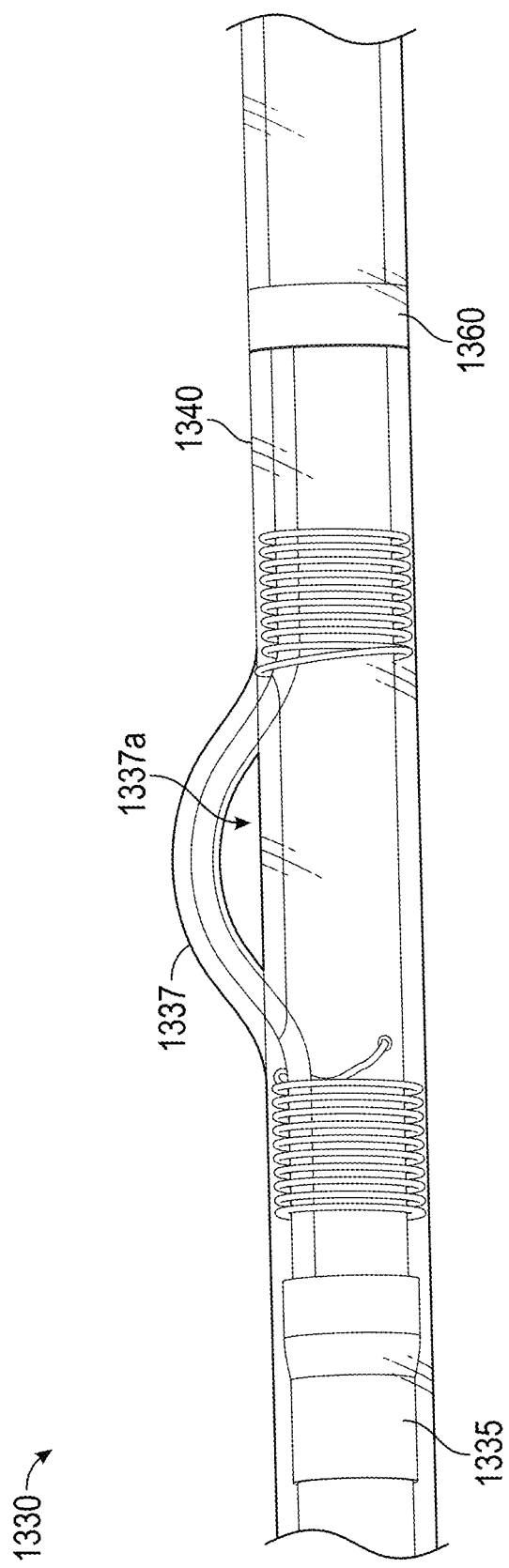
FIG. 41 is a side view of a distal portion of a further catheter in accordance with the present disclosure configured to deploy a tissue anchor out through a lateral side port of the catheter.

In further accordance with the disclosure, FIG. 41 depicts a side view of a distal portion of a further catheter 1330 in accordance with the present disclosure configured to deploy a tissue anchor out through a lateral side port of the catheter. As illustrated in FIG. 41, catheter 1330 is formed from an outer tubular member 1335 that contains a deployable anchor that can be deployed through a side port 1340 defined through tubular member 1335. Catheter further includes an electrode 1337 that includes an electrically exposed portion (not shown) to permit the completion of an electrical circuit through tissue being cut during an electrosurgical procedure. The electrically exposed portion can exist along the outer edge of the arch facing outwardly, wherein insulating material remains around the remaining circumference of the electrode 1337. The electrode 1337, as depicted, extends through a respective side port 1337A defined through wall 1335 of the catheter 1330. But, it will be appreciated that the electrode can simply be formed into or protruding from the sidewall without a side port 1337A as with electrode 137 illustrated in other embodiments herein. The electrode 1337 can be configured to be deployed outwardly from the side port 1337A, for example, by pushing the electrode to apply a column force or axial compression to the electrode, causing the electrode 1337 to protrude from the port 1337A. Similarly, the electrode can be spring loaded or otherwise be biased to extend outwardly through the port 1337A, wherein the electrode can be pushed laterally back into the port by withdrawing the catheter 1330 proximally into a guiding catheter or sheath, for example. As illustrated, catheter 1330 further includes a distal marker band 1360 which can comprise a band of radiopaque material or be configured to be visible under additional or alternative visualization modalities as set forth herein.

Figure 43:
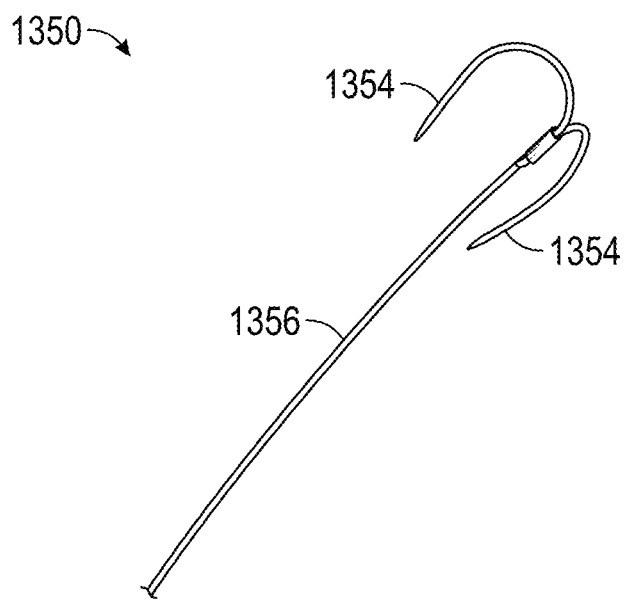
FIGS. 43-44 are views of the tissue anchor removed from the catheter of FIG. 41.
Figure 44:
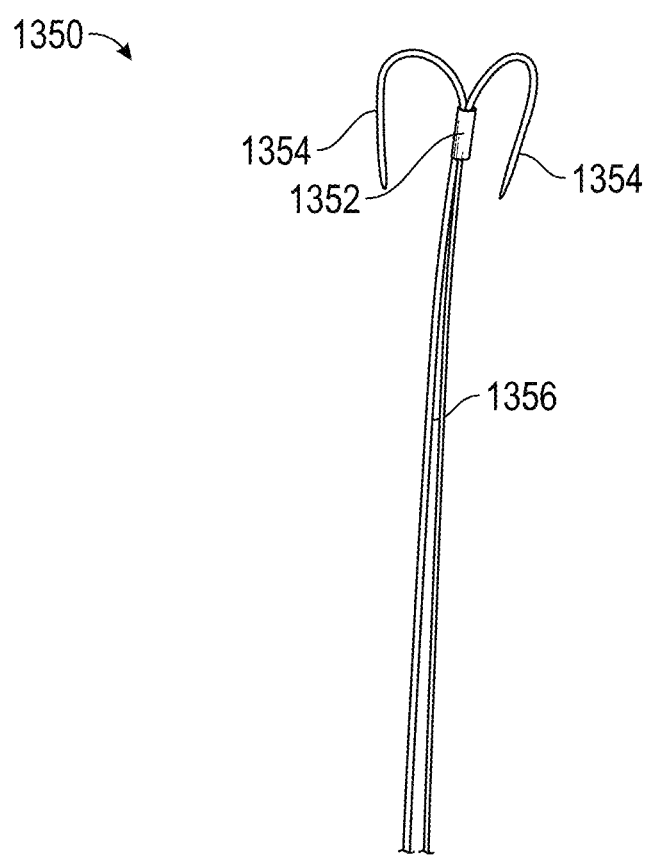

FIGS. 42A-42D are images of the catheter of FIG. 41 illustrating successive stages of deploying tissue anchor 1350 out through the lateral side port 1340 of the catheter 1330. FIG. 42A illustrates catheter 1330 prior to deployment of the anchor 1350, wherein the relative locations of the anchor exit port 1340, distal marker band 1360, electrode 1337, and side electrode port 1337A are presented. FIG. 42B illustrates an initial step of deployment of anchor 1350, wherein a pair of tines 1354 begin exiting out of port 1340, which is located distally with respect to the electrode 1337. In other implementations, the lateral anchor port 1340 can be located proximally with respect to the electrode 1337. FIG. 42C illustrates the tines 1354 of the anchor when they are about halfway deployed, and FIG. 42D illustrates the tines 1354 of the anchor 1350 when fully deployed. As illustrated in FIGS. 43-44, the anchor 1350 is comprised of an elongate wire 1356 that is slidably disposed along a lumen defined along the interior of catheter 1330 inside tubular body 1335 that is in fluid communication with the exit port 1340. Pushing the wire 1356 distally with respect to the outer tubular body 1335 causes the anchor 1350 to deploy, wherein the tines 1354 of the anchor 1350 are directed proximally to facilitate the anchoring of the tines 1354 of the anchor 1350 into tissue. The tines 1354 can be coupled to the wire 1356 at a junction 1352, wherein the junction can prevent rotation or flexing between the wire and tines 1354, or the junction 1352 can be a swiveled coupling, if desired. As will be appreciated, the two-tined design of anchor 1350 facilitates lateral deployment, whereas the three-tined design of implementation 150 (FIG. 14) is well suited for deployment out of a distal passage of a catheter (e.g., 130).

Figure 45A:
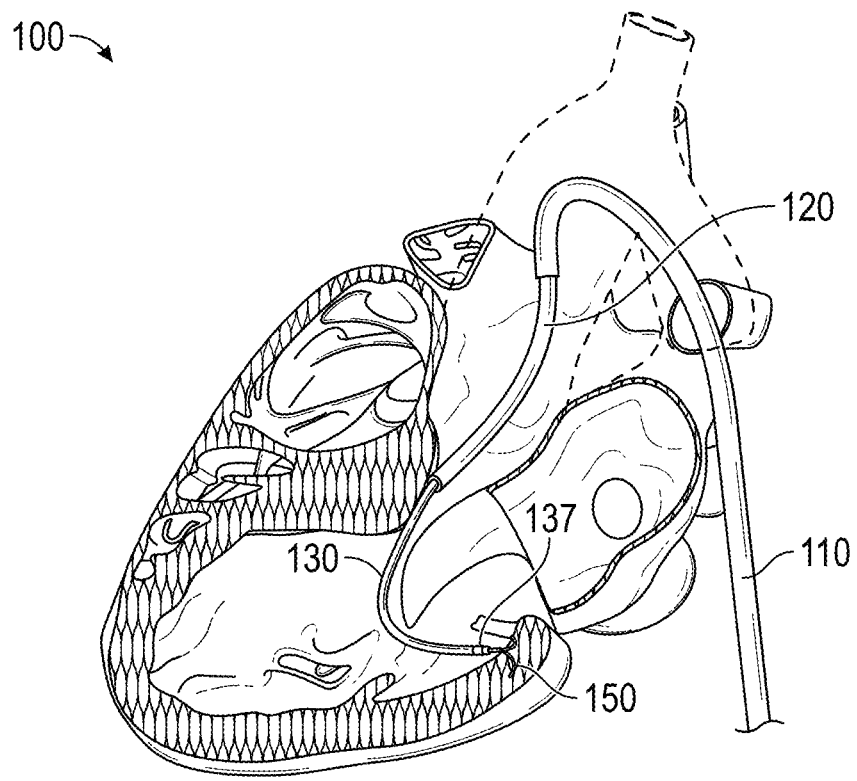
FIGS. 45A-45B illustrate aspects of utilizing a catheter-based system in accordance with the present disclosure to perform a LAMPOON procedure.
Figure 45B:
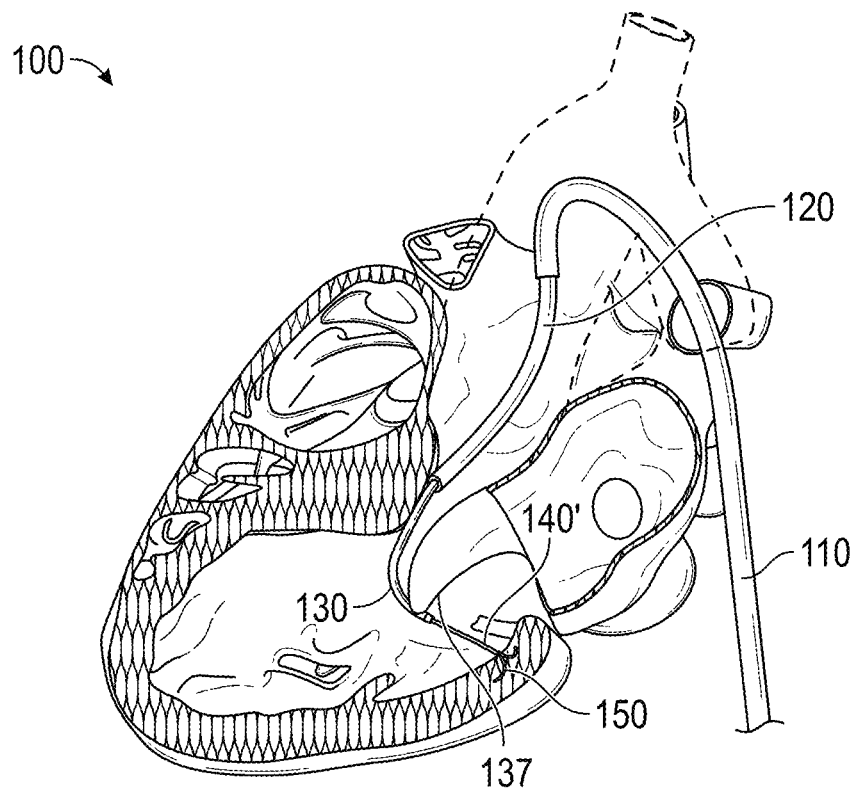

FIGS. 45A-45B illustrate aspects of utilizing a catheter-based system (e.g., 100) in accordance with the present disclosure to perform a Laceration of the Anterior Mitral leaflet to Prevent Outflow Obstruction (LAMPOON) procedure, which is a transcatheter electrosurgical technique to split the anterior mitral valve leaflet immediately prior to transcatheter mitral valve replacement (TMVR). As illustrated, to facilitate this procedure, catheter 110 is deflected over the aortic arch into the ascending aorta, wherein the distal end of the catheter 110 is outside of the aortic valve. Catheter 120 is deployed distally of catheter 110 until the distal end of catheter 120 is just under the aortic valve. Catheter 130, which include a cutting element 137, is deployed and steered to the wall of the left ventricle where anchor 150 is deployed out of the distal end of catheter 130 and into the wall of the left ventricle. Catheter 130 can then be retracted proximally to reveal a tether in the form of a hypotube 140' that has sufficient column strength to help insert anchor 150 into the tissue. The catheter 130 can then be aligned such that the cutting element 137, whether electrosurgical, a sharp surface, or an ultrasonic cutter is placed proximate the anterior mitral leaflet to cut through the anterior mitral leaflet by starting cutting at a bottom edge of the anterior mitral leaflet, and then reciprocating back and forth to cut through the leaflet. The catheter 130 can be selectively withdrawn to maintain the cutting element in an appropriate position to continue cutting the leaflet until the cutter 137 is near the anterior mitral annulus, and the anterior mitral leaflet has been split. After splitting the valve leaflet, the replacement valve can be installed. The rigidity of element 140', whether provided as a solid element or a tubular element cooperates with the stiffness of the catheter 130 to help position the cutter in a correct location to continue cutting tissue.

Figure 46A:
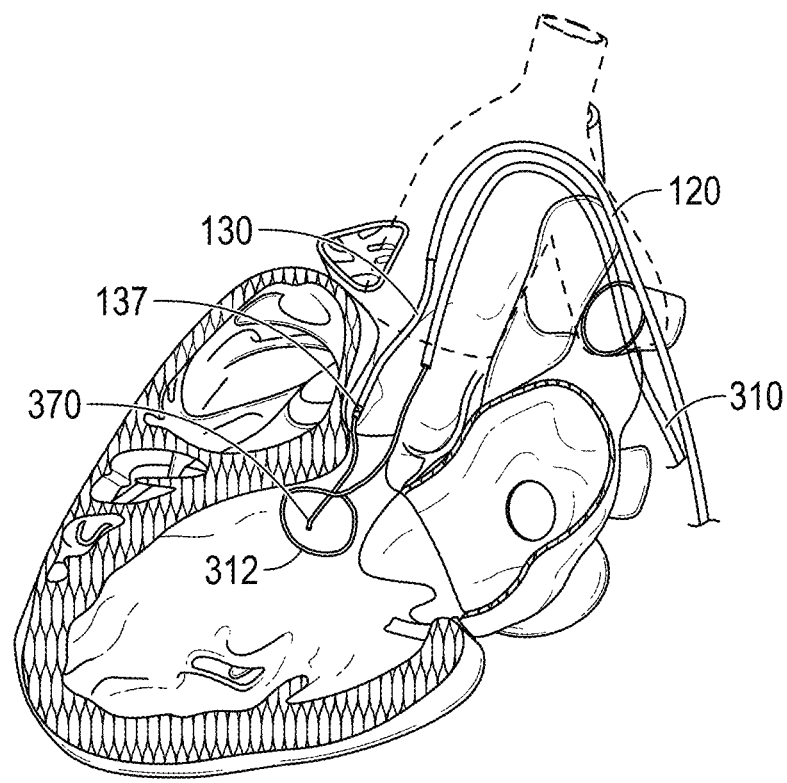
FIGS. 46A-46B illustrate aspects of utilizing a catheter-based system in accordance with the present disclosure to perform a BASILICA procedure.
Figure 46B:
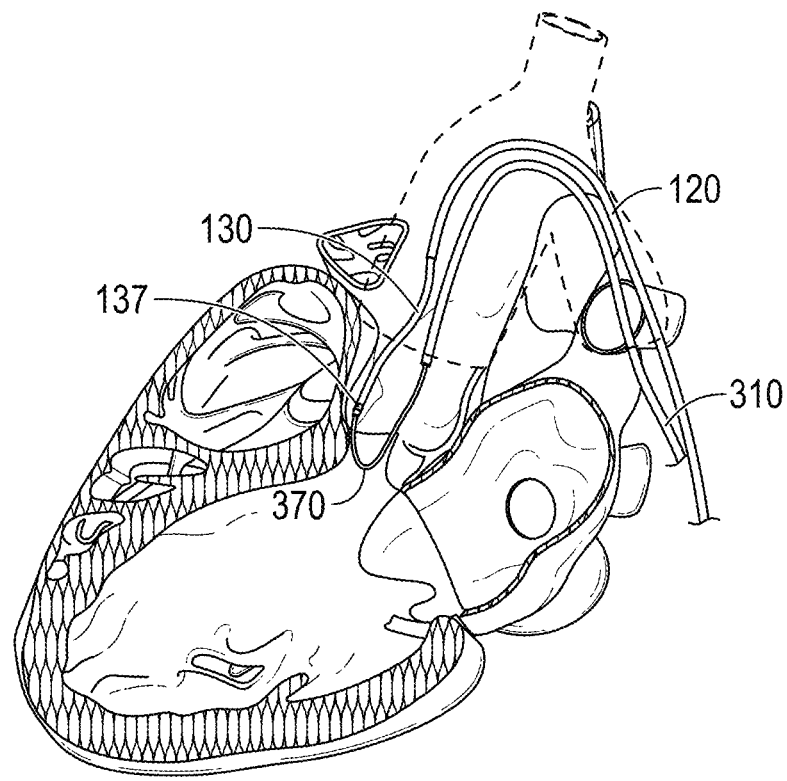

FIGS. 46A-46B illustrate aspects of utilizing a catheter-based system in accordance with the present disclosure to perform a BASILICA procedure for cutting a leaflet of the aortic valve. In this implementation, catheter 120 deflects over the aortic arch and down into the ascending aorta. Catheter 130 supports a crossing wire 370 inside a cusp of the aortic valve. The crossing wire 370 is advanced through the aortic valve leaflet near a radially outer edge of the leaflet, such as by electrifying the wire 370 wherein the wire 370 includes an electrically exposed distal end and includes an electrically insulating jacket proximal to the distal end of the wire 370. A snare catheter 310 is introduced alongside catheters 120, 130 including a tubular member with a snare 312 terminating in a loop that surrounds and can capture the distal end of the wire 370 after the wire 370 has formed a hole through the aortic valve leaflet. The wire 370 is pulled into the distal end of catheter 310. At this point in the procedure, the wire 370, pulled into and held in place in catheter 310 can then provide a rail or guide that can permit a cutter 137 of any suitable form to enlarge the hole formed by wire 370. The wire 370 can be pulled further into catheter 310 to apply tension to wire 370 to provide a lateral force component to catheter 130, and cutter 137 to cause the cutter to cut through the aortic valve leaflet. This procedure can be repeated on the other two aortic valve leaflets.

Figure 47B:
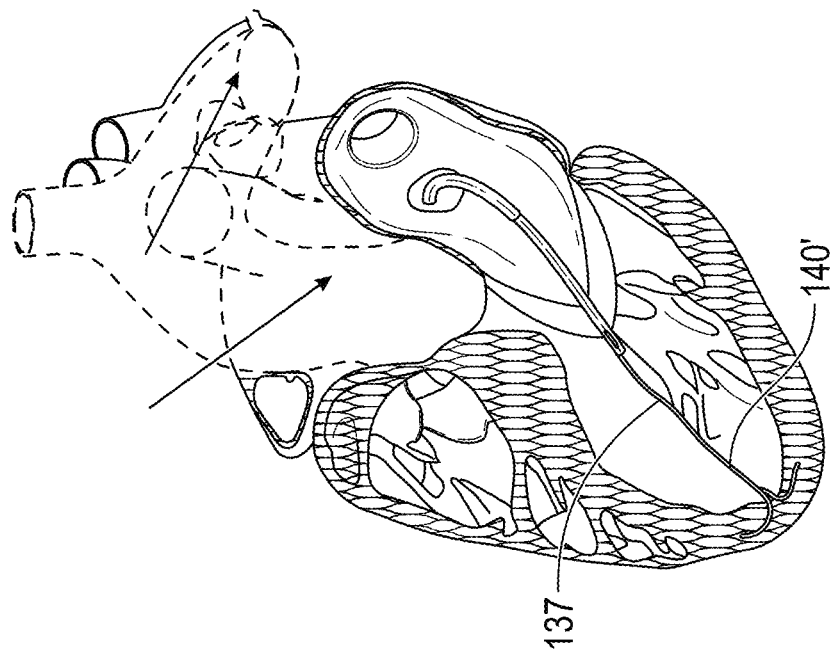
FIGS. 47A-47B illustrate aspects of utilizing a catheter-based system in accordance with the present disclosure to perform an ELASTIC procedure.
Figure 47A:
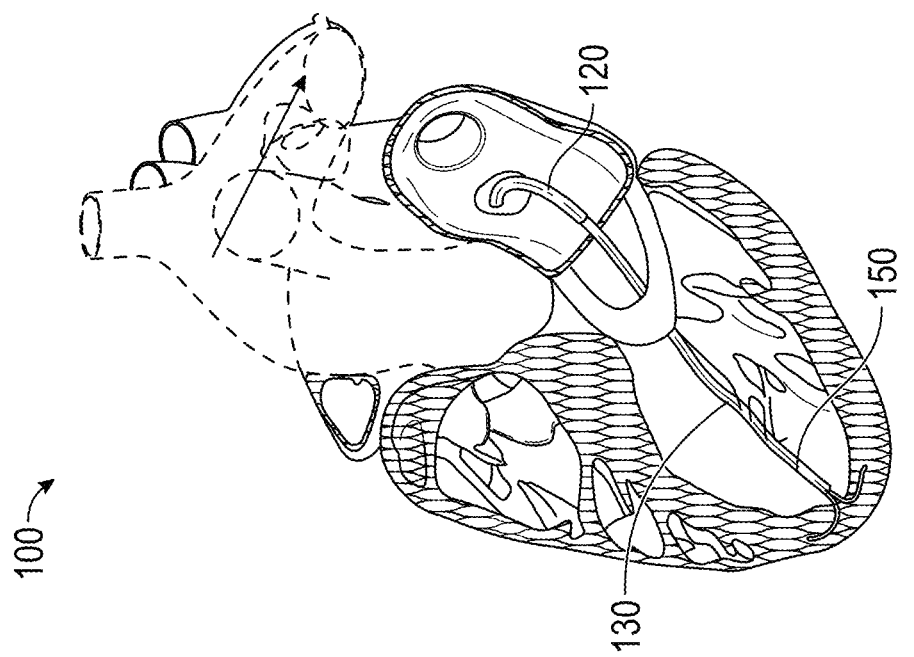

FIGS. 47A-47B illustrate aspects of utilizing a catheter-based system in accordance with the present disclosure to perform an ELASTIC (Electrosurgical Laceration of Alfieri STItCh (ELASTIC) procedure to remove a mitral clip or Alfieri stitch to facilitate placement of a TMVR. In this procedure, catheter 120 is deployed over the atrial septum from right to left toward the mitral valve and left ventricular apex. Catheter 130 is deployed distally to the apex of the left ventricle and anchor 150 is deployed in the tissue in that location. The catheter 130 is retracted proximally until the cutter 137 is in the region of the Alfieri stitch, or the mitral clip attaching the anterior and posterior mitral leaflets to each other. The cutter 137 is aligned with tissue near the stitch, and the cut is made through tissue to separate the two leaflets, permitting installation of a TMVR. The tether 140' can include a rod or tube to provide sufficient stiffness to help guide the cutting in cooperation with the movement of catheter 130 bearing cutter 137.

By way of further example, instead of being configured for manual operation, the actuator assembly can be configured to be received by an actuator hub of a robotic surgical system. The system (e.g., 100) can be introduced into a patient by way of a femoral access point, carotid, or jugular access point, depending on the procedure being performed. The system can be sized and configured to be introduced to a patient's vasculature to perform a procedure within the neurovascular region of a patient. It will be appreciated that system (e.g., 100) can be used in a variety of percutaneous cardiovascular, thoracic, or laparoscopic procedures, as well as accessing the brain of a patient via the circulatory system or sinus passages of a patent. The systems of the disclosure can be further used to access the digestive system of a patient as well as the urinary or reproductive system of a patient.

The disclosure also provides an electrosurgical system including a radio frequency power supply (such as that described in U.S. Pat. No. 6,296,636, which is incorporated by reference herein in its entirety for any purpose whatsoever) operably coupled to the electrode(s) (e.g., 137, 137) and anchor, if desired (e.g., 150). The radio frequency power supply can be operably (and selectively) coupled to the electrodes by way of a cable or other conductors. Any suitable power level and duty cycle can be used in accordance with the disclosed embodiments. For example, continuous duty cycle (cutting) radiofrequency ("RF") energy can be used, for example, at a power level between about 10 and about 50 Watts, for example, or any increment therebetween of about one watt. The cuts can be made by applying power for between about one half of a second and about five seconds, or any increment therebetween of about one tenth of a second. The electrosurgery generator can be the Medtronic Force FX C Generator that achieves 5 W to 300 Watts of monopolar radiofrequency (RF) energy, for example.

Implementations of the guidewires for use with the disclosed embodiments preferably include a sterile, single use device intended to cut soft tissue. References to dimensions and other specific information herein is intended to be illustrative and non-limiting. In one implementation, the disclosed guidewire has an outer diameter of 0.035" and a working length of 260-300 cm. The proximal end of the disclosed guidewire, which has no patient contact, can be un-insulated to allow for connection to an electrosurgery generator if desired.

The devices and methods disclosed herein can be used for other procedures in an as-is condition, or can be modified as needed to suit the particular procedure. This procedure for cutting the myocardium can be used in support of a variety of procedures. Likewise, while it can be appreciated that a monopolar cutting system is disclosed, in certain implementations, it is also possible to configure the system to operate in a bipolar configuration. During the step of myocardium laceration, the system can be configured to deliver energy to the myocardium with electrosurgical pads coupled to the patient to complete the circuit. When lacerating the myocardium or other structure with the bent denuded cutting wire, most of the energy is still dissipated in the patient.

In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

What is claimed is:

1. A method of performing a medical procedure, comprising:
   providing a medical device, the medical device including:
      an elongate tether having a proximal end configured to be anchored to a proximal anchor point outside of a patient's anatomy and a distal end having a tissue anchor disposed thereon to penetrate through myocardial tissue to permit tension to be applied to and maintained along the elongate tether when the proximal end of the elongate tether is anchored to the proximal anchor point and the tissue anchor is anchored into myocardial tissue;
      a first tubular catheter surrounding the elongate tether and being slidably displaceable along and with respect to the elongate tether when the elongate tether is under tension, the first tubular catheter having a proximal end, a distal end, and a cutter; and
      a second tubular catheter surrounding the first tubular catheter and being slidably displaceable along and with respect to the first tubular catheter, the second tubular catheter having a proximal end and a distal end;
   directing the medical device to a target location inside a patient's left ventricle proximate a native tissue obstruction in a left ventricular outflow tract of the patient;
   placing the distal end of the second tubular catheter in a first location located proximally with respect to the tissue obstruction;
   placing the distal end of the first tubular catheter in a second location located distally with respect to the tissue obstruction;
   penetrating the myocardial tissue with the tissue anchor to secure the distal end of the elongate tether in place with respect to the myocardium;
   orienting the cutter of the first tubular catheter toward the native tissue obstruction; and
   reciprocating the first tubular catheter along the elongate tether to cause the cutter to cut into the native tissue.

2. The method of claim 1, wherein the first tubular catheter includes a distally-facing flush port configured to direct a pressurized fluid over the cutter of the first tubular catheter, and wherein the method further includes directing the pressurized fluid out of the distally-facing flush port over the cutter while reciprocating the first tubular catheter.

3. The method of claim 1, wherein the cutter includes an electrode operably coupled to electrical circuitry that is configured to determine a state of the anatomical tissue.

4. The method of claim 1, wherein the cutter includes an ultrasonically-driven cutter.

5. The method of claim 1, wherein the cutter is operably coupled to electrical circuitry, wherein the electrical circuitry is configured to correlate a voltage drop or a current drop of the cutter with a state selected from the group consisting of (i) a state of tissue being cut by the electrode, (ii) a state of fouling of the electrode.

6. The method of claim 2, wherein the pressurized fluid is a dielectric fluid.

7. The method of claim 6, wherein the dielectric fluid includes a dextrose solution.

8. The method device of claim 1, wherein the medical device further includes an actuator assembly coupled to a proximal region of the elongate tether, a proximal region of the first tubular catheter, and a proximal region of the second tubular catheter.

9. The method device of claim 8, wherein the medical device further includes a third tubular catheter surrounding the second tubular catheter and being slidably displaceable along and with respect to the second tubular catheter, the third tubular catheter having a proximal end and a distal end, and further wherein a proximal end of the third tubular catheter is coupled to the actuator assembly.

10. The method of claim 9, wherein the actuator assembly further includes a first actuator operably coupled to a proximal end of the first tubular catheter, and wherein the first actuator is configured to advance and retract the first tubular catheter proximally and distally over the elongate tether when the elongate tether is under tension.

11. The method of claim 10, wherein the actuator assembly further includes a second actuator operably coupled to a proximal end of the second tubular catheter, wherein the second actuator is configured to advance and retract the second tubular catheter proximally and distally over the first tubular catheter, and further wherein the distal end of the second tubular catheter is capable of being retracted proximally past the distal end of the first tubular catheter.

12. The method of claim 11, wherein the actuator assembly further includes a third actuator operably coupled to a proximal end of the third tubular catheter, wherein the third actuator is configured to advance and retract the third tubular catheter proximally and distally over the second tubular catheter, and further wherein the distal end of the third tubular catheter is capable of being retracted proximally past the distal end of the first tubular catheter and the distal end of the second tubular catheter.

13. The method of claim 1, wherein each of the first tubular catheter and second tubular catheter to permit an operator to determine relative axial and rotational location of each of the first tubular catheter and second tubular catheter relative to each other and surrounding anatomy.

14. The method of claim 1, further comprising conforming a shape of the first tubular catheter to match that of the native tissue obstruction such that the first tubular catheter is in at least substantially continuous contact with the native tissue obstruction along a length of the tissue obstruction.

15. The method of claim 1, wherein the first tubular catheter is reciprocated along the elongate tether to cut an incision into the obstruction to enlarge an effective cross-sectional area of the left ventricular outflow tract of the patient.

16. The method of claim 1, wherein the first tubular catheter is reciprocated along the elongate tether to cut an incision into the obstruction until the cutting element traverses a straight path between the distal end of the second tubular catheter and the tissue anchor.

17. The method of claim 1, wherein the cutter is formed at least in part from radiopaque material.

18. The method of claim 1, wherein the cutter includes a diamond coated wire.

* * * * *